United States Patent
Pinsky et al.

(10) Patent No.: US 10,874,719 B2
(45) Date of Patent: Dec. 29, 2020

(54) NUCLEOTIDE PHOSPHATE DISSIPATION AS A TREATMENT FOR VASCULAR DISORDERS

(71) Applicant: THE REGENTS OF THE UNIVERSITY OF MICHIGAN, Ann Arbor, MI (US)

(72) Inventors: David J. Pinsky, Ann Arbor, MI (US); Danica Petrovic-Djergovic, Ypsilanti, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/594,687

(22) Filed: Jan. 12, 2015

(65) Prior Publication Data

US 2016/0074484 A1    Mar. 17, 2016

Related U.S. Application Data

(63) Continuation of application No. 12/261,870, filed on Oct. 30, 2008, now abandoned.

(60) Provisional application No. 60/985,106, filed on Nov. 2, 2007, provisional application No. 60/983,649, filed on Oct. 30, 2007.

(51) Int. Cl.
*A61K 38/46* (2006.01)

(52) U.S. Cl.
CPC .... *A61K 38/465* (2013.01); *C12Y 301/03005* (2013.01)

(58) Field of Classification Search
CPC .... A61K 38/177; A61K 38/465; A61K 38/00; A61K 49/0004; C12Y 301/03005
USPC ................. 424/94.6, 133.1, 130.1
See application file for complete search history.

(56) References Cited

U.S. PATENT DOCUMENTS

| | | |
|---|---|---|
| 5,733,916 A | 3/1998 | Neely |
| 6,001,842 A | 12/1999 | Neely |
| 6,387,645 B1 | 5/2002 | Ford et al. |
| 6,447,771 B1 | 9/2002 | Ford et al. |
| 6,759,214 B1 | 7/2004 | Chadwick et al. |
| 6,783,959 B1 | 8/2004 | Chadwick et al. |
| 6,858,207 B2 | 2/2005 | Ford et al. |
| 6,867,177 B2 | 3/2005 | Pinsky |
| 7,129,074 B2 | 10/2006 | Sevigny |
| 7,247,300 B1 | 7/2007 | Chen et al. |
| 7,264,908 B2 | 9/2007 | Kaneko et al. |
| 7,534,423 B2 | 5/2009 | Jalkanen |

FOREIGN PATENT DOCUMENTS

WO    WO-2006/012404 A2    2/2006

OTHER PUBLICATIONS

Doyle et al. Neuropharmacol. 2018, 55, 310-318.*
Haldeman et al.,Spine, 2002, 27, pp. 49-55.*
Weill Cornell Brain and spine center, 2018, pp. 1-2.*
Jin et al. J. Leuk biol 2010 87, pp. 779-789.*
Airas et al, CD73 is Involved in Lymphocyte Binding to the Endothelium: Characterization of Lymphocyte-Vascular Adhesion Protein 2 Identifies It as CD73, *J. Exp. Med.*, 182:1603-8 (1995).
Atkinson et al, Ecto-nucleotides of the CD39/NTPDase family modulate platelet activation and thrombus formation: Potential as therapeutic targets, *Blood Cells, Molec. Dis.*, 36:217-22 (2006).
Beldi et al, The role of purinergic signaling in the liver and in transplantation: effects of extracellular nucleotides on graft hepatic vascular injury, rejection and metabolism, *Front. Biosci.*, 13:2588-603 (2008).
Bouma et al, The Anti-Inflammatory Potential of Adenosine in Ischemia-Reperfusion Injury: Established and Putative Beneficial Actions of a Retaliatory Metabolite, Shock, 8(5):313-20 (1997).
Braun et al, Focal cerebral ischemia enhances glial expression of ecto-5'-nucleotidase, *Brain Research*, 766:213-26 (1997).
Dare et al, Modulation of glial cell functions by adenosine receptors, *Physiology & Behavior*, 92:15-20 (2007).
Deaglio et al, Adenosine generation catalyzed by CD39 and CD73 expressed on regulatory T cells mediates immune suppression, *Journal Experimental Medicine*, 204(6):1257-65 (2007).
Dwyer et al, The Transgenic Expression of Human CD39 on Murine Islets Inhibits Clotting of Human Blood, *Transplantation*, 82(3):428-32 (2006).
Eckle et al, Cardioprotection by Ecto-5'-nucleotidase (CD73) and A2B Adenosine Receptors, *Circulation*, 115:1581-90 (2007).
Eltzschig et al, ATP Release From Activated Neutrophils Occurs via Connexin 43 and Modulates Adenosine-Dependent Endothelial Cell Function, *Circ. Res.*, 99:1100-8 (2006).
Eltzschig et al, Endogenous adenosine produced during hypoxia attenuates neutrophil accumulation: coordination by extracellular nucleotide metabolism, *Blood*, 104:3986-92 (2004).
Eltzschig et al, Nucleotide metabolism and cell-cell interactions, *Methods Mol. Biol.*, 341:73-87 (2006).
Fredholm, Adenosine, an endogenous distress signal, modulates tissue damage and repair, *Cell Death and Differential*, 14:1315-23 (2007).

(Continued)

*Primary Examiner* — Robert B Mondesi
*Assistant Examiner* — Mohammad Y Meah
(74) *Attorney, Agent, or Firm* — Marshall, Gerstein & Borun LLP

(57) ABSTRACT

The present invention provides a method of treating or preventing immunoinflammatory, vascular, thrombotic or ischemic disorders in a subject, the method comprises administering to the subject an agent which dissipates nucleotide phosphates or generates a product which stimulates adenosine receptors. The present invention also provides a method of treating or preventing immunoinflammatory, thrombotic or ischemic disorders in a subject by inhibiting leukocyte infiltration into a site which comprises administering to the subject an effective amount a described agent. Agents described for use in the methods of the invention include CD73, a fragment a mutant, or a modified form thereof.

7 Claims, 35 Drawing Sheets

Specification includes a Sequence Listing.

(56) References Cited

OTHER PUBLICATIONS

Genbank accession No. NM_002526, Version NM_002526.1, *Homo sapiens* 5'-nucleotidase, ecto, (CD73) (NTSE), mRNA, dated Mar. 24, 2007.

Genbank accession No. NM_200932, Version NM_200932.1, Danio rerio 5'-nucleotidase, ecto (CD73) (nt5e), mRNA, dated Jan. 21, 2004.

Grenz et al, Protective Role of Ecto-5'-Nucleotidase (CD73) in Renal Ischemia, *J. Am. Soc. Nephrol.*, 18:833-45 (2007).

Haller et al, Reconstitution of CD39 in liposomes amplifies nucleoside triphosphate diphosphohyrolase activity and restores theromboregulatory properties, *J. Vasc. Surg.*, 43:816-23 (2006).

Hart et al, Direct Treatment of Mouse or Human Blood With Soluble 5'-Nucleotidase Inhibits Platelet Aggregation, Arterioscl., *Thromb., Vasc. Biol.*, 28:1477-83 (2008).

Hart et al, Extracellular Adenosine Production by Ecto-5'-Nucleotidase Protects During Murine Hepatic Ischemic Preconditioning, *Gastroenterology*, 135:1739-50 (2008).

Hart et al, Role of extracellular nucleotide phosphohydrolysis in intestinal ischemia-reperfusion injury, *FASEB J.*, 22:2784-97 (2008).

Hasko et al, Adenosine inhibits IL-12 and TNF-a production via adenosine A2a receptor-dependent and independent mechanisms, *FASEB J.*, 14:2065-74 (2000).

Hasko et al, Adenosine receptor signaling in the brain immune system, *Trends Pharmacol Sci.*, 26(10):511-6 (2005).

Hasko et al, Shaping of monocyte and macrophage function by adenosine receptors, *Pharmacol. Ther.*, 113(2):264-75 (2007).

Henttinen et al, Adherent Leukocytes Prevent Adenosine Formation and Impair Endothelial Barrier Function by Ecto-5'-nucleotidase/CD-73-dependent Mechanism, *J. Biol. Chem.*, 278(27):24888-95 (2003).

Huang et al, Rose of A2a Extracellular Adenosine Receptor-Mediated Signaling in Adenosine-Mediated Inhibition of T-Cell Activation and Expansion, *Blood*, 90:1600-10 (1997).

Jalkanen et al, VAP-1 and CD73, Endothelial Cell Surface Enzymes in Leukocyte Extravasation, Arteriosclerosis, *Thrombosis and Vascular Biology*, 28:18-26 (2008).

Jonigk et al, Recipient-Derived Neoangiogenesis of Arterioles and Lymphatics in Quilty Lesions of Cardiac Allografts, *Transplantation*, 84(10):1335-42 (2007).

Khoa et al, Th1 Cytokines Regulate Adenosine Receptors and Their Downstream Signaling Elements in Human Microvascular Endothelial Cells, *J. Immunol.*, 171:3991-8 (2003).

Kiss et al, IFN-B protects from vascular leakage via up-regulation of CD73, *Eur. J. Immunol.*, 37:3334-8 (2007).

Kluft et al., How best to counteract the enemies? by controlling inflammation in the coronary circulation, *Europ. Heart J. suppl*, 4:G53-65 (2002).

Koshiba et al, Memory of Extracellular Adenosine A2A Purinergic Receptor-mediated Signaling in Murine T Cells, *J. Biol. Chem.*, 272(1):25881-9 (1997).

Koszalka et al, Targeted Disruption of cd73/Ecto-5'-Nucleotidase Alters Thromboregulation and Augments Vascular Inflammatory Response, *Circ. Res.*, 95:814-21 (2004).

Kreckler et al, Adenosine Inhibits Tumor Necrosis Factor-a Release from Mouse Peritoneal Macrophages via A2A but not the A3 Adenosine Receptor, *J. Pharmacol. Exper. Therapeut*, 317(1):172-80 (2006).

Leal et al, NTPDase and 5'-nucleotidase activities in platelets of human pregnants with a normal or high risk for thrombosis, *Mol. Cell Biochem.*, 304:325-30 (2007).

Lennon et al, Neutrophil-derived 5'-Adenosine Monophosphate Promotes Endothelial Barrier Function via CD73-mediated Coversion to Adenosine and Endothelial A2B Receptor Activation, *J. Exp. Med.*,188:1433-43 (1998).

Marcus et al, Role of CD39 (NTPDase-1) in Thromboregulation, Cerebroprotection, and Cardioprotection, *Seminars in Thrombosis and Hemostasis*, 31(2):234-46 (2005).

Mills et al, CD73 is required for efficient entry of lymphocytes into the central nervous system during experimental autoimmune encephalomyelitis, *PNAS*, 105(7):9325-30 (2008).

Misumi et al, Primary structure of human placental 5'-nucleotidase and identification of the glycolipid anchor in the mature form, *Eur. J. Biochem.*, 191:563-569 (1990).

Nemeth et al, Adenosine Augments IL-10 Production by Macrophages through an A2B Receptor-Mediated Posttranscriptional Mechanism, *J. Immunol.*, 75:8260-70 (2005).

Olah et al, Adenosine Receptor Subtypes: Characterization and Therapeutic Regulation, *Annu. Rev. Pharmacol. Toxicol.*, 35:581-606 (1995).

Pinsky et al, Elucidation of the thromboregulatory role of CD39/ectoapyrase in the ischemic brain, *J. Clin. Invest.*, 109:1031-40 (2002).

Sitkovsky, Use of the A2A adenosine receptor as a physiological immunosuppressor and to engineer inflammation in vivo, *Biochem. Pharmacol.*, 65:493-501 (2003).

Synnestvedt et al, Ecto-5'-nucleotidase (CD73) regulation by hypoxia-inducible factor-1 mediates permeability changes in intestinal epithelia, *J. Clin. Invest.*, 110(7):993-1002 (2002).

Thompson et al, Crucial Role for Ecto-5'-Nucleotidase (CD73) in Vascular Leakage during Hypoxia, *J. Exp. Med.*, 200(11):1395-405 (2004).

Yamashita et al, CD73 expression and fyn-dependent signaling on murine lymphocytes, *Eur. J. Immunol.*, 28:2981-90 (1998).

Yang et al, The A2b adenosine receptor protects against vascular injury, *PNAS*, 105(2):792-6 (2008).

Yegutkin et al, Extracellular ATP formation on vascular endothelial cells is mediated by ecto-nucleotide kinase activities via phosphotransfer reactions, *FASEB J.*, 15:251-60 (2001).

Zernecke et al, CD73/Ecto-5'-Nucleotidase Protects Against Vascular Inflammation and Neointima Formation, *Circulation*, 113:2120-7 (2006).

\* cited by examiner

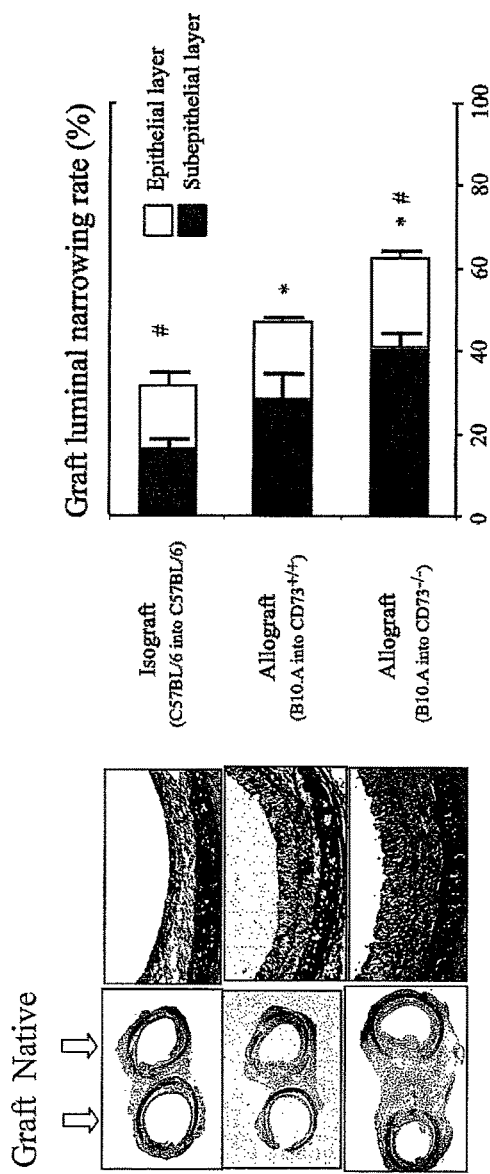
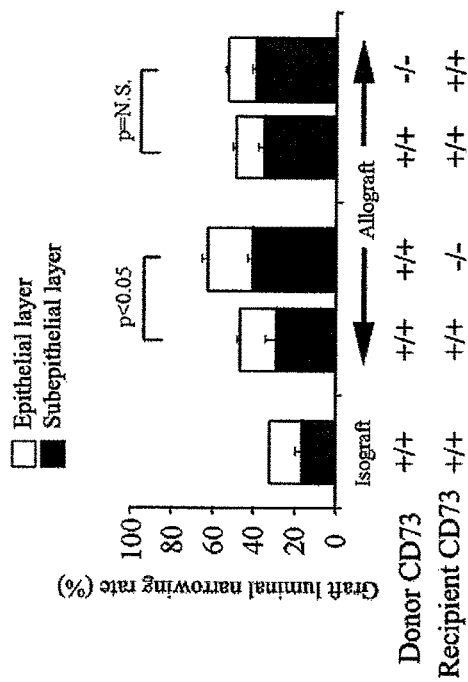
Fig. 1A
Fig. 1B

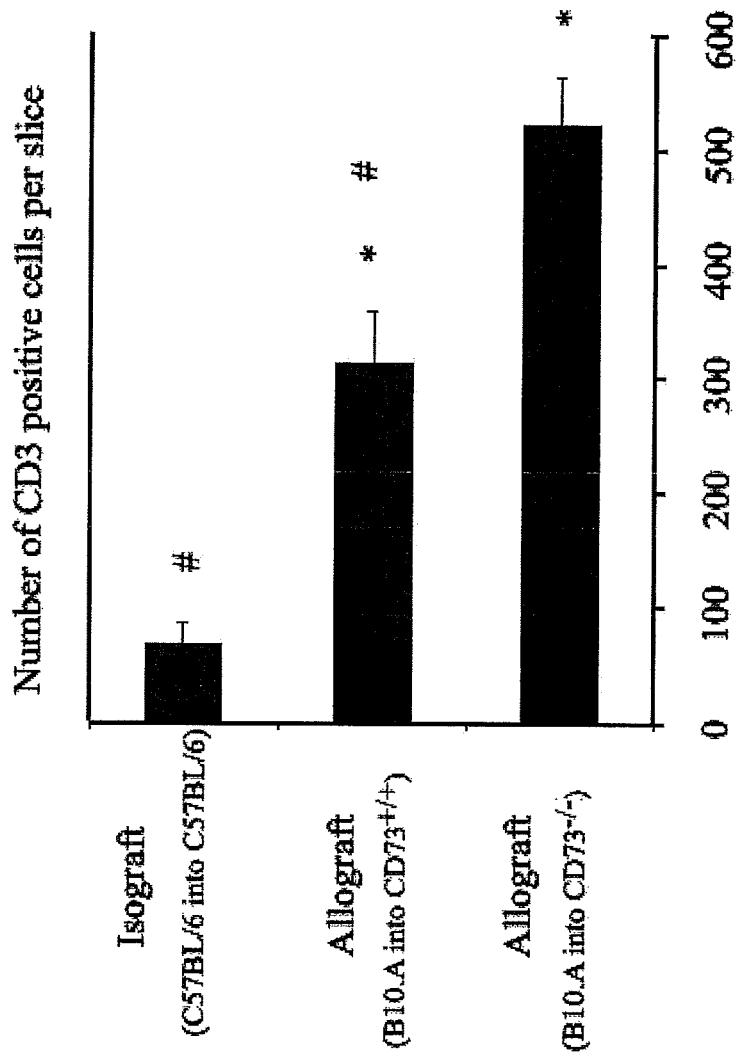

Fig. 6C
Vehicle
A2A agonist
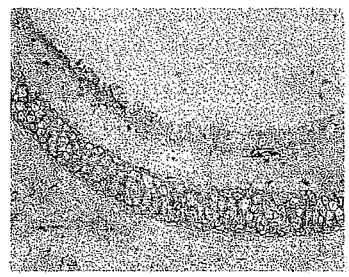

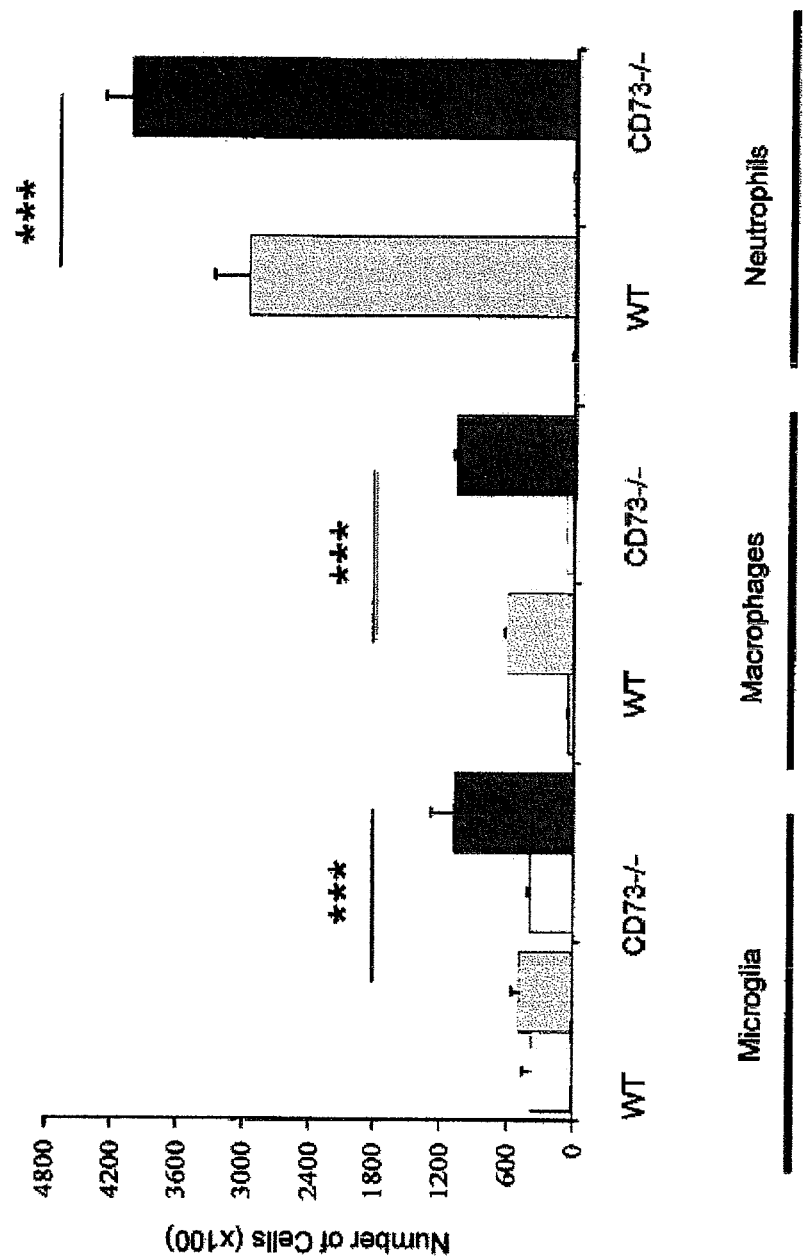

NUCLEOTIDE PHOSPHATE DISSIPATION AS A TREATMENT FOR VASCULAR DISORDERS

This application is a continuation of U.S. application Ser. No. 12/261,870, filed Oct. 30, 2008, which claims the benefit of priority of U.S. provisional applications 60/983,649, filed Oct. 30, 2007, and 60/985,106, filed Nov. 2, 2007.

STATEMENT REGARDING FEDERALLY SPONSORED RESEARCH OR DEVELOPMENT

This invention was made with government support under Grant No. HL086676 awarded by the National Institutes of Health. The government has certain rights in the invention.

SEQUENCE LISTING

The present application is being filed with an electronic format Sequence Listing submitted herewith. The listing is provided as a file entitled SQ0378.txt, created Oct. 30, 2008, and is 19 Kb in size. The entire contents of this electronic format Sequence Listing is hereby incorporated by reference.

FIELD OF THE INVENTION

The invention relates to methods of treating or preventing immunoinflammatory, vascular, thrombotic or ischemic disorders by administering one or more agents which dissipate nucleoside or nucleotide phosphates.

BACKGROUND OF THE INVENTION

Blood vessels possess certain properties which enable them to maintain free flow of nutritive blood, oxygen, fluids, and dissolved substances to tissues. Among the properties which blood vessels regulate are those which control (either promote or inhibit) coagulation, vasodilation, inflammation, proliferation, and barrier function. Endothelial cells, as well as other cells of the vascular wall, have a number of intrinsic properties that enable them to modulate these key vascular homeostatic properties in an active manner under quiescent conditions. Under disease nonhomeostatic or pathologic conditions, such as ischemia, surgery, autoimmunity; immobilization, trauma, transplantation, or vascular interventions, these intrinsic homeostatic mechanisms may be disrupted. Nucleotidases are specific enzymes which cleave the phosphate group of nucleotide mono, di, or triphosphates, to dissipate the nucleotide tri/di/monophosphate and generate a nucleotide free of some or all of its phosphate groups. As cells possess receptors through which nucleotide phosphates interact, as well as receptors for the dephosphorylated nucleotide, the dissipation of these chemicals can alter cellular properties. Furthermore, in the dissipation process, generation of less phosphorylated (or unphosphorylated) nucleotides can exert similar or disparate signals in cells. Two key ectonucleotidases are found in cells comprising the vascular wall, including CD39 (which catalyzes the terminal phosphohydrolysis of ATP to ADP, and ADP to AMP) and CD39-like molecules, and CD73 (a 5' nucleotidase), which catalyzes the terminal phosphohydrolysis of AMP to adenosine. As cells undergoing necrosis or cells which are activated release ATP, ADP, or AMP into the intravascular milieu, dissipation of these releasates is critical for maintenance of homeostatic conditions. In addition, generation of adenosine can itself trigger signaling cascades which dampen inflammation and mediate vasodilation. In the settings in which these ectonucleotidases are insufficiently active, inflammation, thrombosis, edema, and apoptosis can result.

These concepts are relevant to a number of pathological states. These include ischemic disorders, such as myocardial infarction, stroke, transient ischemic attacks, ischemia of the liver, gastrointestinal tract, kidneys, limbs, or lungs. Ectonucleotidases are also likely to be important in the setting of atherosclerosis, and endovascular interventions, organ or cellular transplantation, vascular surgery, or cardiac surgery, all conditions where blood flow, the native cell milieu, or vessels are perturbed. As an example of this, myocardial infarction is the leading cause of death in the Western world, and stroke is the third leading cause of death and the main cause of permanent morbidity in the United States, affecting over 450,000 patients annually. CD73 is an ectonucleotidase, meaning, it catalyzes the phosphohydrolysis of extracellular nucleotides. It is an endogenous molecule, which limits inflammation, coagulation, and edema. By inhibiting the infiltration of macrophages and other specific leukocyte populations into ischemic areas or inflammatory sites, damage to tissue in these areas or sites can be limited.

SUMMARY OF THE INVENTION

The present invention is related to methods of treating or preventing immunoinflammatory, vascular, thrombotic or ischemic disorders in, a subject by administering an agent which dissipates nucleotide phosphates (nucleotide mono, di, or triphosphates), as well as an agent which may act by increasing adenosine levels. Protective actions may be conferred by inhibiting macrophage infiltration into a site, promoting vasodilation, limiting apoptosis, reducing edema, or interfering with coagulation, or other mechanisms which restore vascular homeostasis. The subject invention comprises administering to the subject an effective amount of CD73 or nucleotidase, a fragment a mutant, or a modified form thereof. The present invention also provides a method for inhibiting macrophage infiltration into a site in a subject which comprises administering to the subject a compound capable of increasing endogenous CD73 levels. Furthermore, this invention reveals that cyclic AMP or other second messenger stimulating pathways (such as cGMP analogues, nitic oxide or its donors or carbon monoxide or its donors, or phosphodiesterase inhibitors) which raise nucleotidase levels can be protective against ischemic, inflammatory, vascular, or atherosclerotic disorders which may include any of the conditions listed above.

More particularly, the invention provides a method of treating or preventing a vascular, thrombotic, ischemic, or immunoinflammatory disorder in a subject, the method comprising administering to the subject a composition comprising an effective amount of one or more agents which dissipate nucleotide monophosphate; with the proviso that when said composition comprises only one agent that dissipates nucleotide monophosphate, and said only one agent is soluble CD73, said disorder is not acute myocardial infarction or renal ischemia. Specific embodiments of the invention include utilization of CD73 as an agent that dissipates nucleotide monophosphate.

The invention further provides a method of treating or preventing a thrombotic, ischemic, or immunoinflammatory disorder in a subject by inhibiting leukocyte infiltration into a site of said disorder in the subject which comprises administering to the subject a composition comprising an effective amount of CD73, a fragment a mutant, or a modified form thereof.

The invention also provides a method for inhibiting leukocyte infiltration into a site in a subject which comprises administering to the subject a composition comprising a compound that increases endogenous CD73 levels in said subject by said administration.

In other particular embodiments of the invention, the disorders that can be treated or prevented by the inventive methods are; cerebrovascular ischemia, graft rejection in recipient of a heart transplant, and graft rejection in recipient of a lung transplant, liver, kidney, skin, or pancreas transplant.

The inventive methods are useful for preventing or treating one or more of the disorders disclosed herein by utilizing the inventive methods.

BRIEF DESCRIPTION OF THE DRAWINGS

FIG. 1A-1B: The effect of CD73 on graft luminal narrowing 1 week after surgery. (A) Representative Van Gieson staining of tracheal sections for the indicated conditions 1 week after transplantation (low magnification of both graft and native trachea, ×100; high magnification of graft, ×400). The graft luminal occlusion rate demonstrates that allografts in CD73$^{-/-}$ recipients exhibited significantly increased luminal obliteration compared with allografts in wild type recipients (*$p<0.05$ vs. WT allograft; #$p<0.05$ vs. isograft). (B) Effect of epithelial versus infiltrating cell-derived CD73 on graft luminal occlusion. Genotype of donors and recipients were either CD73$^{+/+}$ or CD73$^{-/-}$, as indicated. Data represent analysis of at least 4 transplantations per group. N.S., Not significant.

FIG. 2A-2B: Quantification of graft CD3 positive T cell infiltration. (A) Representative immunohistochemical staining for the pan-T cell marker CD3 in sections of graft for the indicated conditions. Magnification is ×400. (B) Quantitative analysis of T cell infiltration by counting the number of CD3 positive cells under high power magnified fields. Total CD3 positive cell counts were obtained for an entire section taken from the middle one-third of the tracheal graft. CD73-/- allografts demonstrated significantly increased infiltration of T cells compared with wild type allografts (number of cell in epithelial and subepithelial layer per slice; 313±43 vs. 520±41, n=4, $p=0.013$).). In isografts, the number of CD3 positive cell was 67±18 ($p=0.002$ vs. wild type allograft). Each bar represents mean±SEM. (*$p<0.05$, #$p<0.01$).

FIGS. 6A, 6B, and 6 C: (A) The graft luminal occlusion rate demonstrates that allografts injected twice daily (intraperitoneally) with an A2A agonist exhibited significantly reduced luminal obliteration compared with wild type allografts treated with vehicle. (B) Quantitative analysis of T cell infiltration by counting the number of CD3 positive cells under high power magnified fields. Each bar represents the mean of 6 experiments±SEM. (C) Representative immunohistochemical staining for CD3 in sections of graft for the indicated conditions (×400).

FIGS. 16A, 16B, and 16C: Role of CD73 in leukocyte sequestration in the ischemic brain 48 hrs after MCA (middle cerebral arterial) occlusion: A) Absolute number of leukocyte subpopulations ie microglia, macrophages and neutrophils in contralateral and ischemic hemispheres in WT and CD73 null mice; n=6 for each group; Values are mean±SEM *P<0.001). B and C) Relative contribution of microglia, macrophages and neutrophils in contralateral and ischemic hemispheres in WT and CD73 null mice 48 hrs after induction of brain ischemia; n=6 for each group; *P<0.001).

DETAILED DESCRIPTION OF THE INVENTION

Figure 3A:
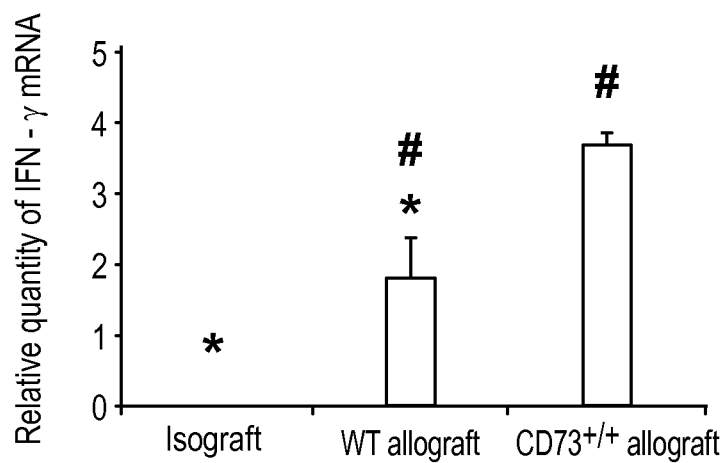
FIG. 3A-3B: Quantitative analysis of T-helper 1-type cytokines interferon (IFN)-γ (A) and interleukin (IL)-2 (B) mRNA extracted from trachea of isografts, wild type allografts and CD73$^{-/-}$ allografts (n=4, each). Significantly higher expression of IFN-γ and IL-2 was observed in trachea from CD73$^{-/-}$ allografts compared with trachea from wild type allografts. Data are presented as the fold induction of mRNA to β-actin. *$p<0.05$ vs. isograts. #$p<0.05$ vs wild type allografts.

The present invention provides a method of treating or preventing vascular, thrombotic or ischemic disorders in a subject, the method comprises administering to the subject an agent which dissipates nucleotide mono, di, or triphosphates.

In one embodiment of the method, the agent is soluble CD73 polypeptide, soluble CD39 polypeptide, or a mutated or a modified form of CD73 or CD39.

In another embodiment of the method, the active fragment is soluble CD73.

In one embodiment of the method, the CD73 polypeptide or its active fragment treats or prevents vascular, thrombotic or ischemic disorders in a subject without increasing bleeding or intracerebral hemorrhage.

In another embodiment of the method, the agent is a catalytic antibody which mimics the action of CD39 or CD73.

In a particular embodiment, the invention provides a method of treating or preventing a vascular, thrombotic, ischemic, or immunoinflammatory disorder in a subject, the method comprising administering to the subject a composition comprising an effective amount of one or more agents which dissipate nucleotide monophosphate; with the proviso that when said composition comprises only one agent that dissipates nucleotide monophosphate, and said only one agent is soluble CD73, said disorder is not acute myocardial infarction or renal ischemia.

In one embodiment, the one or more agent is CD73, or a fragment, a mutant, or modified form thereof.

In another, the one or more agent is a catalytic antibody which mimics the action of CD73.

In another, the disorder is cerebrovascular ischemia.

In another, the subject is recipient of a heart transplant and said disorder is graft rejection.

In another, the subject is recipient of a lung transplant and said disorder is graft rejection.

In another, the subject is recipient of a heart transplant and said disorder is graft vasculopathy.

In another, the agent is a polypeptide selected from the group consisting of:
  a) CD73 polypeptide from *Crotalus atrox* venom;
  b) CD73 polypeptide set forth in SEQ ID NO: 1,
  c) CD73 polypeptide set forth in SEQ ID NO: 3, and
  d) a fragment, a mutant, or modified form of a CD73 polypeptide set forth in a), b), or c).

In another, the composition comprises a polypeptide selected from the group consisting of:

a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises at least one $A_2A$ receptor agonist.

In another, the composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises at least one $A_{2B}AR$ receptor agonist.

In another, the composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises and at least one $A_2A$ receptor agonist; and wherein said composition is a pharmaceutical composition further comprising a pharmaceutically acceptable carrier.

In another, the composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO 3, and
d) a fragment, a mutant, or modified form of a CD73 polypeptide set forth in a), b), or c);

and further comprises at least one agent selected from an $A_{2B}AR$ receptor agonist; and wherein said composition is a pharmaceutical composition further comprising a pharmaceutically acceptable carrier.

In another, the composition composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises at least one $A_2A$ receptor agonist; and wherein said subject is recipient of a lung transplant and said disorder is graft rejection In another, the composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises at least one $A_{2B}AR$ receptor agonist; and wherein said subject is recipient of a heart transplant and said disorder is graft rejection.

In another, the composition comprises a polypeptide selected from the group consisting of:
a) CD73 polypeptide from *Crotalus atrox* venom;
b) CD73 polypeptide set forth in SEQ ID NO: 1,
c) CD73 polypeptide set forth in SEQ ID NO: 3, and
d) a fragment, a mutant, or modified form of a CD73 polypeptide set forth in a), b), or c);

and further comprises at least one $A_{2B}AR$ receptor agonist; and wherein said subject is recipient of a heart transplant and said disorder is graft vasculopathy.

In another particular embodiment, the invention provides a method of treating or preventing a thrombotic, ischemic, or immunoinflammatory disorder in a subject by inhibiting leukocyte infiltration into a site of said disorder in the subject which comprises administering to the subject a composition comprising an effective amount of CD73, a fragment, a mutant, or a modified form thereof. In one embodiment, the leukocyte is a macrophage.

In another particular embodiment, the invention provides a method for inhibiting leukocyte infiltration into a site in a subject which comprises administering to the subject a composition comprising a compound that increases endogenous CD73 levels in said subject by said administration. In one embodiment, the leukocyte is a macrophage.

As used herein, the term "AMP" means adenosine monophosphate.

As used herein, "ischemic and thrombotic disorders" encompass pulmonary embolism, lung ischemia, limb or gut ischemia, myocardial ischemia, post surgical vasculopathy, postangioplasty stenosis, shunt/fistula remodeling or thrombosis, cerebral ischemia, or ischemia of the other organs or tissues.

As used herein, the term "ischemic disorder" encompasses and is not limited to a peripheral vascular disorder, a venous thrombosis, a pulmonary embolus, a myocardial infarction, a transient ischemic attack, lung ischemia, unstable angina, a reversible ischemic neurological deficit, adjunct thromolytic activity, excessive clotting conditions, reperfusion injury, sickle cell anemia, a condition wherein blood flow is interrupted or altered during surgery, a stroke disorder or an iatrogenically induced ischemic period such as angioplasty. For the purposes of the invention, stroke disorder includes cerebrovascular ischemia.

As used herein, the term "thrombotic disorder" encompasses disorders caused by the formation, development or presence of a blood clot or a blood coagulation which is located inside of a patient or inside of an extracorporeal circuit or system which circulates blood of the patient. Thrombotic disorder also encompasses disorders caused by the presence of a thrombus which includes a blood clot partially or fully occluding a blood vessel or formed in a heart cavity or by the activation of a plasmatic coagulation system in a patient which includes the production of fibrin, meshed platelets, fibrin degradation product, protein C, free protein S, coagulation factor II, immunoglobulin G or albumin in the patient. Thrombotic disorder also encompasses disorders caused by the formation of white thrombus which may be composed of platelets and fibrin and is relatively poor in erythrocytes, a disseminated fibrin deposit thrombus or a red thrombus which may be composed of red cells and fibrin.

As used herein, an "immunoinflammatory disorder" includes graft rejection in an organ transplant recipient.

The expression "effective amount" is meant to include any amount of an agent according to the present invention that is sufficient to bring about a desired therapeutical result, especially upon administration to an animal or human subject.

The expression "elevated level of CD73" shall be interpreted as a level that is at least 2% higher, preferably at least 20% higher, most preferably at least 30% higher than the normal tissue level would be without the measures taken according to this invention. An elevated level of CD73 may be measured by an increase in local or circulating level of adenosine, or by an elevated level of AMP-dissipating activity. All agents described for administration according to the methods of the invention; including CD73 polypeptides, fragments, mutants, variants, and modified forms thereof are encompassed for such administration, so long as the administration brings about an elevated level of CD73.

Human placental 5'-nucleotidase is initially synthesized as a precursor (574 residues) with the NH2-terminal signal peptide, cotranslationally processed to an intermediate form (548 residues) containing the hydrophobic domain at the COOH terminus, and finally converted to a mature form (523 residues) by proteolytic removal of the COOH-terminal signal and by simultaneous replacement with glycosyl-PtdIns, which functions as the membrane anchor of the mature molecule. Eur. J. Biochem. 191, 563-569 (1990). Soluble CD73 is made recombinantly by deletion of the membrane anchor domain, and is suitable for administration to a subject. Nucleotides suitable for such use include those set forth in SEQ ID NO's: 2 and 4, and those nucleotides encoding polypeptide s having at least 46%, 50%, 55%, 60%, 65%, 70%, 75%, 80%, 85%, 90%, 91%, 92%, 93%, 94%, 95%, 96%, 97%, 98%, or 99% similarity or identity to the CD73 polypeptides set forth in SEQ ID NO's: 1 and 3.

CD73 polypeptide set forth in SEQ ID NO: 1 and/or 3, or other known ecto-5' nucleotidases are also suitable for administration to a subject by formulation in cell for therapeutic delivery, in a micelle, or nanoparticle. 45.9% similarity is is observed between the CD73 polypeptides set forth in SEQ ID NO's: 1 and 3. Thus, the methods of the invention encompass utilizing a CD73 polypeptide that is at least 46%, 50%, 55%, 60%, 65%, 70%, 75%, 80%, 85%, 90%, 91%, 92%, 93%, 94%, 95%, 96%, 97%, 98%, or 99% similar or identical to the CD73 polypeptides set forth in SEQ ID NO's: 1 and 3.

In particular embodiments, the methods of the invention encompass utilizing a CD73 polypeptide that is at least 46%, 50%, 55%, 60%, 65%, 70%, 75%, 80%, 85%, 90%, 91%, 92%, 93%, 94%, 95%, 96%, 97%, 98%, or 99% similar or identical to the CD73 polypeptides set forth in SEQ ID NO's: 1 and 3; so long as the administration of the polypeptide according to the inventive method brings about an elevated level of CD73 or its activity.

All similarity and identity percentages recited herein are inclusive of all numerical values, including whole integers and decimals, between the stated percentages and inclusive of the endpoints.

In another embodiment of the method, the CD73 polypeptide or its active fragment can be replaced by a peptide, an enzyme, a pseudo enzyme, a catalyst, a peptidomimetic compound, a glycosylated peptide, a small molecule, a mutated peptide or an antibody.

As used herein, a polypeptide is an amino acid polymer of amino acids linked together by peptide bonds; a nucleic acid is a deoxyribonucleotide or ribonucleotide polymer of nucleotides linked together by phosphodiester bonds; an antisense nucleic acid is a nucleic acid that is the reverse complement of another nucleic acid which may be capable of inhibiting transcription or translation of the other nucleic acid.

In another embodiment of the method, the CD73 polypeptide or its active fragment agent comprises a CD73 polypeptide (abbreviated as CD73) or a variant thereof.

Variants in amino acid sequence of CD73 are produced when one or more amino acids in naturally occurring CD73 is substituted with a different natural amino acid, an amino acid derivative, a synthetic amino acid, an amino acid analog or a non-native amino acid. Particularly preferred variants include homologous CD73 of humans or of different species of animals. Variants of CD73 may include biologically active fragments of naturally occurring CD73 wherein sequences of the variant differ from the wild type CD73 sequence by one or more conservative amino acid substitutions. Such substitutions typically would have minimal influence on the secondary structure and hydrophobic nature of the CD73. The amino acid sequences of CD73 and one variant of CD73 have been previously determined and are known in the art.

Variants may also have sequences which differ by one or more non-conservative amino acid substitutions, deletions or insertions which do not abolish the biological activity associated with CD73. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

A CD73 variant of this invention includes a CD73 varied by changes such as insertions, deletions and substitutions, either conservative or nonconservative where such changes might provide for certain advantages in their use such as increased potency, bioavailability, stability or decreased toxicity or degradation under physiological conditions.

In other embodiments, variants with amino acid substitutions which are less conservative may also result in desired derivatives of CD73, e.g., by causing desirable changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Just as it is possible to replace substituents of the scaffold (i.e., amino acids which make up the CD73), it is also possible to substitute functional groups which decorate the scaffold with groups characterized by similar features (i.e., R-groups which are part of each amino acid). These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring CD73, as well as changes in acetylation, methylation, phosphorylation, carboxylation or glycosylation.

In a further embodiment the CD73 is modified by chemical modifications in which activity is preserved. For example, the CD73 may be aminated, sulfated, singly or multiply halogenated, alkylated, carboxylated, or phosphorylated. The CD73 may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of CD73, for example the methionine sulfone and methionine sulfoxide analogs. The invention also includes salts of CD73, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Variants of CD73 may also include peptidomimetic compounds of CD73. Such compounds are well known to those of skill in the art and are produced through the substitution of certain R groups or amino acids in the protein with non-natural replacements. Such substitutions may increase the stability, bioavailability, or activity of such CD73 compound.

In another embodiment of the method, the CD73 polypeptide or its active fragment can be replaced by a nucleic acid encoding CD73 or its variants or a biologically active fragment thereof.

In another embodiment of the method, the stroke is associated with other conditions such as hypertension, pulmonary embolism, deep venous thrombosis, post surgical vasculopathy, postangioplasty stenosis, and shunt/fistula remodeling or thrombosis.

In another embodiment of the method, the stroke is associated with lung ischemia, limb ischemia, gut ischemia, myocardial ischemia.

In another embodiment, the disorder is selected from hypertension, pulmonary hypertension, pulmonary embolism, deep venous thrombosis, post-stent or post angioplasty stenosis, shunt/fistula remodeling or thrombosis, lung, limb, gut, kidney, and myocardial ischemia.

In another embodiment, the time of administration comprises from about 5 days before surgery or onset of the disorder to about 5 days after surgery or the onset of the disorder. In another embodiment, the period of time comprises from about 1 hour before surgery or the onset of the disorder to about 12 hours after surgery or the onset of the disorder. In another embodiment, the period of time comprises from about 12 hours before surgery or the onset of the disorder to about 1 hour after surgery or the onset of the disorder. In another embodiment, the period of time comprises from about 1 hour before surgery or the onset of the disorder to about 1 hour after surgery or the onset of the disorder. In another embodiment, the administration occurs after the onset of the disorder and at permanent regular intervals thereafter.

In one embodiment, the subject is a mammal. In another embodiment, the mammal is a human. In another embodiment, the amount of CD73 polypeptide or its active fragment administered comprises from about 75 .mu.g/kg to about 550 .mu.g/kg. In another embodiment, the amount comprises 300 .mu.g/kg.

In another embodiment of the method, the administration of the CD73 polypeptide or its active fragment occurs at the onset of stroke in a subject. In another embodiment of the method, the administration of the CD73 polypeptide or its active fragment is prior to stroke onset in a subject.

In another embodiment of the method, the administration of the CD73 polypeptide or its active fragment occurs after the stroke onset in a subject.

In another embodiment of the method, the CD73 polypeptide or its active fragment is administered in a dosage of 1-20 mg/kg of the subject's body weight.

In another embodiment of the method, the CD73 polypeptide or its active fragment is administered in a dosage of 4-8 mg/kg of the subject's body weight.

In another embodiment of the method, the subject is a mouse, a rat, a dog, a primate or a human.

In a further embodiment of the method, the CD73 polypeptide or its active fragment is administered with a pharmaceutically acceptable carrier.

As used herein, the term "pharmaceutically acceptable carrier" encompasses any of the standard pharmaceutically acceptable carriers, such as phosphate buffered saline solution, water, emulsions such as oil/water emulsion or a triglyceride emulsion, various types of wetting agents, tablets, coated tablets and capsules. Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients.

By means of well-known techniques such as titration and by taking into account the observed pharmacokinetic characteristics of the agent in the individual subject, a skilled artisan can determine the appropriate dosages for treatment methods of the present invention.

Mutants or fragments of CD73 can be produced by known genetic engineering techniques, using as the starting material recombinant cDNA encoding CD73 in an appropriate cloning vector or using direct chemical synthesis.

The present invention also provides a method for inhibiting macrophage infiltration into a site in a subject which comprises administering to the subject a compound capable of increasing endogenous CD73 levels.

Although an elevated level of CD73 in an individual can be induced by administering the recombinant CD73 protein, or by a cytokine or another factor capable of inducing endothelial CD73 expression or by a combination of both therapies, the use of a cytokine or another factor with similar capability in many cases would be preferable. However, in serious traumas administration of recombinant CD73 protein would be useful, in order to rapidly achieve an increased adenosine production, as an alternative or as an additional therapy.

Suitable agents to be used in this invention include cytokines or other factors that directly or indirectly upregulate transcription of the CD73 gene. A suitable cytokine for use in this invention is typically an interferon or an interleukin, but also other agents may be used. In case the cytokine is an interferon, the interferon may be alpha-, beta-, gamma-, omega-, or any other interferon and it can by any subtype of the aforementioned interferons. It is believed that particularly alpha-, beta-, and gamma-interferons are suitable for use in this invention.

Any interleukin capable of inducing endothelial CD73 expression is also suitable for use in this invention. As examples of such interleukins can be mentioned IL-2, IL-4, IL-10, IL-13 and IL-20.

Initial data from our laboratory show that animals which lack ectonucleotidases (either CD39 or CD73) have worse outcomes in the setting of stroke, as well as exacerbated atherosclerosis in the setting of hyperlipidemia. As described in further detail below, the particular embodiments of the inventive methods described herein are premised on discovering protective roles for CD73 in heart transplantation, lung transplantation, atherosclerosis, and cerebrovascular ischemia.

CD73 Attenuates Allograft Airway Rejection

Particular embodiments of the inventive methods described herein are drawn to preventing or treating graft rejection in a lung transplant recipient. Lung transplantation has become an acceptable therapy for the treatment of end-stage pulmonary diseases. However, allograft rejection remains a major cause of morbidity and mortality in lung transplant patients (Estenne, et al, *Am J Respir Crit Care*

*Med* 166:440444, 2002; Estenne, et al, *J Heart Lung Transplant* 21:2970310, 2002). Bronchiolitis obliterans (BO), and its clinical correlate bronchiolitis obliterans syndrome (BOS), affect up to 50-60% of patients who survive 5 years after lung (Boehler, et al, *Chest* 114:1411-1426, 1998; Estenne, et al, *Am J Respir Crit Care Med* 166:440444, 2002; Estenne, et al, *J Heart Lung Transplant* 21:2970310, 2002). BO is characterized by progressive obliteration of the small airways with major pathological features including lymphocytic infiltration in early stages, inflammation, epithelial cell injury, and ultimately fibrosis (Yousem, et al, *J Heart Lung Transplant* 15:1-15, 1996). Although the introduction of potent immunosuppressive agents has improved the early graft survival, repeated acute rejection results in BO, which is the main factor that limits long-term survival (Trulock, E. P., *Am J Respir Crit Care Med* 155; 789-818, 1997).

To elucidate a potential mechanistic link between CD73 and airway rejection, an orthotopic and heterotopic trachea transplantation model was employed using CD73 null mice. Experiments were done with special reference to epithelial cell injury and inflammation. These are the main pathological features of lymphocytic bronchitis (LB), which is believed to be a harbinger of BO. The importance of LB is underscored by the fact that it is a reversible inflammatory process that leads to irreversible BO. Conceivably, understanding LB contributory mechanism could lead to new therapeutic options to prevent BO. As data presented herein indicate that CD73 contributes to epithelial injury, LB, and loss of airway lumen, it could become a new target of therapeutic opportunity to prevent BO.

Lung transplantation remains the only effective therapy for the large number of patients with end-stage lung disease (DeMeo, et al, *Transplantation* 72:1713-1724, 2001; Trulock, E. P., *Am J Respir Crit Care Med* 155:789-818, 1997). However, despite advances in immunosuppressive therapies and surgical techniques, overall 5-year survival rate remains 50% (Trulock, et al, *J Heart Lung Transplant* 26: 782-795, 2007). Mortality after lung transplantation results mainly from the development of chronic graft dysfunction from BO, which develops in >60% of lung transplant recipients (Boehler, et al, *Chest* 114:1411-1426, 1998; Estenne, et al, *Am J Respir Crit Care Med* 166:440-444, 2002; Estenne, et al, *J Heart Lung Transplant* 21: 297-310, 2002). Clinical studies have implicated acute rejection as the major causative factor for the development of BO (Heng, et al, *J Heart Lung Transplant* 17: 1255-1263, 1998; Trulock, E. P., *Am J Respir Crit Care Med* 155: 789-818, 1997), and T lymphocytes play an important role in the pathogenesis (Higuchi, et al, *Transplantation* 74: 646-651, 2002; Higuchi, et al, *J Immunol* 174: 1871-1878, 2005).

The data disclosed herein demonstrates that disruption of CD73 leads to increased graft luminal occlusion and T cell infiltration into the airway graft tissue.

To ascertain the relative contribution of airway epithelial CD73 expression vs. CD73 expression in recipient graft-infiltrating leukocytes, histological differences between CD73$^{-/-}$ donor tissue transplanted into WT recipients and tissue transplanting in the reciprocal combination (WT airway grafts into allogenic CD73$^{-/-}$ recipients) were histologically evaluated. Results demonstrated significantly increased allograft luminal narrowing when the recipients lacked the CD73 gene, implicating a critical contribution of recipient graft-infiltrating leukocytes-derived CD73, rather than epithelium derived CD73, in exacerbating of airway rejection.

Based on the data disclosed herein, depletion of CD73 in recipient caused increase of Th1-dominated cytokine (IFN-γ and IL-2) mRNA expression compared with wild type recipient. The data also demonstrates that A2A receptor agonist reduced graft luminal occlusion and T cell infiltration into the airway graft tissue in both WT and CD73 null mice. It also shows A2A receptor agonist attenuated the production of IFN-γ and IL-2. It is known that adenosine has various immunoregulatory activities mediated through four adenosine receptors: A1, A2A, A2B, and A3; and that T lymphocytes mainly express the high affinity A2A receptor and the low-affinity A2B receptor. A2A receptors are present on T cells and regulate many lymphocytic functions (Huang, et al, *Blood* 90: 1600-1610, 1997; Koshiba, et al, *J. Biol Chem* 272: 25881-25889, 1997; Thiel, et al, *Microbes Infect* 5: 515-526, 2003). In particular embodiments, the invention is directed to the discovery that A2A activation significantly ameliorated lymphocyte-mediated immune responses in wild type allograft and CD73 null allograft. This was clearly shown by the dramatic improvement of T lymphocyte infiltration, a model that bears remarkable clinical, pathologic, and immunologic similarity to LB. Although the exact mechanisms of action for CGS-21680 remain unknown, the data disclosed herein suggests that A2A receptor activation interferes with lymphocytic function during acute rejection and may exert anti-inflammatory effects, in part by suppressing cytokine secretion. The data also demonstrates that activation of A2A receptor with CGS-21680 attenuated cytokine release and acute rejection in airway transplant model. Taken together, and based on the data disclosed herein, particular embodiments of the invention are drawn to CD73 and A2A receptor as additional therapeutic targets.

CD73 Mediates Adenosine Generation and Signaling in Murine Cardiac Allograft Vasculopathy Particular embodiments of the inventive methods described herein are drawn to preventing or treating graft rejection in solid organ transplant recipient. Such a recipient could be a heart transplant recipient. Biological actions of CD73 might occur either through dissipation of AMP, or via the generation of adenosine which has its own downstream set of signaling receptor subtypes. These adenosine receptors (ARs) include $A_1AR$, $A_{2A}AR$, $A_{2B}AR$ and $A_3AR$, with each receptor having a unique tissue distribution, ligand affinity and signal transduction pathway. The $A_1AR$ and $A_3AR$ inhibit adenylyl cyclase, whereas the $A_{2A}AR$ and $A_{2B}AR$ stimulate this effector system and therefore cAMP production (Olah, et al, *Annu Rev Pharmacol Toxicol* 35: 581-606, 1995). Little is known about the contribution of each subtype receptor to the events surrounding cardiac transplantation.

In the current work, studies examined the role of CD73 on development of cardiac allograft vasculopathy (CAV), the major impediment to the long-term survival of human cardiac allografts. CAV is a rapidly progressive form of atherosclerosis that often leads to reduced blood flow and ischemia of distal tissues. Histologically, CAV is identified by a combination of proliferative myoblasts, macrophages and T lymphocytes leading to the formation of a neointima. The mechanism for CAV development is considered to be multifactorial, and likely includes both immunologic and non-immunologic triggers[13]. CD73, which sits at an interface position between immune modulator and vascular homeostatic mediator, is an excellent target to consider for involvement in (or protection against) CAV development. Although intimal proliferation mechanisms may differ, a recent study has shown that vascular neointimal formation is increased in CD73-deficient mice after carotid artery injury.

In contrast, reconstitution of wild-type mice with CD73-deficient bone marrow did not exacerbate neointimal formation in the artery injury model, indicating that CD73 produced by resident non-hematopoietic cells, rather than by circulating cells, plays an active role in mitigating neointimal hyperplasia (Zernecke, et al, *Circulation* 113: 2120-2127, 2006). However, as CD73 is expressed by leukocytes as well as by tissue-resident cells including endothelial cells, we hypothesized that CD73 expressed on both local and circulating cells could contribute to preserving vascular homeostasis after cardiac transplantation, at least in part by modulating the transit of leukocytes across inflamed endothelium (Airas, et al, *J Exp Med* 182: 1603-1608, 1995).

CD73 effects the terminal phosphohydrolysis of AMP, which in turn generates adenosine. In the present experiments, the use of CD73$^{-/-}$ mice as either donors or recipients of heterotopic cardiac allografts allowed us to demonstrate the critical roles that CD73 plays in allograft survival and CAV prevention. Comparisons of CD73$^{-/-}$ mice to CD73$^{+/+}$ mice showed there to be less rejection and diminished vasculopathy when CD73 was present. These experiments indicate that CD73 promotes graft barrier function, suppresses the inflammatory response, and dampens alloeffector immune responses including the trafficking of leukocytes across allogeneic endothelium. Though these results could be attributed to the dissipation by CD73 of AMP, it is also quite likely that generation of adenosine as a byproduct of AMP phosphohydrolysis could participate in these salutary vascular effects.

CD73 contributes in a major way to local adenosine concentrations especially at the vascular intimal surface where it is generated. Adenosine in the local vascular microenvironment is known to suppress inflammation, promote vasodilation, and inhibit vascular leakage, each action dependent upon the receptor subtype to which it predominantly binds Use of specific adenosine receptor agonists and antagonists in the experiments set forth below allow us to conclude that the predominant vascular effects of CD73 in murine cardiac allotransplantation are mediated via the $A_{2B}AR$. When an $A_{2A}AR$ agonist was given to recipients, graft survival was slightly prolonged (ie, rejection diminished) regardless of CD73 genotype. Interestingly, we have shown that intragraft $A_{2A}$ AR mRNA expression was significantly down-regulated, possibly suggesting that it might have less involvement in neointimal formation after cardiac allotransplantation. When an $A_{2B}AR$ agonist was given to recipients, graft survival was markedly prolonged (ie, rejection diminished) regardless of CD73 genotype. These acute rejection experiments, indicating a dominant immune suppressive role mediated via the $A_{2B}AR$, led us to investigate the effects of chronic $A_{2B}AR$ stimulation on development of CAV. Chronic $A_{2B}AR$ stimulation resulted in a marked suppression of CAV development, and this rescue occurred regardless of whether CD73 was itself absent from the donor or recipient genotype. Taken together, these data disclosed herein clearly demonstrate an anti-rejection and anti-CAV role for CD73, which is likely to be mediated proximately by the local generation of adenosine and its actions predominantly via the $A_{2B}AR$.

Furthermore, as shown in the EXAMPLES described herein, a lack of CD73 in donors or recipients attenuated $A_{2B}AR$ expression and promoted an inflammatory cascade involving enhanced graft permeability, neutrophil infiltration and subsequent MPO release in cardiac allografts during the I/R phase. We also observed a positive correlation between CD73 and $A_{2B}AR$ mRNA expression in cardiac allografts at 4 hours after transplantation (data not shown). $A_{2B}AR$ expression in cardiac allografts is still upregulated in the acute rejection phase, and to a lesser degree in the I/R phase in CD73-deficient transplantations. It has been reported recently that inflammatory cytokines such as IL-1, TNF-α and IFN-γ modulate $A_{2B}AR$ expression and function on microvascular endothelial cells (Nguyen, et al, *J Immunol* 171: 3991-3998, 1991), and that the $A_{2B}AR$ protects against vascular lesion formation via regulation of inflammatory cytokines, chemokines and adhesion molecules (Yang, et al, *J Clin Invest* 116: 1913-1923, 2006; Yang, et al, *Proc Natl Acad Aci USA* 105: 792-796, 2008). We have shown here that CD73 expression in donors or recipients plays an important role in regulating those inflammatory factors in the acute rejection phase of cardiac transplantation. Therefore, our results indicate that activation of $A_{2B}AR$ via CD73-generated adenosine modifies the production of inflammatory molecules. Such interactions could be an important mechanism for dampening endothelial activation and the inflammatory response in the acute allograft rejection.

$A_3AR$ expression in cardiac allografts is also upregulated to a greater degree in CD73-deficient transplantation during the acute rejection phase. Interestingly, we observed a negative correlation between CD73 and $A_3AR$ mRNA expression (data not shown). Although much attention has focused on the effects of activating $A_3AR$ in the heart, the role played by $A_3AR$ in apoptosis remains unclear as some studies support a protective role for the receptor while others indicate that it induces myocardial apoptosis (Maddock, et al, *Am J Physiol Heart Circ Physiol* 283: H1307-H1313, 2002; Shneyvays, et al, *Exp Cell Res.* 257: 111-126, 2000). In the present study, CD73 deficiency in donors or recipients promoted apoptosis in cardiac allografts during the acute rejection phase (unpublished data). The effects of $A_3AR$ activation appear to depend upon the pattern of receptor activation (endogenous or exogenous) and drug administration (dose or duration), and we believe that this relationship between CD73 and $A_3AR$ in cardiac transplantation may be explained as a compensatory and protective upregulation of $A_3AR$ in response to apoptosis or to a deficiency of CD73. Further studies are needed to further elucidate this complex relationship.

Little is known about the effects of CD73 expression on the immune system. Our current research supports earlier work which showed that adenosine generated by CD73 on T lymphocytes mediates immune suppression in skin allografts and in vitro experiments (Deaglio, et al, *J Exp Med* 204: 1257-1265, 2007). Using histologic studies, we have demonstrated that CD73 deficiency in donors or recipients correlates with intense acute rejection, as evidenced by impressive graft infiltration of both CD4- and CD8-positive T-lymphocytes in the acute rejection phase following transplantation. IFN-γ, which is known to enhance antigen presentation and promotes cellular immunity by activated macrophages, natural killer (NK) cells, and Th1 lymphocytes, was also significantly upregulated in CD73-deficient cardiac allografts. It is also known that a critical event during the progression of acute allograft rejection is the recruitment and transmigration of alloantigen-primed CD4- and CD8-positive T-lymphocytes into the graft, followed by the release of cytokines by both endothelial cells and T lymphocytes. Our in vitro coculture experiments demonstrated that both genetic deletion and pharmacological blockade of CD73 promote the transendothelial migration of T lymphocytes, and upregulate expression of TNF-α, VCAM-1 and IFN-γ. In addition, the present studies show that CD73 deficiency in donors or recipients resulted in an increase in the production of donor-reactive alloantibodies and T-lymphocyte proliferation in the chronic rejection phase of cardiac transplantation. Taken together, these results indicate that CD73 regulates allogeneic interactions between endothelial cells and T lymphocytes, and thus plays an immunomodulatory role that promotes allograft survival.

T lymphocytes may not be the only effector cells relevant to cardiac allograft rejection which are modulated by CD73. NK cells are a type of cytotoxic lymphocytes which are able to kill targets cells without prior exposure to antigen. Because their lethal effector functions are triggered without prior antigen priming, they are considered to be an integral constitutent cell of the innate immune system, and hence, relevant to cardiac allograft rejection or vasculopathy. It is known that CD73 is indeed expressed by NK cells as well as endothelial cells and other leukocytes. The interaction between NK cells and T cells which contribute to CAV likely involves IFNs and other cytokines. In the present study, we focused on the immunological cross-talk between endothelial cells and T-cells in transplant alloresponses. Though we did not specifically evaluate NK cell activity, these cells could indeed be activated in cardiac allografts because intragraft IFN-γ mRNA expression was upregulated at 7 days post-transplantation. IFN-γ mRNA levels were significantly increased in the allografts in which CD73 was absent in either the implanted graft or the recipient compared with wild-type transplants. Therefore, NK cells in CD73-deficient recipients might contribute to CAV development.

Our study involved both donor (endothelial and parenchymal cells) and recipient (leukocytes) sources of CD73, thus allowing us to explore the contributions that each source makes to the overall transplant milieu. In allotransplant settings, recipient leukocytes attack donor endothelial cells resulting in acute rejection, characterized by endothelial injury and dysfunction, altered endothelial permeability, and neointimal formation (vasculopathy). The alloimmune injury induced by cross-MHC barrier transplantation can be a sustained and severe endothelialitis, which differs from that in mechanical vascular injury (alloeffector mechanisms do not pertain). In general, the alloimmune vascular injury caused by transplantation is quite brisk and severe. This is an important difference when one considers the work by Zernecke et al. (Zernecke, et al, *Circulation* 113: 2120-2127, 2006), in which following carotid wire injury, there was no significant difference in neointimal formation when CD73 null marrow was transplanted into wild-type recipients. Based on knowledge of the effects of CD73 and downstream adenosine and its signaling mechanisms in immune regulation, one could speculate that transplantation of CD73 null marrow might increase allograft vasculopathy. The reasoning behind this hypothesis is that CD73-dependent adenosine generation induces a form of leukocyte-endothelial cell cross-talk that results in reduced leukocyte adhesion to the endothelium and decreased transmigration into tissues in the setting of certain types of inflammatory responses[10]. In the current transplant experiments, there was an opportunity to discern whether there was a local vascular effect of CD73 based on its expression on circulating leukocytes, or whether the effect was due to CD73 present on cells resident in the graft at the time of transplantation. Our data clearly demonstrate that CD73 in either or both locations can play a role in restoring vascular homeostasis to cardiac allografts.

Another recent study has shown that both recipient- and donor-derived cells contribute to the regeneration of damaged cells in cardiac allografts (Jonigk, et al, *Transplantation* 84: 1335-1342, 2007). The interaction between endothelial cells and lymphocytes attenuates CD73 activity (Henttinen, et al, *J Biol Chem* 278: 24888-24895, 2003), whereas CD73-dependent adenosine generation induces a novel form of leukocyte-endothelial cell cross-talk that results in reduced leukocyte adhesion to the endothelium and decreased transmigration into tissues in the setting of hypoxia-associated inflammatory responses (Eltzschig, et al, *Blood* 104: 3986-3992, 2004). Therefore, it is possible that the intragraft level of CD73 expression effects on the outcome of cardiac allografts. Because recipient-derived cells infiltrate into allografts over time and injury to the donor-derived cells in allografts is a progressive process, our model results in a total CD73 expression in cardiac allografts that fluctuates with time. It is noted that allotransplants of CD73$^{-/-}$ donors or recipients were found to have lower levels of CD73 expression throughout the post-transplantation period, resulting in increased cardiac graft damage. In our cardiac isograft transplantation experiment, the homologous combination of CD73$^{-/-}$ donors and recipients resulted in an accelerated inflammatory response when compared with a heterologous combination of CD73$^{-/-}$ donors and CD73$^{+/+}$ recipients, and vice versa (data not shown). Our in vitro coculture studies involving CD73$^{-/-}$ T lymphocytes and CD73$^{+/+}$ endothelial cells supplemented with APCP (an inhibitor of CD73) significantly enhanced the transendothelial migration of T lymphocytes, as well as TNF-α and VCAM-1 expression. Thus, CD73 expressed on both local and circulating cells could contribute to preserving, vascular homeostasis after cardiac transplantation.

In summary, the experiments described herein demonstrate that both local and circulating CD73 contribute to allograft-protection in cardiac transplantation, leading to improved allograft survival and protection against CAV development. Mechanisms underlying this protection likely include 1) the maintenance of graft barrier function due to a concurrent upregulation of $A_{2B}AR$ in the I/R phase; 2) suppression of the inflammatory response, possibly due to a upregulation of $A_{2B}AR$; and 3) suppression by CD73 of the transit of effector leukocytes across graft endothelium. These studies point to CD73 as residing at the nexus of inflammatory and vascular reactions that can protect a vulnerable graft and its vasculature from immune attack.

Endothelial Ecto-5' Nucleotidase (CD73) Regulation of Leukocyte Trafficking in the Ischemic Brain Particular embodiments of the inventive methods described herein are drawn to preventing or treating cerebrovasular ischemia. Cerebral ischemia elicits a strong inflammatory response. (1) Though multiple cellular and humoral mediators of this inflammatory response have been identified, little is known about humoral mediators whose catabolism in the extracellular intravascular milieu modulates cell-cell interactions which promulgate inflammation and ischemic tissue damage. Within the primary area of cerebral infarction, neurons and glial cells become heavily damaged, resulting in extensive Wallerian and terminal degeneration, loss of distal microvascular flow and regional edema. These characteristic histopathological changes are accompanied or exacerbated by infiltration of polymorphonuclear and mononuclear leukocytes, as well as reactive astrocytosis, which can all play a role in the development of secondary injury after acute brain infarction (Bruan, et al, *Brain* 766: 213-266, 1997). Recruitment of inflammatory cells into underlying tissue occurs by a stepwise process of homing, adhesion, and ultimately, diapedesis. Cells emigrate between the endothelial cells that line the inner surface of blood vessels and astroglial feet that comprise the neurovascular unit into the parenchyma of the brain (Salmi, et al, *Nat Rev Immunol* 5: 760-771, 2005). Recent work has shown that transcellular metabolism by endothelial-surface ENTPDase1 (CD39) of extracellular nucleotide tri- and di-phosphates (ATP/ADP) released by activated platelets can mitigate explosive amplification of thrombotic nidus formation, thereby mitigating damage in ischemic/reperfused stroke (Pinsky, et al, *J Clin Invest* 109: 1031-1040, 2002).

To specifically evaluate the contribution of CD73 as an inflammatory modulator in the microenvironment of ischemic brain injury, experiments were performed using a modification of a recently described model of photothrombotic occlusion of the middle cerebral artery (Reichmann G., et al 2002). The photothrombosis stroke model was employed because of its propensity to create intravascular thrombus, similar to that seen in human stroke, as well as cortical infarcts which are highly reproducible in location and size, which is essential for quantification of cellular response. Genetic, pharmacologic, and cellular approaches were used to study the contribution of CD73, as well as CD73 catalytic activity, on leukocyte trafficking and neurologic outcomes in the setting of stroke.

Uncontrolled inflammation plays an important role in the pathogenesis of major diseases including stroke, cancer, heart disease, atherosclerosis and sepsis. Because of that, the immune response has to be tightly regulated by highly effective downregulating immunological mechanisms, as well as "nonimmune" molecules and metabolites that may have capacity to inhibit activated immune cells thereby prevent excessive tissue damage. (Sitkovsky, M. V., *Biochem Pharmacol* 65: 493-501, 2003) Local tissue hypoxia, which develops as a result of local tissue damage, and damage-associated interruption in blood supply, may represent one of the first events that initiates the termination of inflammation by creating conditions that are conductive to the accumulation of extracellular adenosine*** (Under such conditions, adenosine first serves to "report" the excessive collateral immune damage; it then prevents additional damage by inhibiting activated immune cells.

CD73 is abundantly expressed on vascular endothelial cells, and on 5%-15% of peripheral blood lymphocytes, whereas granulocytes and monocytes are completely negative (Jalkanen, et al, *Arterioscler Thromb Vasc Biol* 28: 18-26, 2008; Yamashita, et al, *Eur J Immunol* 28: 2981-2990, 1998). Thus, a potential biological role for CD73, which most likely extends beyond its enzymatic activity, is to catalyze the breakdown of AMP, leading to accumulation of adenosine (30-100 times that of the resting concentrations) and subsequent purine-P1 receptor binding during times of physiologic stress. (Hasko, et al, *Trends Pharmacol Sci* 26: 511-516; 2005) In other words, adenosine increase in situations when there is an imbalance between rates of energy utilization and rates of energy delivery, and since adenosine tends to reset the balance, it has been called a "retaliatory metabolite" (Dare, et al, *Physiol Behav* 92:15-20, 2007; Li, et al, *Microvasc Res* 72: 48-53, 2006)

The complexity of the role of adenosine could be explained by the identification of four adenosine receptors: A1, A2A, A2B and A3, which are located within the brain, on neurons, glial cells, blood vessels, leukocytes and platelets, with unique distribution among specific brain region (Fredholm, B. B., *Cell Death Differ* 14: 1315-1323, 2007).

In the first and second sets of experiments, we combine genetic and pharmacologic approaches in order to clarify the role of CD73 in regulation of anti-inflammatory cerebroprotection. Because CD73 is express by vascular endothelium, but also by circulating lymphocytes, a BM transplantation model was used to distinguish the relative contributions of CD73 on different cell types to neuronal injury in the brain. These studies revealed for the first time that, in a setting of ischemic stroke, $CD73^{-/-}$ mice, have shown significant ≈50% increase of infarct volume, ≈56% neurological deficit, ≈30% increase of brain edema and leukocyte influx compared to WT controls. Other studies have suggested that CD73 contributes to the protective aspects of adenine nucleotide metabolism during hypoxia and ischemia and that ischemia following permanent cerebral artery occlusion in rat brain results in an up regulation of CD73 expression in infracted tissue. This is indicative of a reactive increase in the potential of the brain tissue to hydrolyze extracellular nucleotides released as a consequence of severe tissue damage (Braun, et al, *Brain Res* 766: 213-226, 1997; Li, et al, *Microvasc Res* 72: 48-53, 2006). A hypoxic environment may also induce expression of CD73 which is transcriptional regulated by hypoxia-inducible factor-1 (HIF-1), since CD73 has a HIF-1 alfa responsive element in its promoter region (Synnestvedt, et al, *J Clin Invest* 110: 993-1002, 2002; Thompson, et al, *J Exp Med* 2004: 1395-1405, 2004). These data together emphasize that the dephosphorylation of AMP by CD73 represents the major pathway of extracellular adenosine formation during oxygen supply imbalances—a hallmark of brain ischemia.

Furthermore, our experimental results demonstrate the first direct link between CD73 and control of leukocyte trafficking into ischemic brain tissue. Our quantitative analyses suggest a relevant inflammatory reaction 48 hrs after induction of permanent MCAO. Although the total number of neutrophils and microglial cells has shown around 2 fold increase in ischemic hemispheres of CD73 null mice in comparison with WT animals, cells infiltrating the ischemic hemispheres of CD73 knockout animals showed a shift toward the mononuclear cell fraction. In comparison with WT mice, we observed a 44% increase in the relative ratio of macrophages, as well as total cellular infiltration of those cells in ischemic hemispheres of CD73 null animals. In addition, our work showed that macrophages exposed to the more inflammatory environment in the CD73−/− mice, express higher levels of costimulatory molecules B7-1 and B7-2 then macrophages isolated from the ischemic hemispheres of WT mice, and thus become more activated and shifted toward a phagocytic phenotype. We also observed much higher levels of CD80 molecule expression in ischemic hemispheres of CD73 null mice then CD86 molecule expression, in comparison with expression of those molecules observed in the wild type mice.

A number of studies have suggested that CD73 is a key component of a protective pathway to maintain a barrier function in epithelia and endothelia (Synnestvedt, et al, *J Clin Invest* 110: 993-1002, 2002); (Eltzschig, et al, *Blood* 104: 3986-3992, 2004). Furthermore, the barrier-promoting function of ATP released from activated neutrophils in vitro, was found to be dependent on ATP hydrolysis to adenosine via coordinated action of both, CD39 and CD73 (Eltzschig, et al, *Blood* 104: 3986-3992; Lennon, et al *J Exp Med* 188: 1433-1443, 1998). Even though the exact source of extracellular adenosine that is generated during episodes of hypoxia and ischemia remains unknown, ATP can be generated by polymorphonuclear leukocytes, platelets, or endothelia during conditions of inflammation. Therefore, in addition to CD73, CD39-dependent conversion of extracellular ATP/ADP provides the metabolic substrate for CD73, but in the same time CD39 is responsible for decreasing extracellular ADP levels, thereby eliminating ADP as feedforward inhibitor of CD73 (Yegutkin, et al, *Faseb J* 15: 251-260, 2001). Indeed, our previous work demonstrated that CD39-deficient mice developed worse clinical outcome then WT controls following induction of cerebral ischemia (4). Neutrophils are known to accumulate at sites of inflammation between 24 and 48 hrs after permanent ischemic brain damage in rat and mice (Campanell M., 2002; (Stevens, et al, *Brain Res* 932: 110-119, 2002) and are well demonstrated sources of adenine nucleotides in the form of 5'-AMP and ATP (Eltzschig, et al, *Circ Res* 99: 110-1108, 2006). Through activation of the adenosine receptors $A_{2A}$ and $A_{2B}$ at the surface of activated neutrophils, adenosine (Eltzschig, et al, *Methods Mol Biol* 341: 73-87, 2006) functions as an anti-adhesive signal for the binding of neutrophils to microvascular endothelial cells, a mechanism which could play a main role in the accumulation of neutrophils observed in the ischemic hemispheres of CD73 null mice in our study (Eltzschig H. K., et al., 2004). This is consistent with the findings that $A_{2A}$ deficient animals have exacerbated inflammation and wild type mice that have been treated with $A_{2A}$ antagonist have shown high rate of inflammation as well. (Sitkovsky, M. V., *Biochem Pharmacol* 65: 493-501, 2003) Early studies demonstrated that adenosine has direct inhibitory effects on two major determinants of endothelial cell activation, release of cytokines and de novo expression or upregulation of adhesion molecules and that adenosine may affect both early and more advanced stages of endothelial cell activation during development of inflammatory response. (Bouma, et al, *Shock* 8: 313-320, 1997). Since we observed an upregulation of mRNA for keratinocyte chemoattractant (KC), the main cheniokine responsible for neutrophils migration into sites of inflammation, in ischemic hemispheres of CD73 deletional mutants, this could be another possible explanation for accumulation of neutrophils in those mice after the brain ischemia.

On the other hand, macrophages show different kinetics: they are first observed at 12 hours after ischemia, but increase in number several days after, before reaching the plateau (Stevens, et al, *Brain Res* 932: 110-119, 2002; Ford, A. L. *J Immunol* 154: 4309-4321, 1995). Macrophages have central role in dictating inflammatory resolution. Although macrophages provide an important defense against injury, their over activation can cause damage to inflamed tissue and such over activation may be prevented by adenosine. (Hasko, et al, *Pharmacol Ther* 113: 264-275, 2007) Recent studies have shown, that adenosine is strong inhibitor of TNF-α and IL-6 from monocytes and macrophages, an effect which may involve both of adenosine A2 receptors (Kreckler, et al, *J Pharmacol Exp Ther* 317: 172-180, 2006) ((Hasko, et al, *Pharmacol Ther* 113: 264-275, 2007). Adenosine and its analogues inhibited the MHC class II expression induced by IFN-γ as well as other activities induced by INF-γ such as the induction of iNOS and the regulation of the expression of proinflammatory cytokines such as TNF-α or IL-1β and some LPS-induced functions in macrophage activation (Hasko, et al, *Faseb J* 14: 2065-2074, 2000). In addition, adenosine facilitates IL-10 production by stimulation of $A_{2A}$ and $A_{2B}$ receptors on murine peritoneal macrophages, an effect which can contribute to the anti-inflammatory and immunosuppressive action of adenosine. (Nemeth, et al, *J Immunol* 175: 8260-8270, 2005). These data are in agreement with observation we made in this study, that mRNA of certain pro-inflammatory cytokines-IL-6, KC, TNF-α, IL-1β as well as VCAM-1 are upregulated in ischemic hemispheres of CD73 knockout animals in comparison with the WT controls, correlating with more inflammation observed in CD73 null mice. We also observed that in ischemic hemispheres of CD73 animals, there is a tendency of downregulation of anti-inflammatory IL-10 mRNA, but it didn't reach statistical significance when compared to WT mice.

According to our knowledge, this study for the first time confirm that CD73 and its metabolite adenosine can regulate expression of costimulatory molecules such as B7-1 (CD80) and B7-2 (CD86) on macrophages thereby playing an important role in the downregulation and polarization of the immune response in the settings of stroke and potentially other immune-inflammatory disorders. Parameters of the microglial/macrophages response to CNS injury as dissected in numerous paradigms include the upregulation of MHC II and CD80/CD86 and the entry into the cell cycle (Reichmann, et al, *Neuroimmunol* 129: 125-132, 2002). Several line of evidence indicates that antigen presentation in the brain upon B7-1 costimulation is related to destructive autoimmunity (Wolf, et al, *Glia* 36: 414-420, 2001)(Bechmann I., et al 2001). Since naïve T cells can enter inflamed CNS tissue, in the absence of adenosine macrophages from ischemic hemispheres of CD73 null mice, with upregulated costimulatory molecules, may polarize immune response toward pro-inflammatory Th1 response and thus increase the risk of posttraumatic autoimmunity. This hypothesis could be strengthened by the fact that we found downregulation of mRNA for IL-10 in ischemic hemispheres of CD73 null mice along with the up regulation of others pro-inflammatory cytokines such as TNF-α. Taken together, these experiments provide the first genetic evidence of a nonredundant role for endogenous CD73 and its metabolite adenosine in cerebroprotection and inflammation after induction of permanent brain ischemia.

As a proof of principle for the assertion that CD73 plays an important role in cerebroprotection, CD73$^{-/-}$ as well as WT mice, were reconstituted with soluble 5'nucleotidase purified from *C. atrox* venom. Our data show that treatment with soluble 5'nucleotidase mimicked cerebroprotection and it was associated with significant attenuation of infarct volume, improved functional outcome and reduced leukocyte infiltration 48 hrs after induction of brain ischemia. This emphasizes the role of CD73 and extracellular adenosine as a key control point for regulation vascular inflammation associated with brain ischemia.

The importance of CD73-dependent adenosine production has been demonstrated by gene-deficient mice, CD73 inhibitor, and administration of soluble enzyme. Experiments in mice with endogenus deletion of CD73 have shown that those animals have enhanced inflammatory and prothrombotic responses, which have been attributed to attenuated leukocyte adhesion and platelet accumulation. (31).

More importantly, recent studies demonstrate that adenosine generated by the actions of CD73 is an important endogenous pathway to modulate inflammatory the vascular response, as only CD73 null mice demonstrated significantly increased leukocyte adherence to the vascular endothelium in a model of cremaster muscles ischemia-reperfusion injury (Zernecke, et al, *Circulation* 113: 2120-2127, 2006).

CD73 and its active metabolite adenosine dose-dependently inhibit VCAM-1 but not ICAM-1 expression in activated human endothelial cells (EC) in vitro. In line with increased VCAM-1 expression, monocyte arrest was markedly increased in CD73$^{-/-}$ EC in vitro and predominantly mediated by VLA-4/VCAM-1. (Zernecke, et al, *Circulation* 113: 2120-2127, 2006). Moreover, CD73-deficient mice are prone to more severe vascular leakage than wild-type animals in hypoxic conditions, demonstrated increased neutrophil infiltration, which could be reversed by administration of soluble CD73 (Thompson, et al, *J Exp Med* 200: 1395-1405, 2004). These data imply that CD73 can control the inflammatory status of the specific microenviroment, mainly by regulating the dynamic of leukocyte endothelial interaction.

Given that of CD73 is expressed on leukocytes and subpopulation of peripheral blood lymphocytes, circulating cells recruited to sites of injury may provide an important source of local CD73 to limit response to tissue inflammation. The reconstitution of wild type animals with CD73-/- bone marrow (KO→WT) compared with global inactivation of this molecule (KO→KO), however provides significant protection from brain ischemia, as we observed around a 40% decrease in infarct volume in CD73 KO→WT chimeric mice. Conversely, expression of the CD73 molecule on bone marrow cells only, (WT→KO) provides limited protection from brain ischemia, which represents only 14% decrease in infarct volume in comparison with mice which lack the CD73 in both tissues. Parallel to the reduced infarct volume, locomotor activity in the KO→WT was substantially better than in the KO→KO, as well as the degree of inflammation as measured by cellular infiltration after brain ischemia. Similarly, the total number of infiltrating macrophages was significantly increased, 2.5-2 fold in KO→KO and WT→KO mice when compared to either WT→WT or KO→WT mice respectively. In addition, macrophages isolated from completely CD73-deficient mice express around 60% more CD80 molecule, but only 26% more of CD86 molecule, when compared with WT→WT controls the presence of the CD73 molecule in tissue only abolish the expression of both CD80 and CD86 molecules when compared with completely CD73-deficient chimeras. On the other hand, macrophages isolated from ischemic hemispheres of mice deficient in tissue CD73 only (WT→KO), express significantly higher level of CD80, but not CD86 molecule, when compare with macrophages isolated from control chimeric mice WT→WT.

Even though our data can not rule out the possibility that circulating cells may provide an additional source of adenosine available at the vascular endothelial interface, endogenous adenosine generated by tissue/resident expressing cells appears to be of prime importance in cerebroprotection.

Recent immunohistochemistry study revealed that even though, human endothelial cells express CD73, mouse brain endothelial cells are CD73 deficient (Mills, et al, *Proc Natl Acad Sci USA* 105: 9325-9330, 2008). Using multiplex Q PCR technique, we found that mRNA for CD73 is expressed on bEND.3 mouse endothelial cell line (data not shown). However, CD73 was found to be highly express on choroid plexus epithelial cells, which form the barrier between the blood and cerebrospinal fluid, and are known to have a role in immunosurveillance in the CNS (Mills, et al, *Proc Natl Acad Sci USA* 105: 9325-9330, 2008)

Although lymphocyte and endothelial cells express structurally similar CD73 molecules, the expression of these ecto-enzymes is differentially regulated in these two types of cells. Engagement of lymphocyte CD73 triggers a rapid shedding of surface CD73 and leads to clustering of CD11a/CD18 (LFA-1) integrin thereby eliciting the integrin-mediated binding of lymphocytes to endothelium (Airas, et al, *J Exp Med* 182: 1603-1608, 1995). By contrast, engagement of endothelial CD73 does not result in shedding of the enzyme. However; interferon (IFN)-α regulates CD73 expression on endothelial cells. On lymphocytes, in contrast, IFN-α has no effect on the levels of CD73 molecule. Moreover, CD73 functions as an adhesion molecule for lymphocytes (Airas, et al, *J Exp Med* 182: 1603-1608, 1995), and thus cells that characteristically traffic later in the inflammatory response (i.e. lymphocytes an monocytes) may be orchestrated by brain tissue resident cells which express CD73.

Since the enzymatic reactions are very fast and well suited for signal amplification, they can be regulated at multiple levels because of substrate availability, natural inhibitors and further metabolism therefore are ideally fit for rapid tuning of the leukocyte extravasation cascade. In the case of CD73, for instance, availability of the substrate (AMP) partially controls the amount of adenosine produced, and other purines like ATP and ADP can inhibit the function of CD73.

Ecto-5' NT has also been implicated in cell-matrix interactions in chicken fibroblasts and as a signal transducing molecule in the human immune system. CD73 has been detected in nervous tissue: on venules in various tissues and on follicular dendritic cells in the secondary lymphoid organs (Airas L., et al., 1993).

A subpoulation of peripheral blood lymphocytes express CD73 on the majority of B cells and CD8+ T cells, but only 10% of CD4+ T cells express this enzyme.

It is known that catalytic activity of CD73 accounts for the immunosuppressive function of these cells because adenosine produced suppress proliferation and cytokine secretion of T helper 1 and 2 effector cells. However, its role as a costimulatory molecule in T cell activation has been already well established and on lymphocytes CD73 serves as a maturational marker, being absent from the surface of both immature B and T cells.

Other studies have suggested that CD73 contributes to the protective aspects of adenine nucleotide metabolism during hypoxia and ischemia and that ischemia following permanent cerebral artery occlusion in rat brain results in an up regulation of CD73 expression in infarcted tissue. Finally, a hypoxic environment may also induce expression of CD73 which is transcriptionally regulated by hypoxia-inducible factor-1 (HIF-1), since CD73 has a HIF-1 alpha-responsive element in its promoter region. These data together emphasize that the dephosphorylation of AMP by CD73 represents the major pathway of extracellular adenosine formation during oxygen supply imbalances.

A more delayed protective pathway involves isolating the damaged tissue by an astrocytic scar and eliciting the astrocytic support of neurons. (de Mendonca A., et al., 2000).

Eventually, in the long term, adenosine might be a modulator in eliminating the affected tissue of dead cells and debris by inducing microglial proliferation and phagocytosis, as well as, facilitating tissue remodeling after injury by promoting angiogenesis and replacement of dysfunctional blood vessels (Fisher S., et al., 1995). As crucial elements of innate immune responses, monocytes/macrophages express surface molecules such as major histocompatibility complex and costimulatory molecules, as well as cytokines and free radicals, which, on the other hand, activation of lymphocytes critically depends. The purpose of cooperation between those two types of cells could be further destruction of pathogens, virus-infected cells, tumor cells as well as elimination of host apoptotic cells (Hasko G., et al 2007). Once the inflammatory/immune response has eliminated an injurious agent, the process of inflammatory resolution ensues, which is orchestrated by endogenous "pro-resolving" mediators like adenosine, in a highly coordinated way.

It is known that isolated heart studies suggest that adenosine kinase inhibition in hypoxic conditions also contributes to adenosine accumulation since about 80% of adenosine is rephosphorylated to AMP by this enzyme in normoxic myocardium. This metabolic compensation is thought to play important protective and regenerative functions to control subsequent tissue damage. Particularly, adenosine is known to has a protective effect in ischemia-induced endothelial injury, maintain endothelial barrier function, support vasodilatation, suppresses leukocyte adhesion to the vascular endothelium and play a role in processes of tissue remodeling after injury and resolution of inflammation (Ohta A & Sitkovsky M., 2001.

The invention can further be used as a treatment for thrombotic or inflammatory disorders, including but not limited to myocardial ischemia or infarction, cerebrovascular ischemia or infarction, subarachnoid hemorrhage, artificial graft or stent implantation, balloon angioplasty, deep venous thrombosis, pulmonary embolism, ischemia of solid organs including but not limited to heart, lung, liver, brain, kidney, skin, pancreas, or bowel. Ischemia can either be spontaneous or induced, such as occurs during surgery such as cardiopulmonary bypass surgery or vascular bypass surgery. In one embodiment of the invention, specific adenosine receptor precursor or agonists are given to reduce transplant vasculopathy. In other embodiments, the adenosine receptor precursor or agonist can be administered alone or in combination with CD73 or other agents which dissipate the ambient nucleotide phosphate milieu. In one specific embodiment, the adenosine receptor precursor or agonist is a nonselective adenosine receptor agonist. In another embodiment, the treatment is with an adenosine receptor type 2A agonist. In another embodiment, the adenosine receptor agonist is an adenosine type 2B receptor agonist. In another embodiment, the adenosine receptor agonist is an adenosine type 3 receptor agonist. In another embodiment, the adenosine receptor agonist is an adenosine type 3 receptor agonist.

This invention will be better understood from the Experimental Details which follow. These sections are set forth to aid in an understanding of the invention but are not intended to, and should not be construed to, limit in any way the invention as set forth in the claims which follow thereafter.

EXAMPLES

Example 1

Lung Transplant

Acute rejection after lung transplantation is a main risk factor for the development of bronchiolitis obliterans (BO) syndrome and is characterized by a perivascular and bronchiolar leukocyte infiltration. The specific mechanisms by which these leukocytes are recruited have not been elucidated. CD73 catalyzes the extracellular conversion of 5'-AMP to adenosine, which has anti-inflammatory actions, a contributory role for CD73 in BO development was examined using murine tracheal transplantation models.

Mice

Male mice aged between 8 and 12 weeks old were used in these experiments. C57BL/6 (H-$2^b$) mice and B10.A (H-$2^a$) mice were purchased from Jackson Laboratories. Isogeneic tracheal transplants were performed using C57BL/6J mice as both recipients and donors. Allogeneic (B10.A) tracheal grafts from donor mice were transplanted into wild-type (C57BL/6) or CD73$^{-/-}$ recipient mice. To specifically determine the role of epithelial-versus leukocyte-derived CD73$^{-/-}$, reverse donor/recipient transplantation experiments were performed using wild-type donor (C57BL/6) or CD73$^{-/-}$ airway allografts transplanted into B10.A recipients. The genotype of each mouse was confirmed by genomic PCR and the background of these mice is C57BL/6, all of which have an H-$2^b$ genotype.

Tracheal Transplant Models

Two well-established tracheal transplant models were used to study the effect of CD73 on the pathogenesis of allograft rejection. The first model was the previously described double lumen airway (orthotopic) transplant model for studying chronic airway rejection (Harada, et al, *Am J Physiol Lung Cell Mol Physiol* 293: L124-130, 2007; Minamoto, et al, *J Exp Med* 202: 283-294, 2005). Briefly, after anesthesia, donor mice were exsanguinated, and whole trachea was harvested by transecting below the cricoid cartilage distal to the carinal bifurcation under sterile conditions. Recipient mice were similarly anesthetized, and the whole trachea was exposed. Distal (the seventh intercartilaginous space) and proximal (immediately subjacent to the cricoid cartilage area) orifices positioned on the recipient trachea were anastomosed with both ends of the tracheal graft. This air permissive model mimics lymphocytic bronchitis and allows studies focusing on inflammation. All surgeries were performed using a Leitz-Wild surgical microscope (Urban Engineering, Burbank, Calif.) under ×16 magnifications.

A heterotopic model, characterized by epithelial and subepithelial lymphocyte infiltration by one was also used (Lama, et al, *Am J Pathol* 169: 47-60, 2006). Donor tracheas were harvested as described above. The trachea was inserted in a subcutaneous pouch created after a 3-mm incision and blunt dissection in the back of the neck. The skin pocket was closed with a size 5.0 nylon suture.

Histopathological Evaluation of Tracheal Transplants

Grafts were harvested at the indicated time points and embedded en bloc in Tissue Freezing Medium (Triangle Biomedical Sciences, Durham, N.C.) in Disposable Base Molds (Richard-Allan Scientific, Kalamazoo, Mich.) in liquid nitrogen and stored at −80° C. until the time of analysis. For the orthotopic model histochemical staining was performed for elastin (Accustain; Sigma-Aldrich) to determine graft luminal occlusion on 5-μm-thick sections. Immunostaining was also performed using, serial adjacent sections from each group, with primary antibodies directed against a pan-T-cell marker (hamster anti-mouse CD3; BD Pharmingen, San Diego, Calif.). Morphometric measurements of cross-sectional areas were performed by blindly tracing both epithelial and subepithelial areas using a computer-assisted image analysis system (AxoCamHR; Carl Zeiss Microimaging, Thornwood, N.Y.). All samples were analyzed at 1 week after transplantation, because that was the time of maximal lumen narrowing and cellular infiltration in allografts (Harada, et al, *Am J Physiol Lung Cell Mol Physiol* 293: L124-130, 2007). Quantitative analysis of T cell infiltration was performed by manually counting the number of CD3-positive cells in epithelial and subepithelial layer under high-power magnified fields.

mRNA Isolation and Real Time PCR Analysis

Total RNA was extracted from frozen each mouse tracheas using RNeasy Mini Protocol for Tissues (Qiagen, Valencia, Calif.) and reverse transcribed using a High Capacity cDNA Archive Kit (ABI, Foster City, Calif.), in each case according to the manufacturer's instructions. One microgram of sample RNA was transcribed to cDNA. Real-time PCR was performed on an Applied Biosystems 7000 Real-Time PCR System (ABI) data collection system, and analyses were performed using the accompanying software.

PCR fluorogenic probes for all the target genes and the endogenous reference were purchased as TaqMan® Gene Expression Assays (ABI).

Adenosine Receptor Agonist Treatment.

A2A receptor agonist 2-p-(2-carboxyethyl) phenethyl-amino-5'-N-ethylcarboxamidoadenosine (CGS-21680, 2 mg/kg/day), A2A receptor antagonist 5-Amino-7-(β-phenylethyl)-2-(8-furyl)pyrazolo(4,3-e)-1,2,4-triazolo1,5-c pyrimidine (SCH-58261, 2 mg/kg/day), A3 receptor agonist [2-chloro-N$^6$-(3-iodobenzyl)adenosine-5'-N-methyluronamide (Cl-IBMECA 1 mg/kg/day), A3 receptor antagonist 3-Ethyl 5-benzyl 2-methyl-6-phenyl-4-phenylethynyl-1,4-(±)-dihydropyridine-3,5-dicarboxylate (MRS 1191 2 mg/kg/day) or vehicle (0.1% DMSO in PBS) was administered in a sterile 0.1-ml volume by intraperitoneal injection every 12 hours after surgery. The doses of the adenosine-receptor agonists' were chosen according to previous studies (Erdmann, et al, *Blood* 105: 4707, 4714, 2005; Hasko, et al, *Faseb J* 14: 2065-2074, 2000; Satoh, et al, Pancreas 24: 75-82, 2002; Satoh, *Gastroenterology* 119: 829-836, 2000). The adenosine receptor agonists and antagonists were obtained from Sigma Chemicals (St. Louis, Mo.).

Statistics

All statistical comparisons were performed using a commercially available statistical package for the Macintosh personal computer (Stat View-J 5.0; SAS Institute). Student's t tests were used to determine p values when comparing two groups. Values are expressed as mean±SEM, with differences considered statistically significant at P<0.05

Results

Effects of CD73 on Graft Luminal Narrowing in Orthotopic Model

To determine the influence of CD73 on the graft luminal narrowing, morphometric analyses were performed on WT allograft, WT isograft and allograft in CD73$^{-/-}$ recipient at day 7, the peak of inflammation and airway luminal narrowing (Harada, et al, *Am J Physiol Lung Cell Mol Physiol* 293: L124-130, 2007). WT allografts revealed thickening of the airway layers leading to luminal narrowing (47±5% for allografts; n=6 vs. 31±4% for isografts; n=6, (p=0.042, FIG. 1A). Allografts in CD73$^{-/-}$ recipients demonstrated significant increase in graft luminal narrowing (62±4%, n=6) compared with WT allografts (p=0.046, FIG. 1A).

To determine whether the site of CD73 expression (graft tissue versus infiltrating cells) is most critical to the observed protection against graft luminal narrowing in CD73 null allografts, another set of experiments was performed. In new experiments, CD73 gene-null grafts were placed into gene-competent (CD73$^{+/+}$) recipients, or alternatively, CD73 gene-competent grafts were placed in CD73 null hosts. Allografts taken from wild type donor mice to CD73$^{-/-}$ recipient exhibited increased airway luminal narrowing, however, no significant mitigation of airway rejection was observed when only the donor was CD73 null (FIG. 1B). These data indicate that recipient CD73 status is more critical than donor CD73 status in the pathogenesis of airway rejection.

Quantification of Graft T Cell Infiltration in Orthotopic Trachea Transplant Model To study the effect of CD73 on T cell infiltration, pan-T cell-marked CD3 positive cells were quantified using immunohistochemically stained frozen sections in CD73$^{-/-}$ allografts compared to WT allograft. Total CD3 positive cell counts were obtained from an entire section taken from the middle ⅓ of the tracheal grafts. There were significant differences in the number of infiltrating T-cells between WT allograft and CD73$^{-/-}$ allografts (number of cell in epithelial and subepithelial layer per slice; 313±43 vs. 520±41, n=4, p=0.013, FIG. 2B). In isografts, the number of CD3 positive cell was 67±18 (p=0.002 vs. WT allograft). This quantitative data match those of histological sections shown in FIG. 1, and furthermore, the numbers of CD3 positive cells directly correlated with the exacerbation of airway luminal narrowing.

Intragraft Expression of T-Helper 1 Cytokines in Heterotopic Model

Figure 3B:
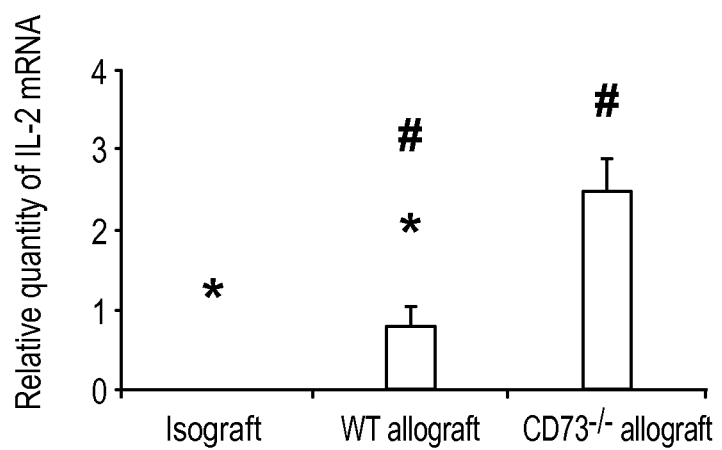

To investigate the correlations between CD73 and Th-1 cytokines, we examined the expression of IFN-γ and IL-2 mRNA in heterotopic trachea model (isograft, wild type allograft and CD73$^{-/-}$ allograft). The expression of IFN-γ mRNA was up-regulated in wild type allograft compared with isograft (4244-fold, p=0.014), and also up-regulated in CD73$^{-/-}$ allograft compared with wild type allograft (2-fold, p=0.015) (FIG. 3A). The expression of IL-2 mRNA was up-regulated in wild type allografts compared with isografts (244-fold, p=0.018) and also up-regulated in CD73$^{-/-}$ allograft compared with wild type allograft (3.5-fold, p=0.013) (FIG. 3B)

mRNA Expression of Adenosine Receptors

Figure 4:
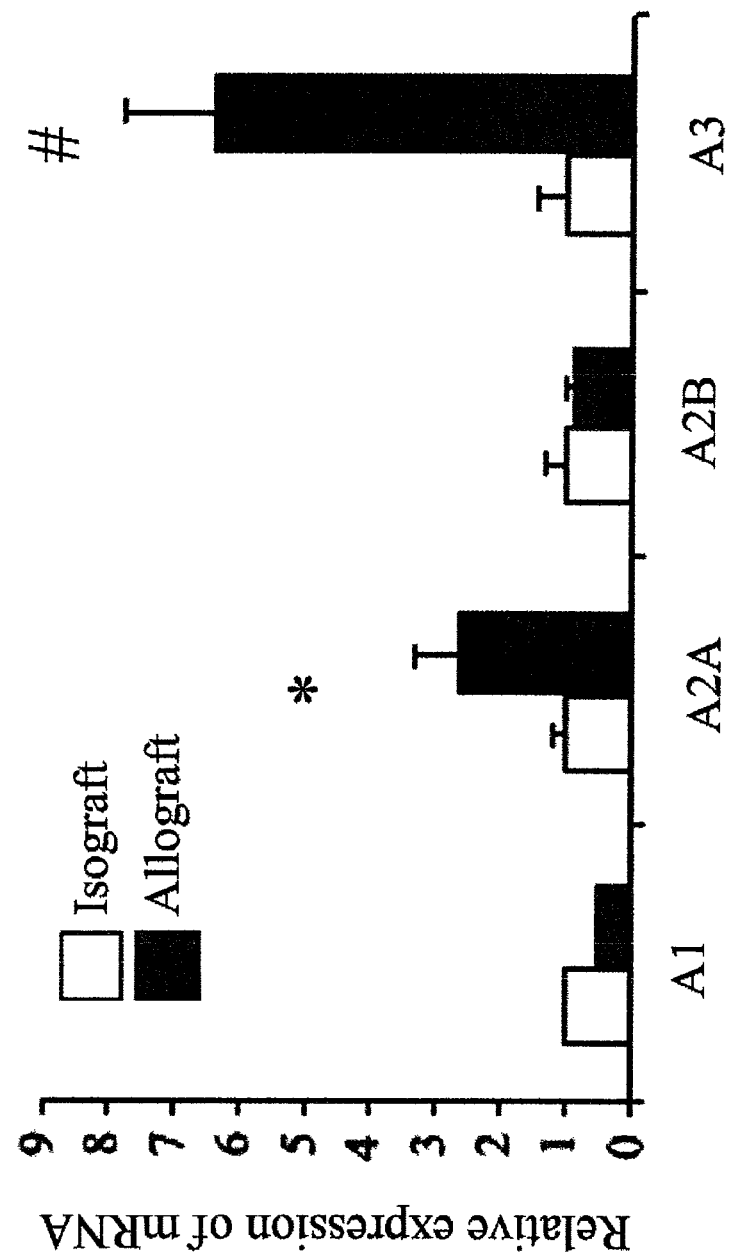
FIG. 4: Quantitative PCR analysis of RNA extracted from isografts and wildtype allografts in heterotopic. A2A (Adenosine type 2A) and A3 IADenosine type 3) receptors demonstrated significant up-regulation in the wild-type allografts as compared to isografts (2.7±0.7 fold and 6.3±1.3 fold, $p=0.04$ and 0.006, respectively. n=4). (*$p<0.05$, #$p<0.01$)

Quantitative PCR analysis of RNA extracted from isografts and wildtype allografts in heterotopic model were evaluated. A2A and A3 receptors demonstrated significant up-regulation in the wild-type allografts as compared to isografts (2.7±0.7 times and 6.3±1.3 time, p=0.042 and 0.006, respectively) (FIG. 4).

Effect of Adenosine Receptors Agonist

Figure 5A:
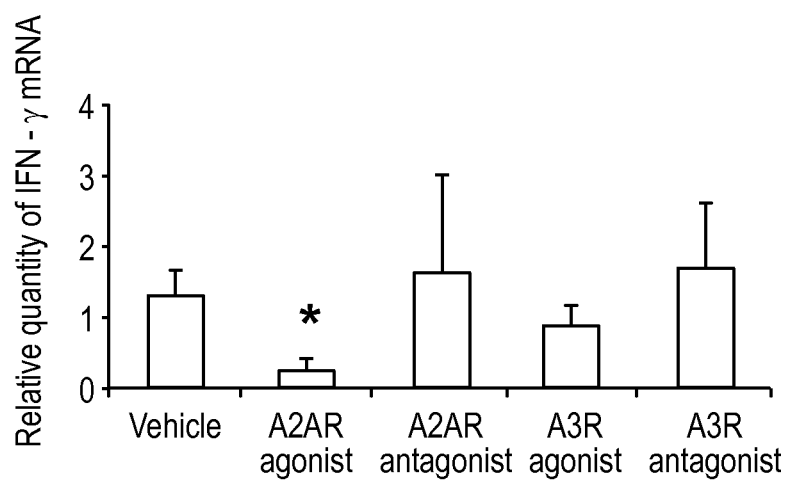
FIG. 5A-5B: (A) The expression of IFN-γ mRNA was down-regulated in wild type allograft treated with A2A receptor agonist compared with wild type allograft treated with vehicle ($p=0.033$). However, A2A receptor antagonist, A3 receptor agonist and A3 receptor antagonist did not affect mRNA expression of IFN-γ compared with vehicle (n=4-6 in each group). (*$p<0.05$ vs. vehicle) (B) The expression of IL-2 mRNA was also down-regulated in wild type allografts treated with A2A receptor agonist compared with wild type allograft treated with vehicle ($p=0.031$) (n=4-6 in each group). (*$p<0.05$ vs. vehicle)
Figure 5B:
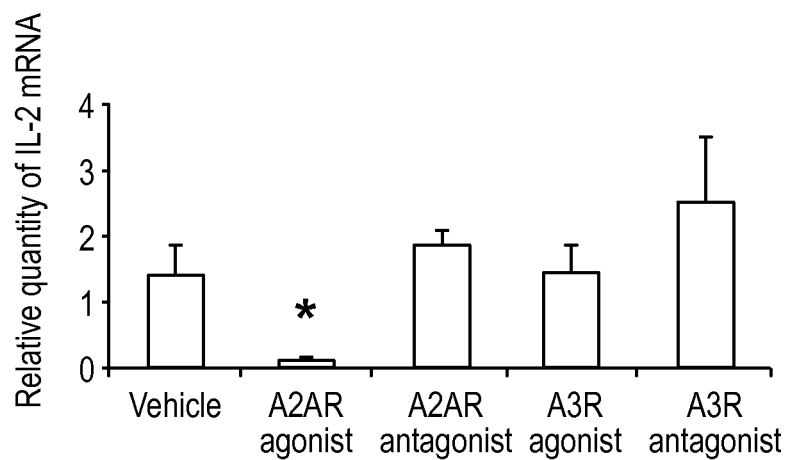

Since A2A and A3 receptors were up-regulated in allograft compared with isograft, we examined the effect of A2A and A3 receptor agonists and antagonists in orthotopic and heterotopic trachea transplant model. The expression of IFN-γ mRNA was down-regulated in wild type allograft treated with A2A receptor agonist compared with wild type allograft treated with vehicle (p=0.033), (FIG. 5A). The expression of IL-2 mRNA was also down-regulated in wild type allografts compared with wild type allograft treated with vehicle (p=0.031) (FIG. 5B).

Figure 6A:
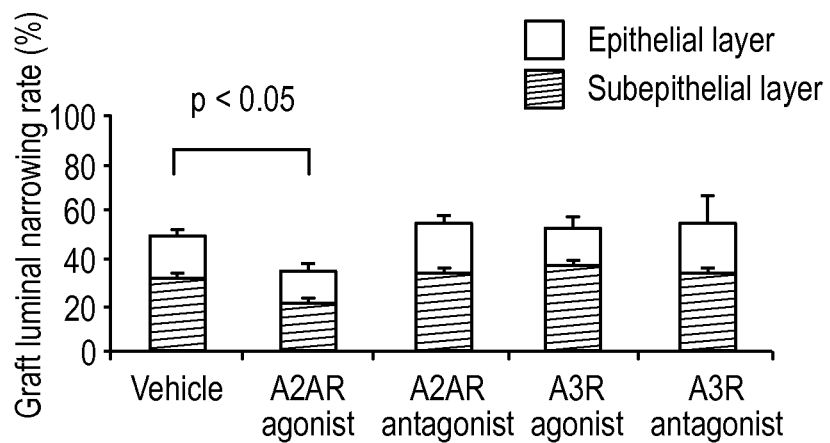
Figure 6B:
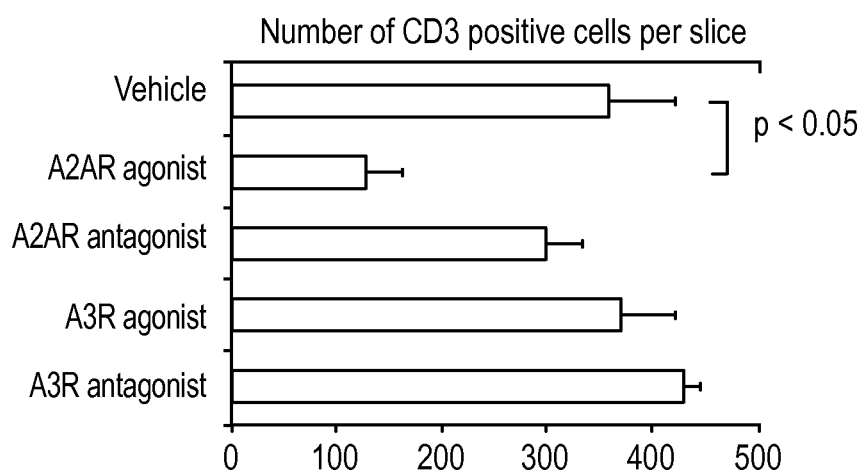

In the orthotopic trachea transplant model, wild type allografts treated with an A2A agonist exhibited significantly reduced luminal obliteration (p=0.035, FIG. 6A) and less CD3 positive cell infiltrations compared with allografts treated with vehicle (p=0.018, FIG. 6B).

Figure 7:
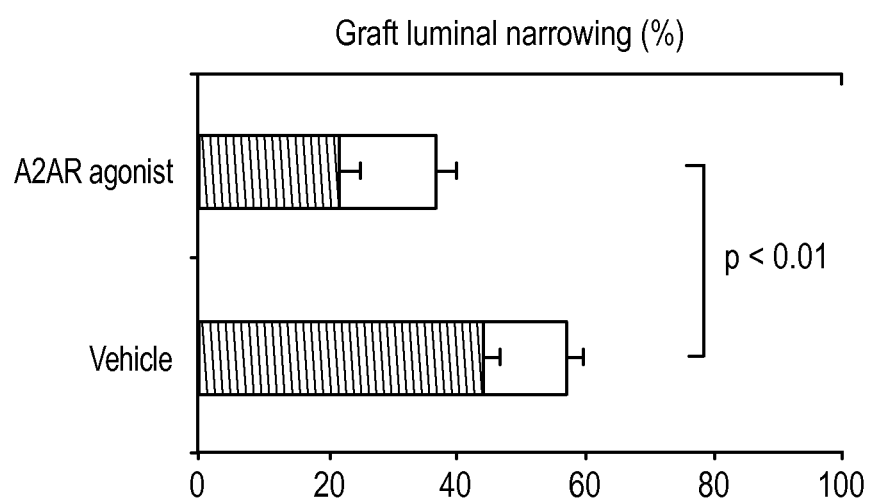
FIG. 7: Quantitative analysis of T cell infiltration by counting the number of CD3 positive cells under high power magnified fields. CD73$^{-/-}$ allografts with A2A receptor agonist administration demonstrated significantly decreased infiltration of T cells compared with CD73$^{-/-}$ allografts treated with vehicle.

In the orthotopic trachea transplantation model, CD73$^{-/-}$ allografts treated with A2A receptor agonist exhibited significantly reduced CD3 positive cell infiltrations (79±28) compared with allografts treated with vehicle (552+58) (p<0.01). Furthermore, CD73$^{-/-}$ allografts treated with A2A receptor agonist exhibited significantly reduced luminal obliteration (36±3%) compared with allografts treated with vehicle (57±3%) (p=0.009, FIG. 7).

Example 2

Heart Transplant Ecto-5' Nucleotidase (CD73)-Mediated Adenosine Generation and Signaling in Murine Cardiac Allograft Vasculopathy Experiments herein examine a role for CD73 and specific adenosine receptor subtypes in modulating leukocyte trafficking and ultimately, rejection and CAV following cardiac allotransplantation.

Materials and mMethods

Animals.

CD73-deficient mice (CD73$^{-/-}$) of C57BL/6 (H-2$^b$) background, are described previously[9]. CD73$^{+/+}$ littermates were used as the wild-type control. B10A (H-$2^a$) and CBA/J (H-$2^k$) mice were purchased from The Jackson Laboratories (Bar Harbor, Me.).

Experimental Groups.

Completely allomismatched murine heterotopic cardiac transplantation was performed for the present study, as previously described in detail by us[13]. Two groups (n=6 in each group) were used to study donor sources of CD73 (CD73$^{+/+}$ or CD73$^{-/-}$ donors into B10A recipients) and another two groups (n=6 in each group) were used to study recipient sources (B10A donors into CD73$^{+/+}$ or CD73$^{-/-}$ recipients). In experiments of adenosine receptor modulators, CBA/J mice were used as donors or recipients instead of B10A mice (n=4 to 6 in each group, as indicated).

In Vitro Experiments.

T lymphocytes were purified from splenocytes of CD73$^{+/+}$ and CD73$^{-/-}$ mice (H-$2^b$) using a Dynal mouse T cell negative isolation kit (Invitrogen). The BALB/c (H-$2^d$)-derived endothelial cell line bEnd.3 was obtained from American Type Culture Collection (Manassas, Va.).

Statistics.

Database management and statistical analysis were performed with the Statview version 5.0 software (SAS institute Inc., Cary, N.C.). All values are expressed as means±SEM. Kaplan-Meier analysis was performed to evaluate graft survival, and survival differences were compared by a log-rank test. Comparisons among groups were performed with an unpaired Student t test or one-way analysis of variance (ANOVA) where appropriate. Values of P<0.05 were considered statistically significant.

Results

Figure 8B:
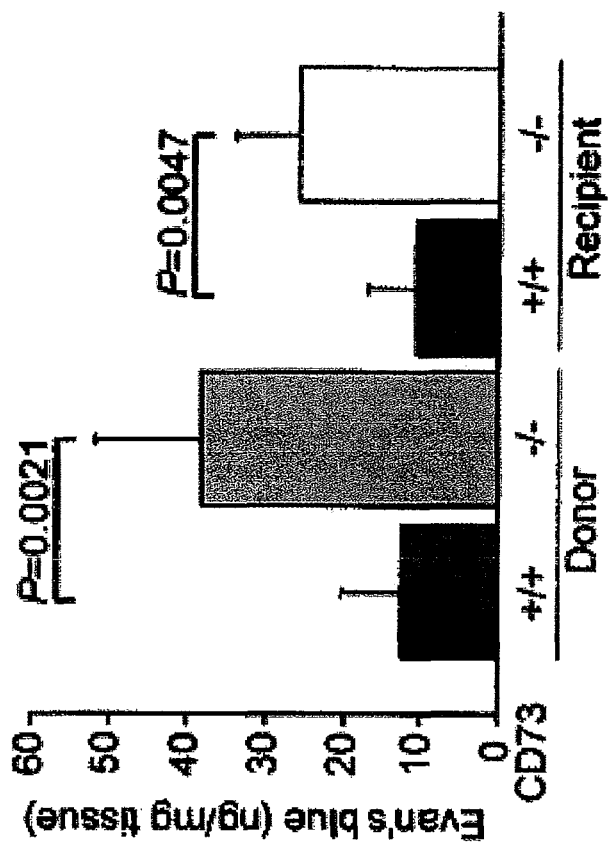
FIGS. 8A, 8B, 8C, 8D, and 8E: Graft survival and effects of CD73 on cardiac allografts at 4 hours after transplantation. (A) Survival of cardiac allograft. *$P<0.05$. (B) Graft permeability. (C) Immunohistochemical staining of the neutrophil marker Ly6G in cardiac allograft. Bar=50 μm. (D) Quantitative analysis of graft-infiltrating Ly6G-positive cells. (E) Graft MPO (myeloperoxidease) activity. ΔAbs, a change in absorbance. All data are expressed as mean±SEM for n=6 mice.
Figure 8A:
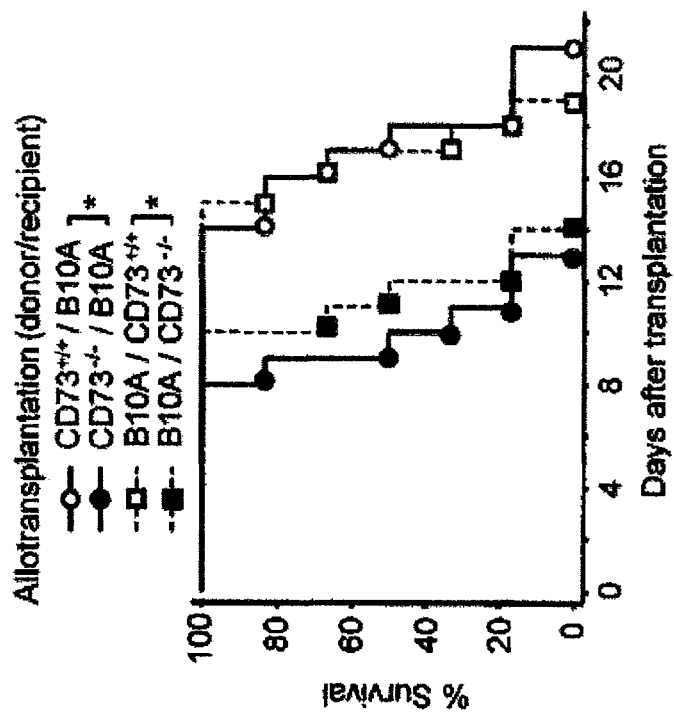

CD73 Deficiency in Either Donor or Recipient Mice Shortens Cardiac Allograft Survival To observe the relationship between cardiac allograft survival and CD73 expression in donor and recipient cells, completely allomismatched heterotopic cardiac transplantation was performed using CD73$^{-/-}$ mice as either donors or recipients. CD73$^{+/+}$ donor allografts survived between 13 and 20 days (16.3±1.0 days) after transplantation, whereas CD73$^{-/-}$ donor allografts survived for 10.5±0.6 days. CD73$^{+/+}$ recipient graft survival ranged from 14 to 18 days (16.0±0.6 days), whereas all CD73$^{-/-}$ recipients acutely rejected the donor hearts in less than 14 days (9.0±0.7 days). CD73 deficiency in donors or recipients significantly decreased cardiac allograft survival (P=0.0013, P=0.0005, respectively; FIG. 8A.

Figure 8C:
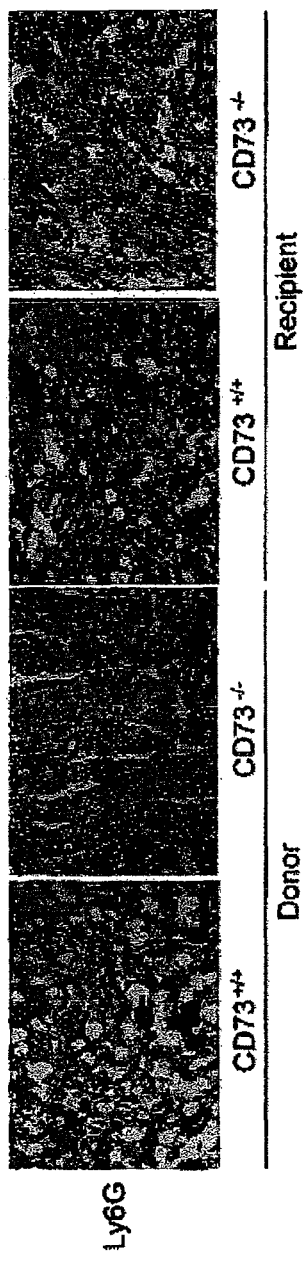
Figure 8E:
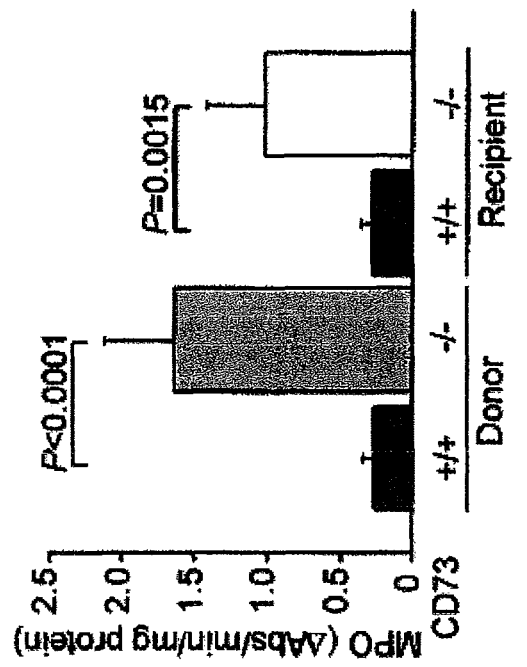
Figure 8D:
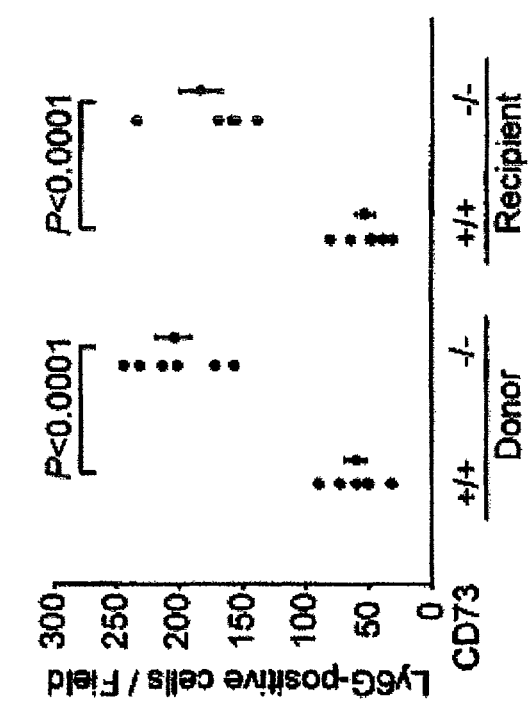

CD73 Deficiency Increases Graft Permeability Following Ischemia/Reperfusion Injury Graft permeability in the ischemia/reperfusion (I/R) phase after transplantation was evaluated. The permeability in cardiac allografts at 4 hours after transplantation was significantly increased in all cases in which CD73 was deficient either in the donor or the recipient (FIG. 8B). These data indicate that there is an important role for CD73 in circulating cells, as well as cells resident in or surrounding the cardiac graft. Next evaluated, was the extent of the neutrophil infiltration using immunohistochemical Ly6G staining for direct neutrophil detection and a MPO activity assay. Compared with experiments in which CD73 was present in either donors or recipients, both the number of graft-infiltrating Ly6G-positive cells and the intragraft MPO activity were significantly increased in grafts involving CD73$^{-/-}$ mice (donors or recipients) (FIG. 8C, D, E).

CD73 Deficiency Accelerates Acute Graft Rejection

Figure 9A:
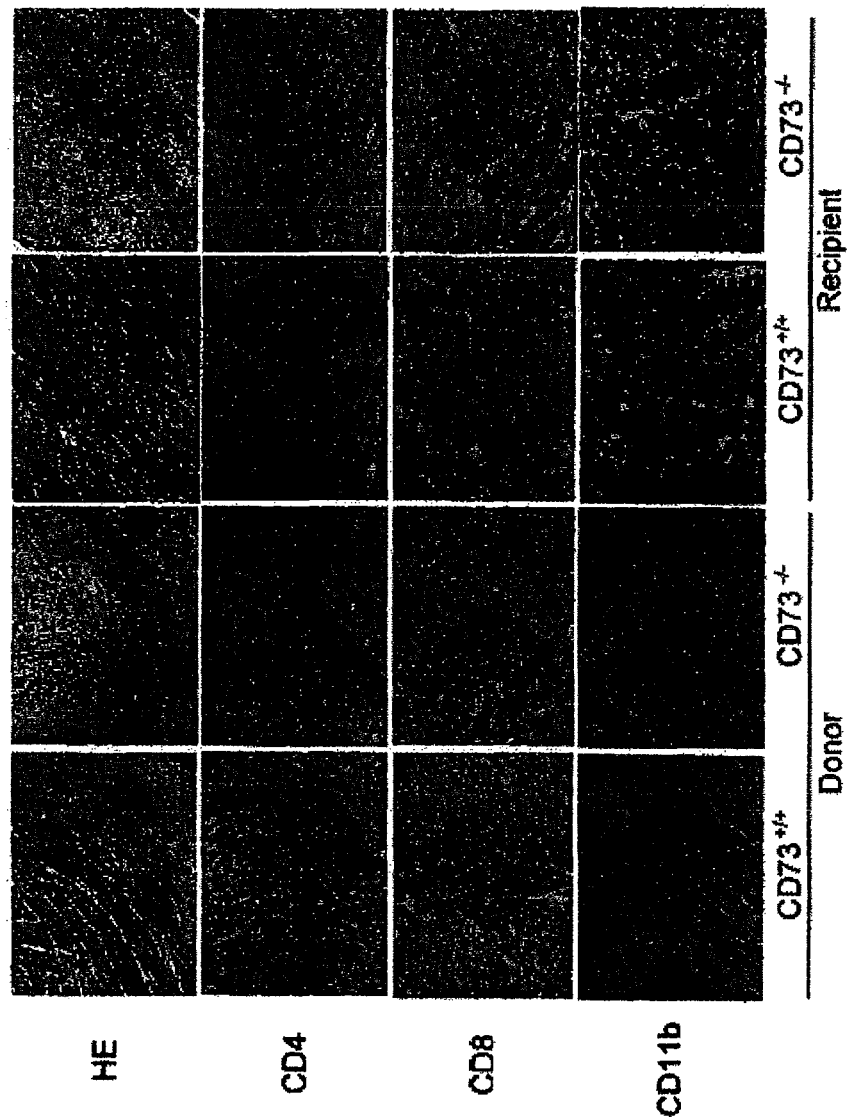
FIGS. 9A, 9B, 9C, 9D, and 9E: Effects of CD73 on histological findings of cardiac allografts at day 7 post-transplantation. (A) Hematoxylin-eosin (HE) staining and immunohistochemical staining (CD4, CD8 and CD11b) in cardiac allografts. Bar=100 μm. (B) PR (parenchymal rejection) score. (C) Quantitative analysis of CD4-positive cells, (D) CD8-positive cells and (E) CD11b-positive cells. All data are expressed as mean±SEM for n=6 mice.
Figure 9B:
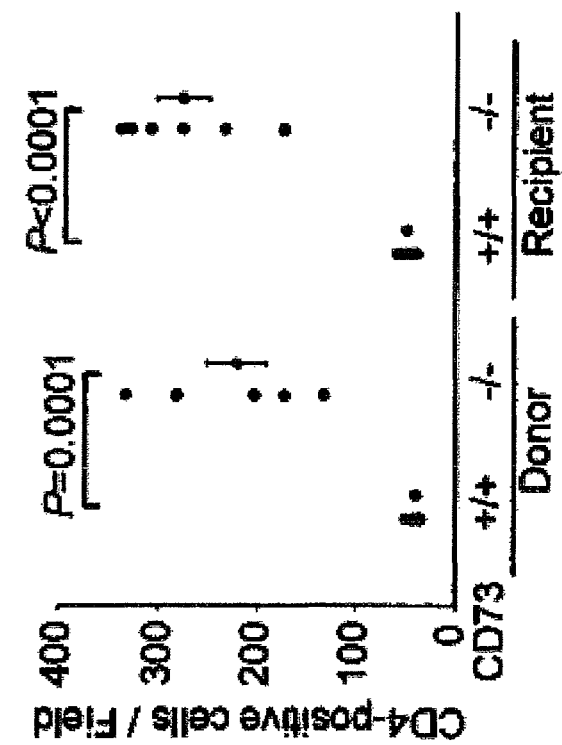
Figure 9C:
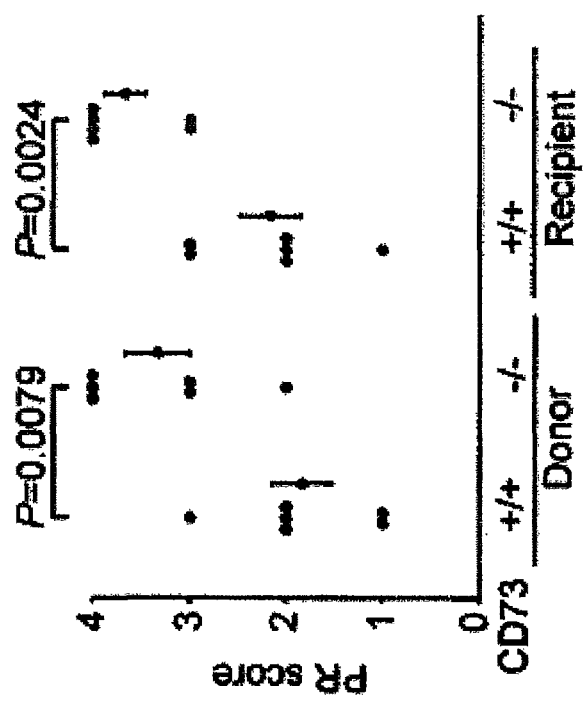
Figure 9D:
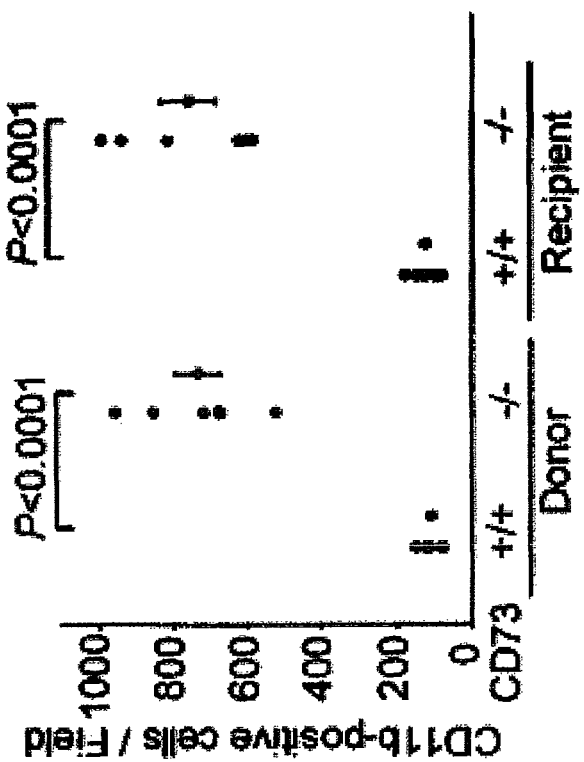
Figure 9E:
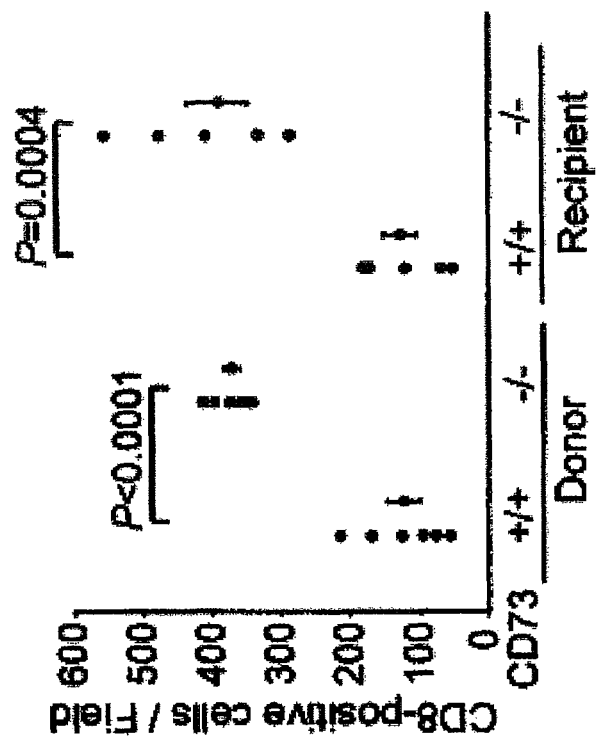

At day 7 post-transplantation, we examined the histology of cardiac allografts to evaluate the acute alloimmune response (FIG. 9A). Infiltration of mononuclear or polymorphonuclear cells with associated cardiomyocyte damage which was greater and more diffuse, and the PR scores significantly higher, in allografts involving CD73$^{-/-}$ versus CD73$^{+/+}$ donors or recipients (FIG. 9B). The numbers of infiltrating CD4-, CD8-, and CD11b-positive cells were significantly increased in experiments involving the transplantation of CD73$^{-/-}$ donors or recipients (FIG. 9C, D, E).

Figure 10:
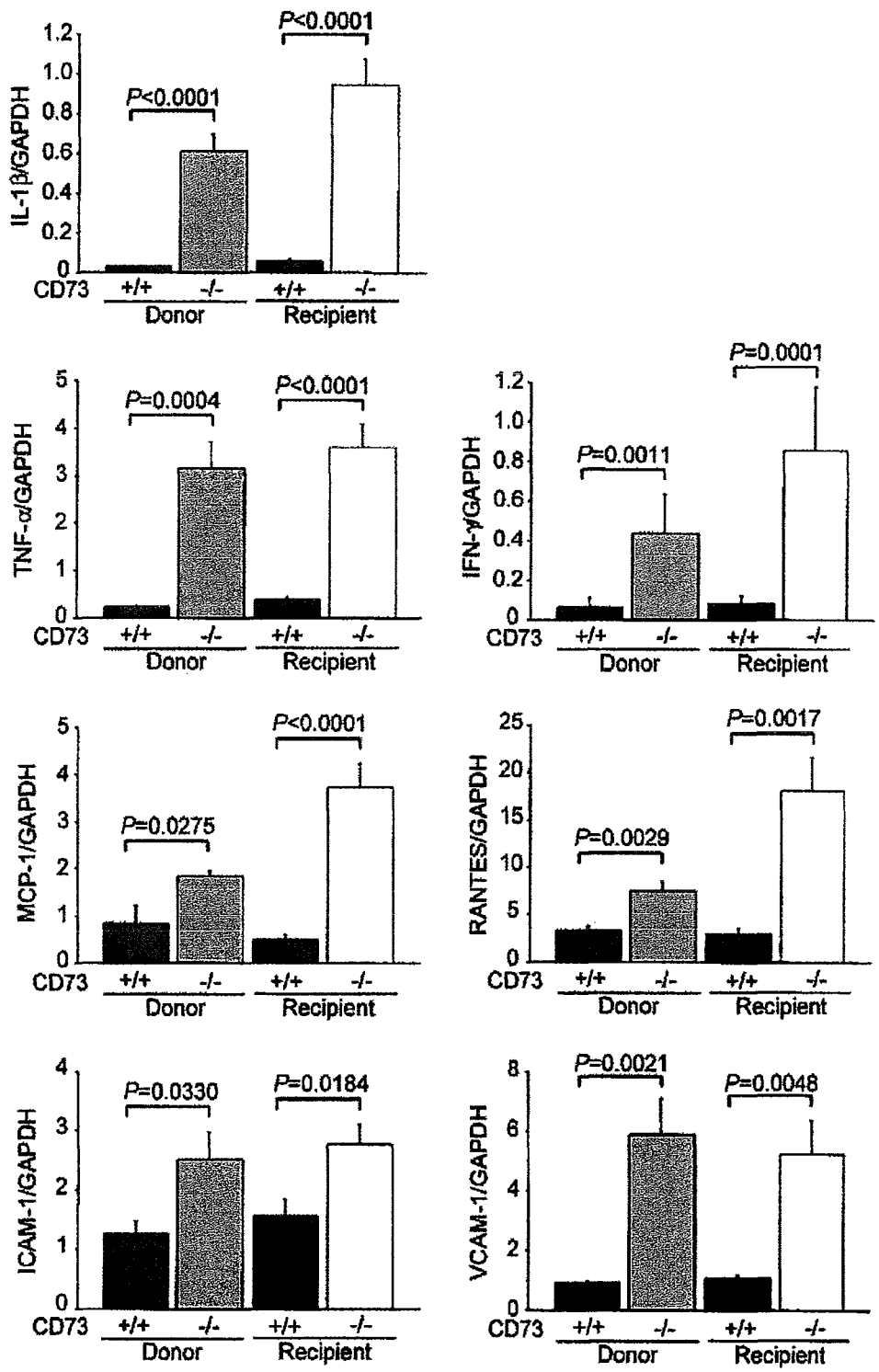
FIG. 10: Effects of CD73 on inflammatory molecules in cardiac allografts at day 7 post-transplantation. Intragraft mRNA expression of cytokines (IL-1β, TNF-α, IFN-γ), chemokines (MCP-1, RANTES) and adhesion molecules (ICAM-1, VCAM-1). All data are expressed as mean±SEM for n=6 mice.

CD73 Deficiency Increases Graft Expression of Cytokines, Chemokines and Adhesion Molecules At day 7 post-transplantation, we examined whether CD73 expression could modulate the mRNA expression of interleukin-1β (IL-1β), tumor necrosis factor-α (TNF-α), interferon-γ (IFN-γ), monocyte chemoattractant protein-1 (MCP-1), regulated on activation normal T cell expressed and secreted (RANTES), intercellular adhesion molecule-1 (ICAM-1) and vascular cell adhesion molecule-1 (VCAM-1) in cardiac allografts. Compared with the CD73$^{+/+}$ transplantations, mRNA expression of each of the above genes were significantly increased in the grafts involving CD73$^{-/-}$ donors or recipients (FIG. 10).

CD73 Deficiency Aggravates Cardiac Allograft Vasculopathy and Graft Tolerance

Figure 11A:
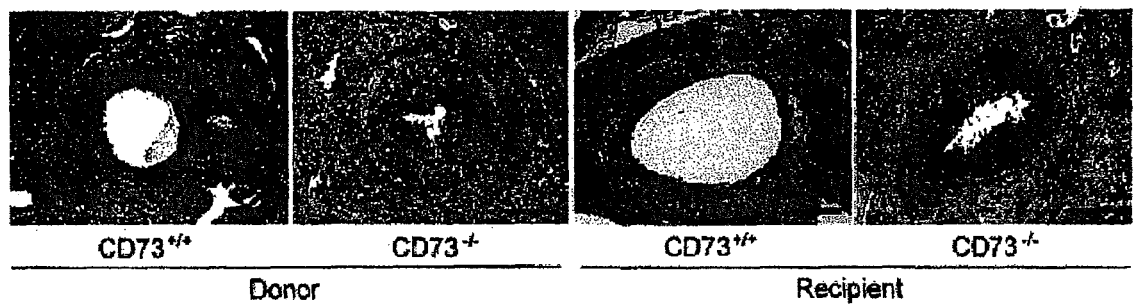
FIGS. 11A, 11B, 11C, and 11D: Effects of CD73 on chronic allograft rejection at day 60 post-transplantation. (A) Elastic staining in cardiac allografts. Bar=100 μm. (B) Histomorphometrical quantification of luminal occlusion in graft coronary arteries. (C) Donor-reactive alloantibodies in recipient serum. NC, negative control. (D) Cell proliferation of recipient lymphocytes in one-way MLR (mixed lymphocyte reaction) ex vivo. CD73$^{+/+}$, C57BL/6 (CD73$^{+/+}$) T-lymphocytes; CD73$^{-/-}$, C57BL/6 (CD73$^{-/-}$) T-lymphocytes; B10A, B10A T-lymphocyte. All data are expressed as mean±SEM for n=6 mice.
Figure 11B:
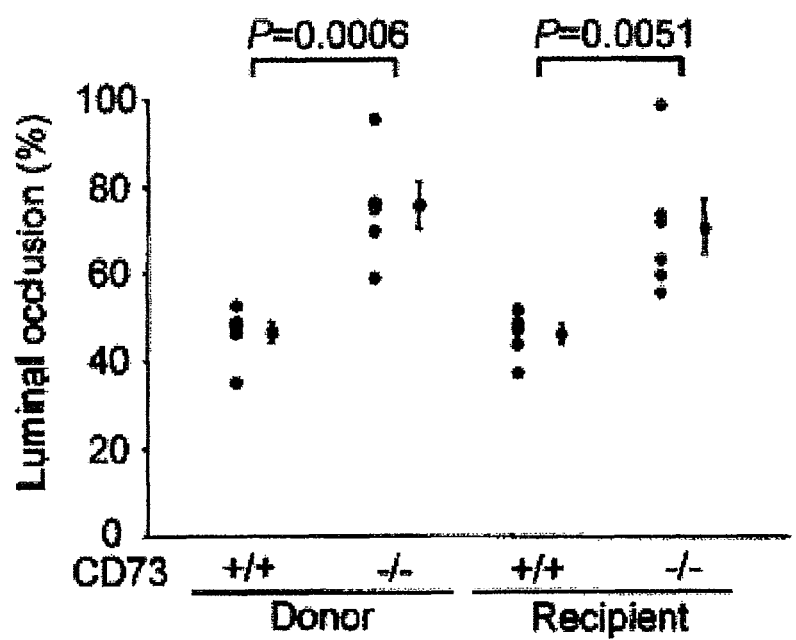
Figure 11C:
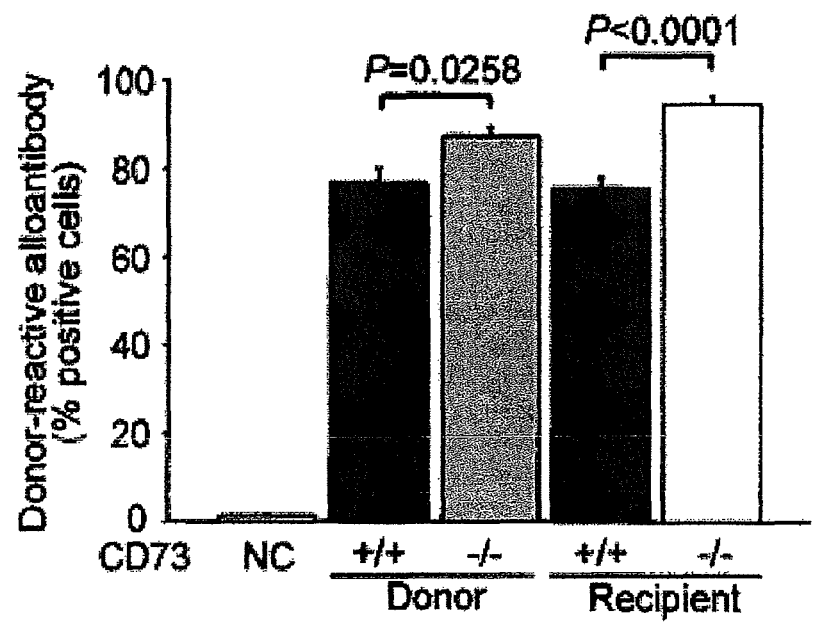
Figure 11D:
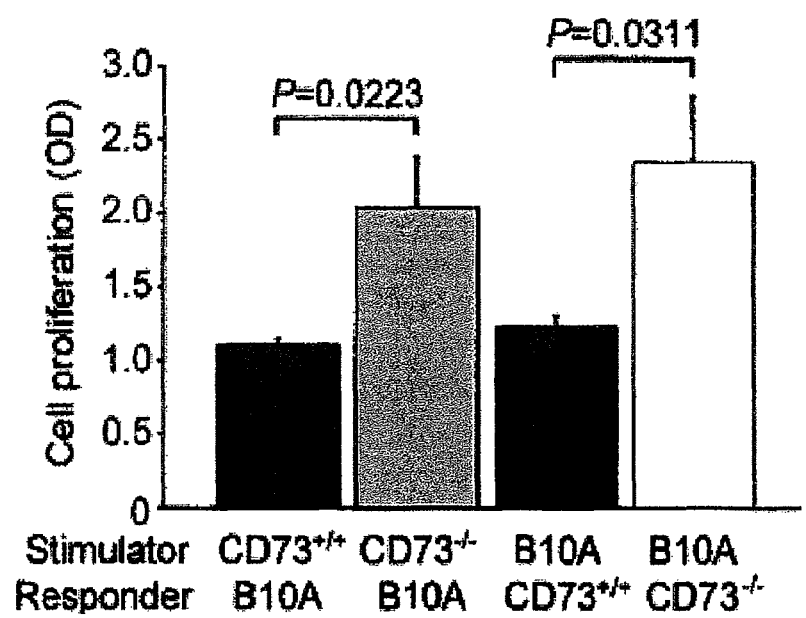

To evaluate the severity of CAV development, we examined the histology of cardiac allografts at day 60 post-transplantation using elastin-stained tissue sections (FIG. 11A). Compared with CD73$^{+/+}$ transplantations, the severity of luminal occlusion in the graft coronary arteries involving CD73$^{-/-}$ donors or recipients was significantly increased (75.9±5.4 vs. 46.6±2.5% and 70.5±6.5 vs. 46.1±2.0%, P=0.0006 and P=0.0051, respectively; FIG. 11B). Next, we investigated the impact of CD73 expression on humoral immunity in chronic rejection. CD73 deficiency in donors or recipients resulted in significantly higher levels of donor-reactive alloantibodies in the chronic rejection phase than in transplants between CD73$^{+/+}$ donors and recipients (FIG. 11C). To further assess the effect of CD73 expression on recipient anti-donor cellular immune responsiveness, we evaluated cell proliferation of recipient lymphocytes using an ex vivo one-way MLR. The cell proliferation was significantly amplified in the transplantation of CD73$^{-/-}$ donors or recipients (FIG. 11D).

Intragraft Expression of CD73 as it Relates to Adenosine Receptor Expression

Figure 12A:
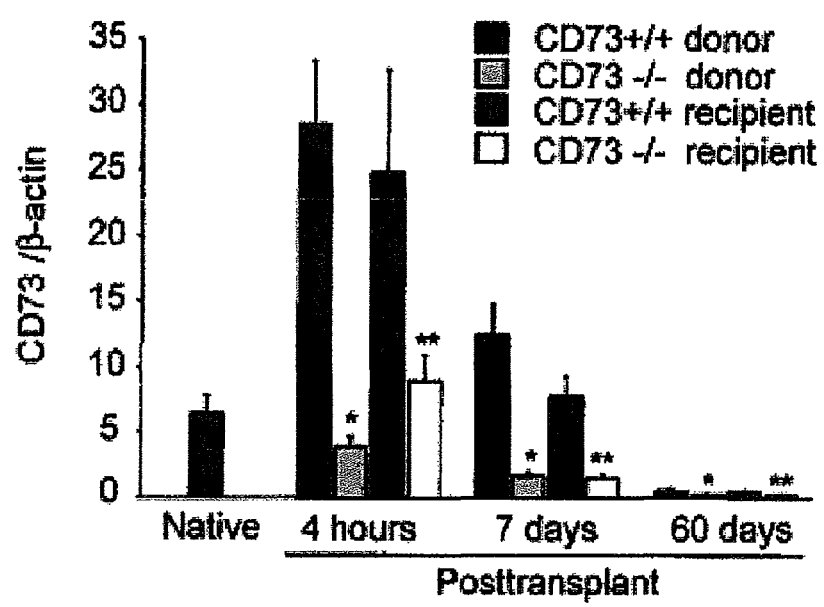
FIGS. 12A, 12B, 12C, and 12D: Intragraft expression of CD73 and ARs (adenosine receptors) throughout post-transplantation. (A) mRNA expression of CD73 and (B) ARs ($A_1AR$, $A_{2A}AR$, $A_{2B}AR$ and $A_3AR$). *$P<0.05$ vs. CD73$^{+/+}$ donor, **$P<0.05$ vs. CD73$^{+/+}$ recipient, †$P<0.05$ vs. native heart. (C) Protein expression of CD73, $A_{2B}AR$ and. $A_3AR$ by Western blotting at 4 hours and (D) 7 days after transplantation. The expression of each band was normalized to its corresponding β-actin band. All data are expressed as mean±SEM for n=6 mice.
Figure 12B:
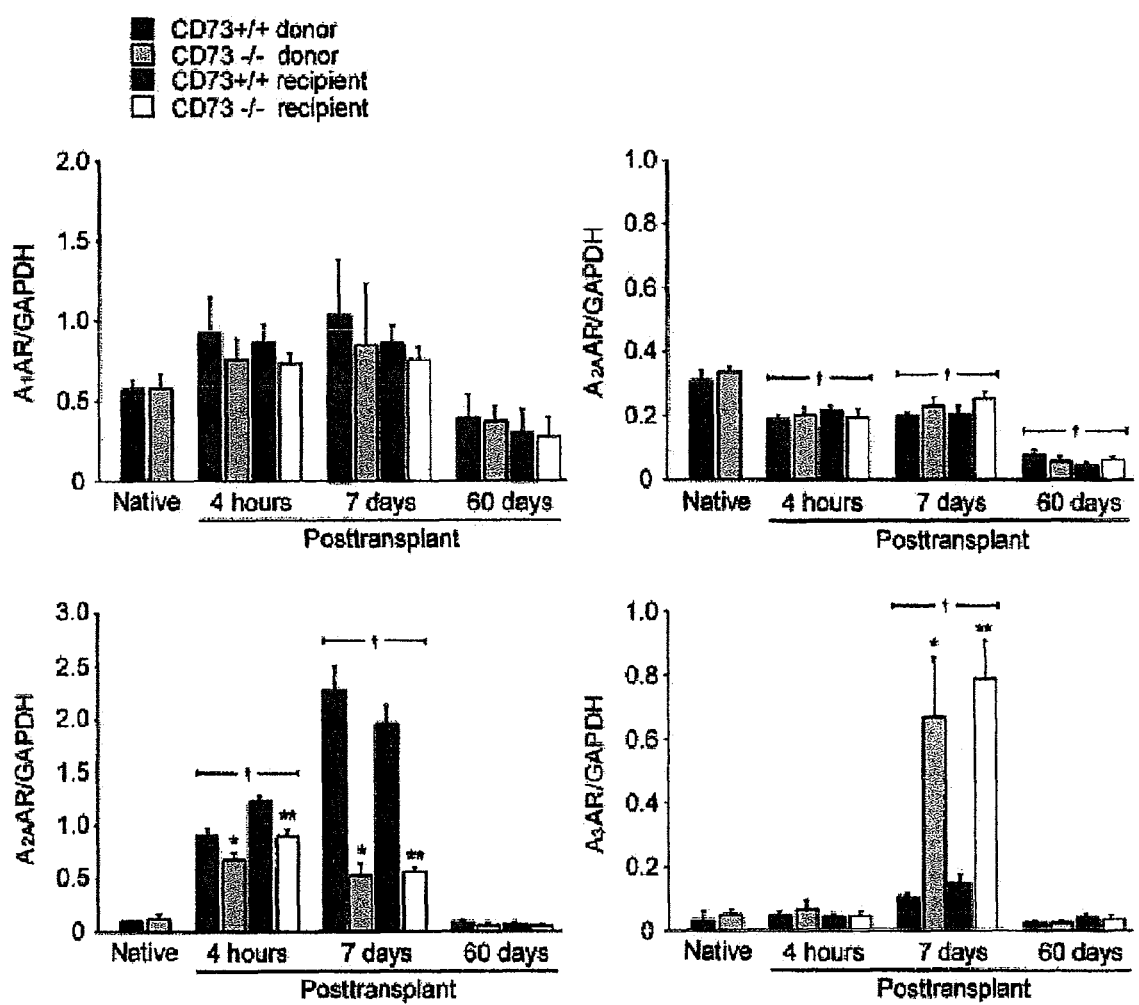
Figure 12C:
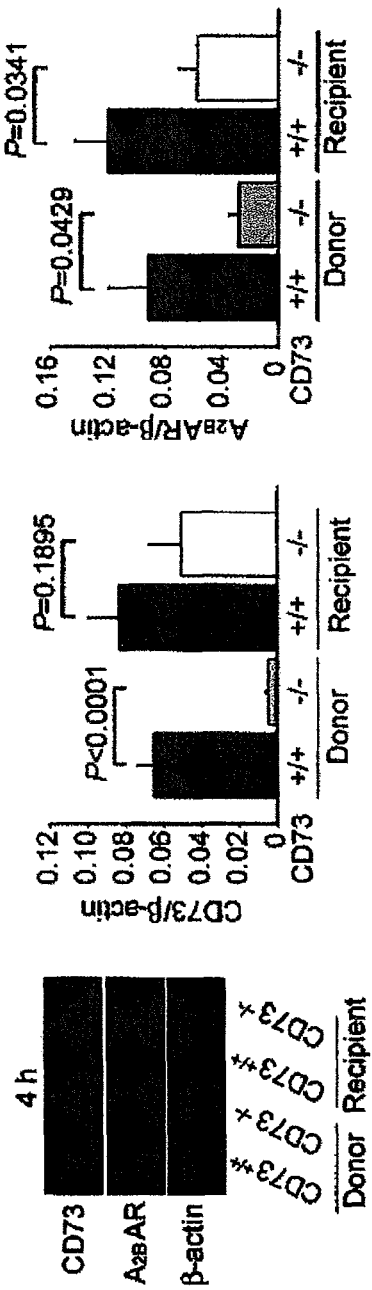
Figure 12D:
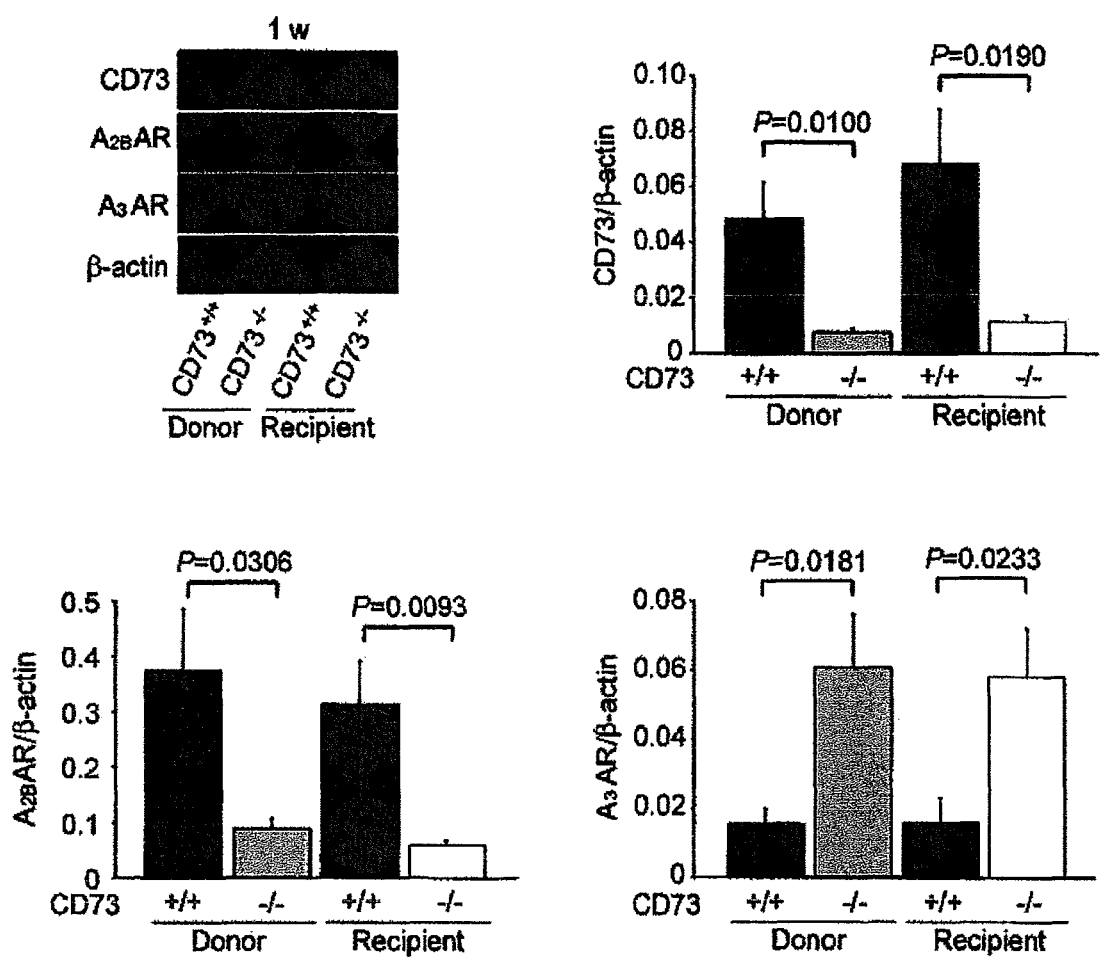

After cardiac transplantation, recipient circulating cells infiltrate into allografts, thereby promoting the graft injury during the I/R phase and the phases of acute and chronic rejection. To elucidate: the impact of CD73 expression in cardiac allografts, we measured mRNA and protein levels of CD73 in allografts at 4 hours, 7 days and 60 days after transplantation (FIGS. 12A, C, D). In CD73$^{+/+}$ donors or recipients, CD73 mRNA expression in cardiac allografts was markedly upregulated at 4 hours post-transplantation, upregulated but attenuated at day 7, and finally downregulated at day 60 post-transplantation. CD73$^{-/-}$ donors or recipients had lower levels of CD73 mRNA in all phases post-transplantation. Because extracellular adenosine produced by CD73 can signal through any of 4 ARs ($A_1AR$, $A_{2A}AR$, $A_{2B}AR$ or $A_3AR$), we next measured mRNA and protein levels of each AR in each phase after transplantation (FIGS. 12B, C, D). Intragraft $A_{2B}AR$ expression was upregulated in all groups at 4 hours and 7 days after transplantation, though CD73$^{-/-}$ donors or recipient groups had significantly lower levels of upregulation when compared to the CD73$^{+/+}$ groups. At day 7 post-transplantation, intragraft $A_3AR$ expression was significantly upregulated in all groups, though CD73$^{-/-}$ donor or recipient groups showed significantly more upregulation of $A_3AR$, compared with CD73$^{+/+}$ groups. Although intragraft $A_{2A}AR$ mRNA expression was significantly downregulated throughout post-transplantation, there was no significant difference between the CD73$^{+/+}$ and CD73$^{-/-}$ groups.

Figure 13A:
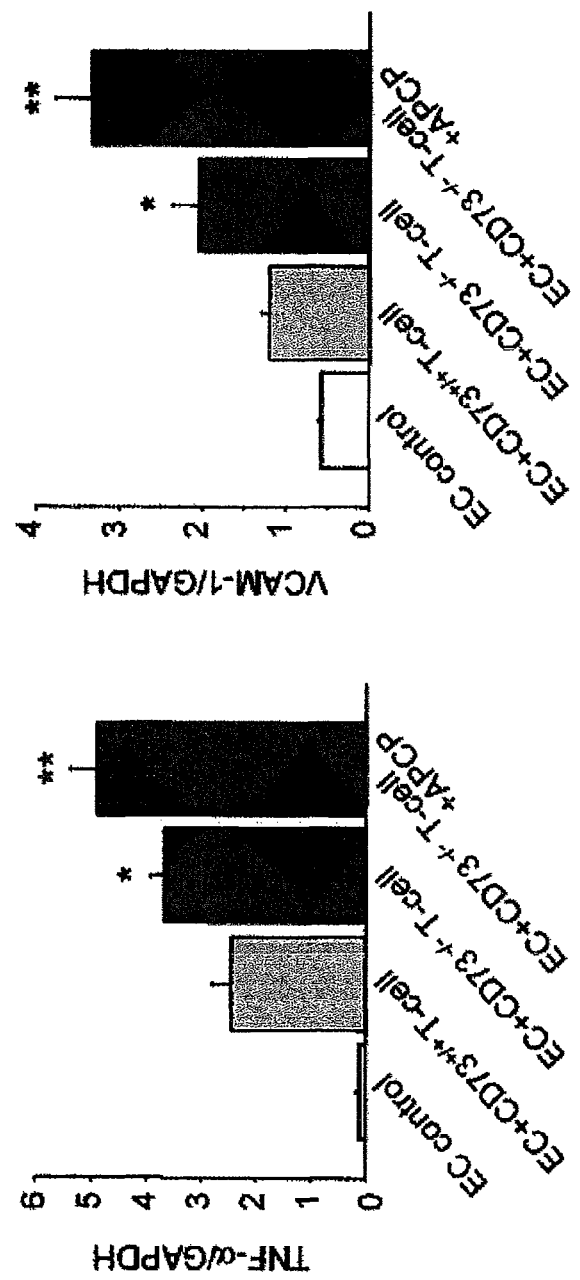
FIGS. 13A, 13B, and 13C: Allomismatched coculture of endothelial cells (ECs) and T lymphocytes in vitro. (A) endothelial mRNA expression of TNF-α and VCAM-1 in the simple coculture. *P<0.05 vs. EC+CD73$^{+/+}$ cell, **P<0.05 vs. EC+CD73$^{-/-}$ T cell (by ANOVA) (B) Trans-endothelial migration of T-lymphocytes in the transmigration coculture. *P<0.05 vs. CD73$^{+/+}$ cell+EC, **P<0.05 vs. CD73$^{4-}$ Tcell+EC (by ANOVA) (C) IFN-γ mRNA expression in T lymphocytes in the transmigration coculture. †P<0.05 vs. pre-transmigrated T-lymphocytes in each group, *P<0.05 (by ANOVA) vs. CD73$^{+/+}$ Tcell+EC. All data are expressed as mean±SEM for 6 independent analyses. EC, endothelial cell; Tcell, T lymphocyte.
Figure 13B:
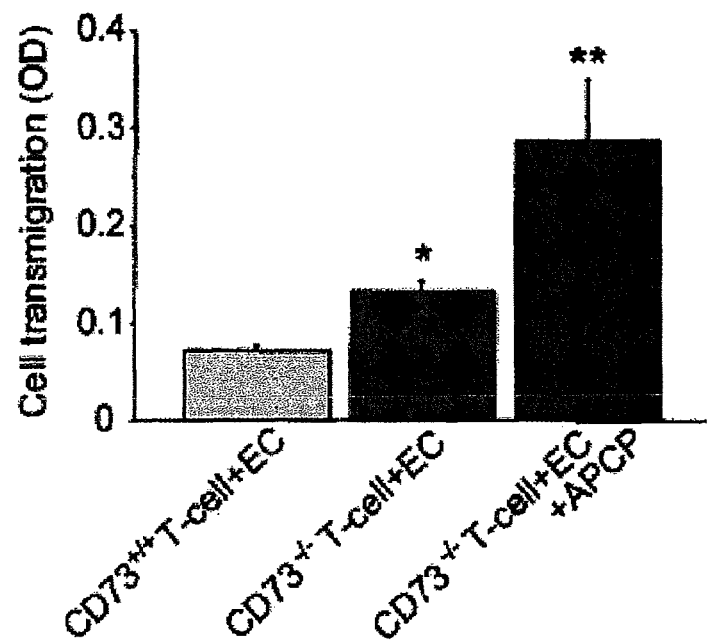
Figure 13C:
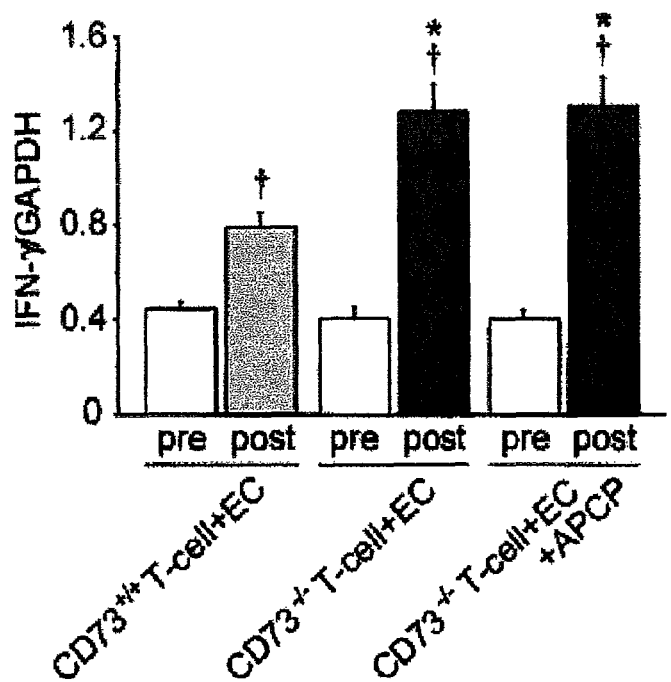

Genetic Deletion or Pharmacological Blockade of CD73 Promotes Activation of Endothelial Cells and T Lymphocytes In Vitro To further elucidate the effects of CD73 on interactions between endothelial cells and T lymphocytes found in cardiac allografts, we performed an allomismatched coculture of endothelial cells (H-2$^d$) and lymphocytes (H-2$^b$; CD73$^{+/+}$ or CD73$^{-/-}$) with or without APCP in vitro. First, we evaluated the contribution of T lymphocytes to endothelial cells on the simple coculture experiments. After a 72-h coculture, mRNA expressions of endothelial cell TNF-α and VCAM-1 were significantly upregulated in the coculture with CD73$^{-/-}$ T-lymphocytes as compared with CD73$^{+/+}$ T-lymphocytes (P=0.0195 and P=0.0270, respectively; FIG. 13A). The addition of APCP significantly enhanced these upregulations in the coculture with CD73$^{-/-}$ T-lymphocytes (TNF-α and VCAM-1, P=0.0436 and P=0.0329, respectively; FIG. 13A). Next, we evaluated the contribution of endothelial cells to T lymphocytes utilizing transmigration coculture experiments. After a 24-h coculture, the number of T-lymphocytes that had transmigrated into endothelial cells significantly increased in CD73$^{-/-}$ T-lymphocytes compared to CD73$^{+/+}$ T-lymphocytes (P=0.0004; FIG. 13B), and APCP significantly enhanced the transmigration in the coculture of CD73$^{-/-}$ T-lymphocytes (P=0.0353; FIG. 13B). IFN-γ mRNA expression in the post-transmigrated T-lymphocytes was significantly upregulated in all experimental groups when compared to pretransmigrated T-lymphocytes, and the IFN-γ mRNA upregulation was significantly higher in the coculture of CD73$^{-/-}$ T-lymphocytes compared with the coculture of CD73$^{+/+}$ T-lymphocytes (P=0.0042; FIG. 13C). There was no significant enhancement of the IFN-γ mRNA upregulation when APCP was added to the coculture of CD73$^{-/-}$ T-lymphocytes.

Influence of Exogenous Adenosine Receptor Modulators on Cardiac Transplantation

Figure 14A:
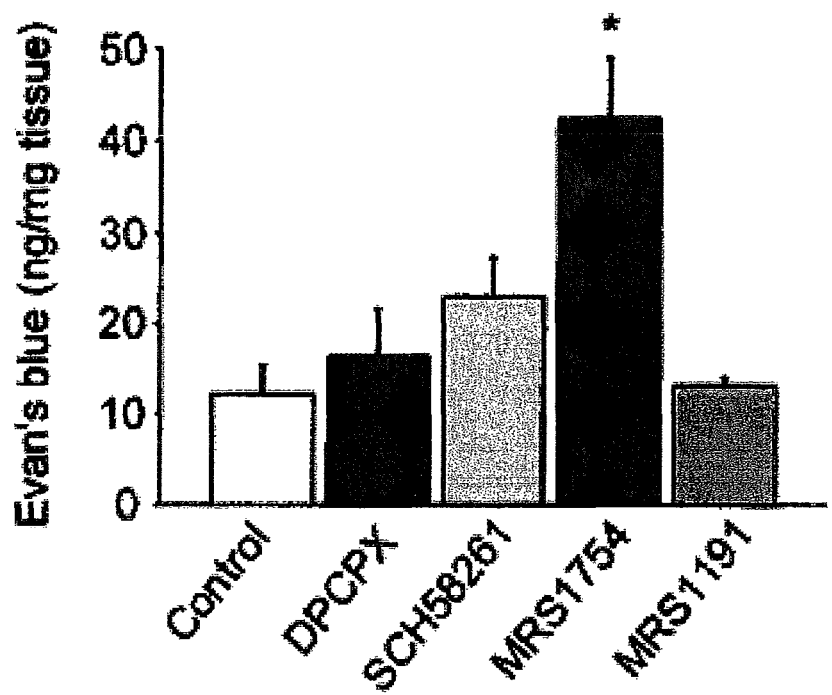
FIGS. 14A, 14B, 14C, and 14D: Effects of AR modulators on cardiac allografts. (A) Graft permeability at 4 hours after CD73$^{+/+}$ transplantation following an administration of AR antagonists (DPCPX, SCH58261, MRS1754 and MRS1191). *P<0.05 (by ANOVA) vs. Control. (B) Graft survival following an administration of A$_2$AR agonists (CGS21680 and NECA). *P<0.05 (by ANOVA) vs. CD73$^{+/+}$ non-treatment, †P<0.05 vs. CD73$^{+/+}$ with CGS21680, ††P<0.05 vs. CD73$^{-/-}$ with CGS21680. (C, D) Effects of A$_{2B}$AR agonist (NECA) on chronic allograft rejection at day 30 post-transplantation. Elastic staining in cardiac allografts (C) and histomorphometrical quantification of luminal occlusion in graft coronary arteries (D). Bar=100 µm. a, donor CD73$^{+/+}$+no treatment; b, donor CD73$^{+/+}$+NECA; c, donor CD73$^{-/-}$+NECA; d, recipient CD73$^{+/+}$+no treatment; e, recipient CD73$^{+/+}$+NECA; f, recipient CD73$^{-/-}$+NECA. Data are expressed as mean±SEM for n=4 (A) and n=6 (B, C, D) mice.
Figure 14B:
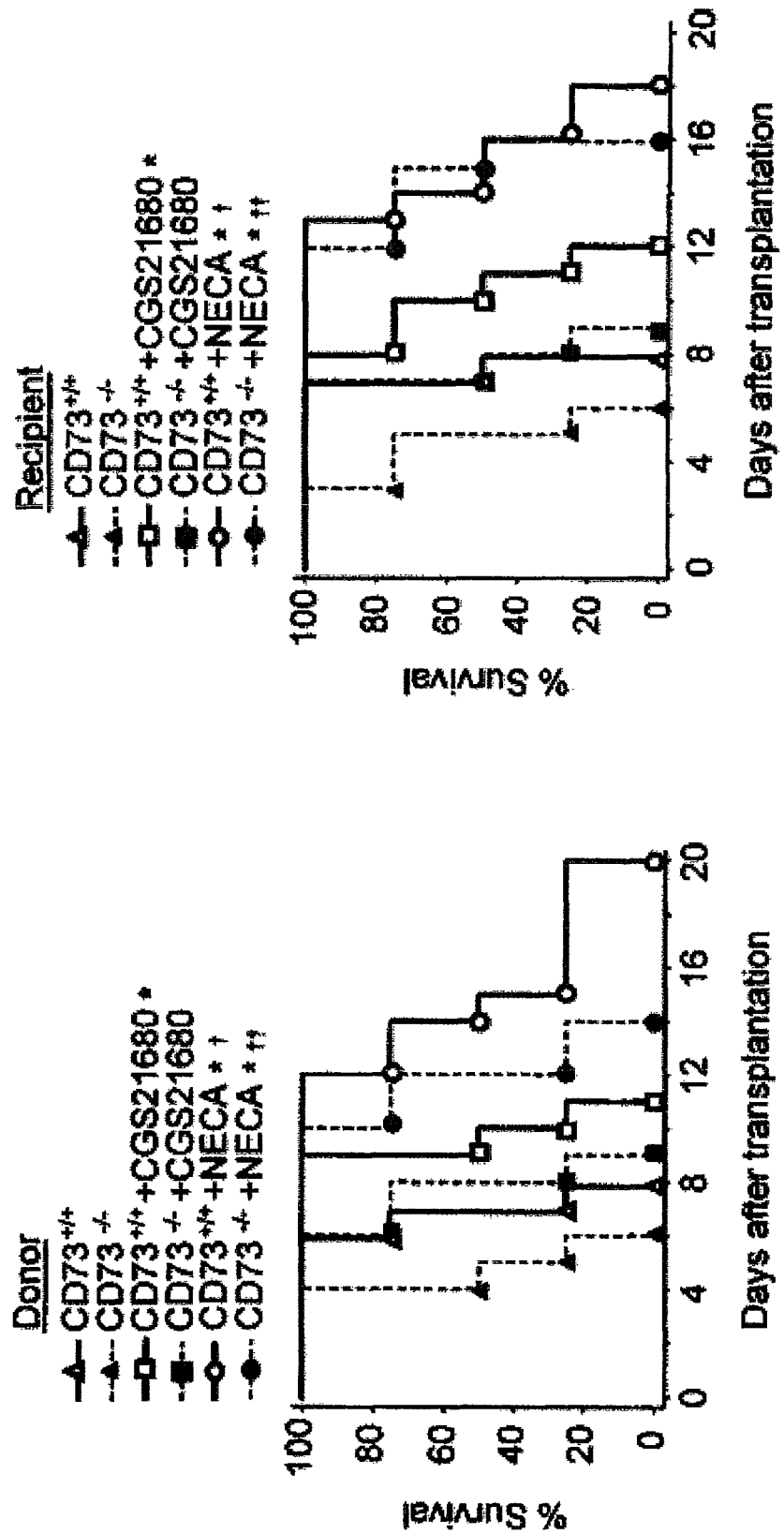
Figure 14D:
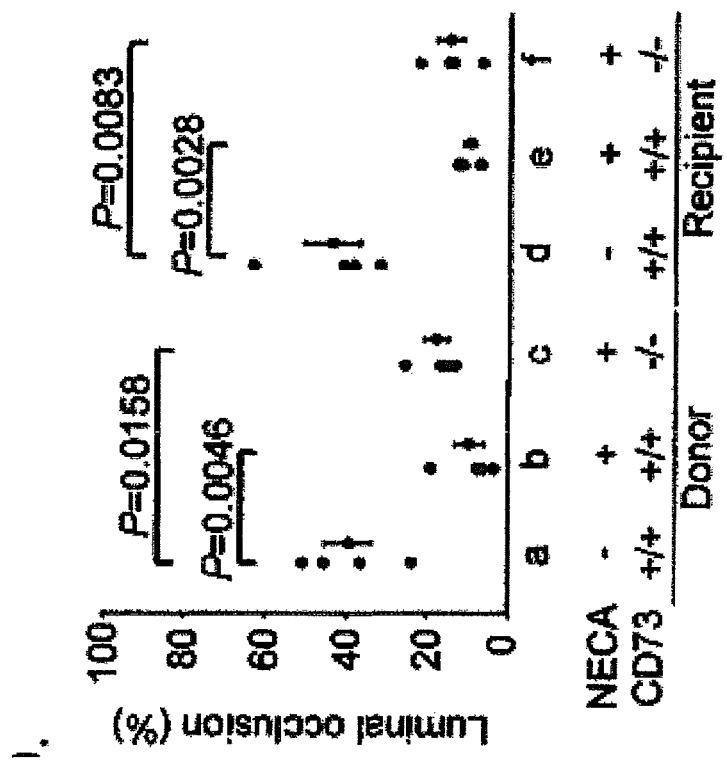
Figure 14C:
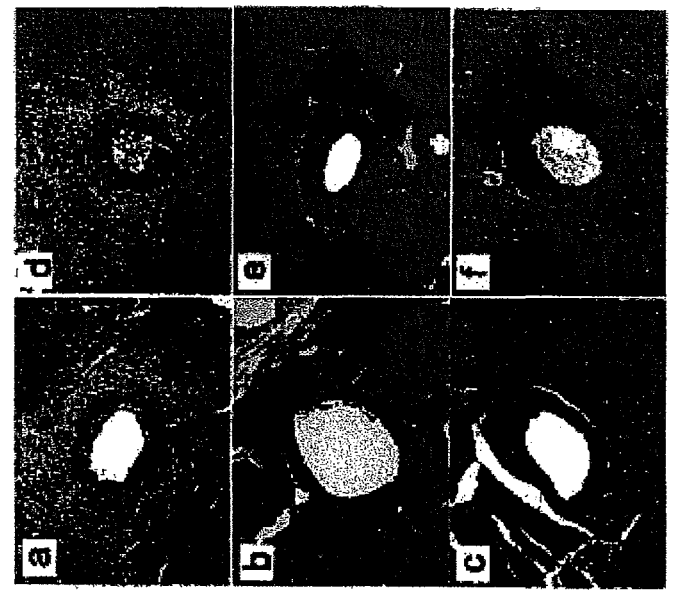

To further evaluate the CD73-mediated contribution of specific AR subtypes during allograft rejection or CAV, we performed heterotopic cardiac transplantation using AR modulators given intraperitoneally. First, we examined which AR is acutely responsible for increased vascular leakage in the murine heterotopic cardiac transplantation model. At 4 hours after transplantation, graft permeability tended to increase for each AR antagonist applied ($A_{2B}$, MRS1754>$A_{2A}$, SCH58261>$A_1$, DPCPX>$A_3$, MRS1191), though only the $A_{2B}AR$ antagonist MRS1754 caused a statistically significant increase in vascular leakage (P<0.0001 vs non-treatment control by ANOVA; FIG. 14A). Based on the results of this graft permeability assay, we selected $A_2AR$ agonists ($A_{2A}$, CGS21680; $A_{2B}$, NECA) to establish their potential effects on cardiac allograft rejection or vasculopathy. Both CGS21680 and NECA treatments significantly increased graft survival compared with non-treatment controls, though the survival in NECA-treated recipients was significantly longer than that in CGS21680-treated recipients. When CD73$^{-/-}$ donors or recipients were studied, NECA treatment significantly increased graft survival compared with wild-type non-treatment controls, whereas there was no significant increase in survival between CGS21680 treatment and wild-type non-treatment (FIG. 14B). The next set of experiments was designed to measure the role of the $A_{2B}AR$ in CAV. In both CD73$^{+/+}$ and CD73$^{-/-}$ donors or recipients, the severity of luminal occlusion at day 30 post-transplantation was significantly attenuated by NECA treatment, compared with wild-type non-treatment controls (FIG. 14C,D). Taken together, these data suggest that $A_{2B}AR$ strongly contributes to CD73-mediated allograft protection in murine heterotopic cardiac transplantation.

Summary/Heart Transplant

Ecto-5'-nucleotidase (CD73) catalyzes the terminal phosphohydrolysis of 5'-adenosine monophosphate, and is widely expressed on endothelial cells where it regulates barrier function. As it is also expressed on lymphocytes, we hypothesized that it modulates vascular immune regulation under homeostatic conditions and dysregulation under stress conditions such as cardiac allotransplantation. In a heterotopic cardiac allotransplantation model, CD73 deficiency in either donors or recipients resulted in decreased graft survival and the development of cardiac allograft vasculopathy (CAV), suggesting a contribution of CD73 on both graft-resident and circulating cells in vasculopathy pathogenesis. Vascular perturbations incited by lack of CD73 included loss of graft barrier function, and diminished graft expression of the $A_{2B}$ adenosine receptor ($A_{2B}AR$), with a concordant exacerbation of the acute inflammatory and immune responses. The importance of CD73 in modulating endothelial-lymphocyte interaction was further demonstrated in allomismatched in vitro coculture experiments. Either genetic deletion or pharmacological blockade of CD73 increased transendothelial lymphocyte migration and inflammatory responses, suggesting that CD73 plays a critical role to suppress transendothelial leukocyte trafficking through its enzymatic activity. In addition, antagonism of $A_{2B}AR$ caused a significant increase in vascular leakage, and agonism of $A_{2B}AR$ resulted in marked prolongation of graft survival and suppression of CAV development. These data suggest a new paradigm in which phosphohydrolysis of adenosine monophosphate by CD73 on graft-resident or circulating cells diminishes transendothelial leukocyte trafficking and mitigates inflammatory and immune sequelae of cardiac transplantation via the $A_{2B}AR$.

Example 3

Cerebrovascular Ischemia; Endothelial Ecto-5' Nucleotidase (CD73) Regulation of Leukocyte Trafficking in the Ischemic Brain Methods All reagents, unless stated otherwise, were obtained from Sigma (St. Louis, Mo., USA).

CD73-deficient mice (CD73$^{-/-}$), were as described above. Wild-type C57Bl/6J mice were purchased from Jackson Laboratory (Bar Harbor, Me., USA) and used as controls.

Photothrombotic Model of Cerebral Ischemia

Permanent occlusion of middle cerebral artery (MCAO) was induced using a technique wherein a laser light was applied on the middle cerebral artery after the mouse had received an intravenous injection of a photoreactive material.

Ten week old male mice were anesthetized with 2.5 mg intraperitoneal ketamine and 0.25 mg xylazine (Phoenix Pharmaceutical). Body temperature was at 37° C. maintained during surgery and for 45 minutes thereafter using a temperature controlled circulating liquid heating pad. After opening an oval bony window, 2-3 mm in diameter using a dental drill (Foredom electric company, U.S.A), the distal part of left middle cerebral artery (MCA) was exposed. A laser Doppler flow probe (Type N, 18 gauge, Transonic Systems, Ithaca, N.Y.) was attached to the surface of the cerebral cortex located 1.5 mm dorsal median to the bifurcation of the distal MCA. The probe was connected to a flow meter (Transonic model BLF21) and flow recorded with a continuous data acquisition program (Windaq, DATAQ Instruments). Rose Bengal was diluted to 10 mg/ml in PBS and injected intravenously, to achieve a final concentration of 40 mg/kg of body weight. A 1.5 mW green neon laser (540 nm, Melles Griot) was directed at the MCA from a distance of 6 cm, and occlusion monitored by the cerebral blood flow probe. Occlusion was defined as a >80% reduction in blood flow for approximately 10 minutes. After obtaining stable occlusion, the laser remained in place for 15 additional minutes. In a subset of experiments $CD73^{-/-}$ and WT mice were injected intraperitoneally, with 7.5 U of soluble 5'nucleotidase purified from *Crotalus atrox* venom, given 30 minutes before induction of brain ischemia, while their controls were injected with the same amount of saline.

Magnetic Resonance Imaging

Infarct volumes were measured using magnetic resonance imaging and performed by the University of Michigan Small Animal Imaging Resource forty-eight hours after induction of brain ischemia. Throughout the MRI scanning procedure, mice were anesthetized with 2% isoflurane/air mixture. Mice were positioned prone, head first, in a 7.0T Varian MR scanner (183 mm horizontal bore, Varian, Palo Alto, Calif.), with their body temperature maintained at 37° C., using circulated heated air. A double-tuned volume radiofrequency coil was used to scan the head region of the mice. Axial T2-weighted images were acquired using a spin-echo sequence, using the following parameters: repetition time (TR)/effective echo time (TE), 4000/40 ms; field of view (FOV), 30×30 mm; matrix, 256×256 slice thickness, 0.5 mm; slice spacing, 0 mm; number of slices, 25; and number of scans, 1 (total scan time 8 min.). Cerebral infarct volumes were quantified at 48 hours.

Neurologic Deficit Scoring

Forty-eight hours after stroke, mice were assessed for neurological deficit using a previously described a 5-tiered grading system (6), with measurements performed by an observer blinded to experimental conditions. A score 1 was given if the animal demonstrated normal spontaneous movement; a score 2 was given if the animal was circling clockwise when viewed from above while receiving a mildly noxious stimuli (tail pinch); a score 3 was given if the animal was observed to spin clockwise on a longitudinal axis including the tail; a score of 4 was given to the animal fell down on the contralateral side; a score of 5 was given if the animal was crouched on all four paws unresponsive to noxious stimuli.

Brain Water Content

A separate cohort of mice not undergoing infarct volume or leukocyte trafficking measurements were euthanized, brains were removed rapidly, and divided into ischemic and nonischemic hemispheres. The samples were weighed and then dried at 95° C. for 24 hours to obtain the dry weight. The brain water content was calculated as (wet weight-dry weight)/dry weight.

Flow Cytometric Analysis of Inflammatory Cells

Forty-eight hours after surgery the mice were euthanized, the brains were removed and divided into ischemic and non-ischemic hemispheres. The cerebral hemispheres were then minced with the scalpel and the tissue pieces repeatedly aspirated with a syringe (18 gauge needle) to obtain single cell suspensions. A Percoll (GE Healthcare, Piscataway, N.J., USA) gradient was then used for separation of infiltrating cells, with discard of the myelin fractions and residual debris. FACs Lysis Buffer (BD, Franklin Lakes, N.J., USA) was used to lysed red blood cell contaminants. Prior to flow cytometric analyses, live cells were counted using a hemocytometer and distinguished from dead cells by the absence of propidium iodide (BD) staining. Nonspecific antibody binding was blocked using Fc Block (BD). Cell populations were purified and identified in three stages. First, the leukocyte/microglia population fraction of cells was isolated using an antibody to a common leukocyte antigen (CD45). Subfractionation of this population of cells was accomplished using an anti-LY-6G antibody. Resulting cell subpopulations were therefore characterized according to the level of expression of both markers: $CD45^{hi}LY6\text{-}G^{hi}$ represents neutrophils; $CD45lowLY6\text{-}G^{-ve}$ represents microglia; and $CD45^{hi}LY\text{-}6G^{-ve}$ cells were considered to be mononuclear cells. Using CD45-PE antibody (BD) to mark the common leukocyte antigen CD45, leukocytes were separated from other cells within the cerebrum. Cells with high expression of CD45 (CD45hi) were further identified as neutrophils based on FITC-conjugated LY-6G (BD) positivity, or as infiltrating macrophages by high expression of FITC-conjugated F4/80 (Serotec, Raleigh, N.C., USA). Among CD45-bearing cells, cells with low expression of CD45 or F4/80 antibody were considered to be resident microglia. Dead cells were excluded with a propidium iodide gate. All samples were acquired on a FACS-Calibur Flow Cytometer and data was analyzed using CellQuest software (BD).

Bone-Marrow Transplantation

For certain experiments, mice were myeloablated followed by bone marrow reconstitution (7). Ten week old male $CD73^{-/-}$ or wild-type ($CD73^{+/+}$) littermate control mice were irradiated using 12.5 Gy radiation exposure, administered in three doses three hours apart. Mice were re-populated with $CD73^{-/-}$ bone marrow or wild-type bone marrow using approximately $4 \times 10^6$ bone marrow cells administered intravenously. Mice were allowed to recover for eight weeks before induction of brain ischemia and phenotype examination. For these experiments, four types of chimeric animals were generated; $CD73^{-/-}$ mice repopulated with (1) $CD73^{-/-}$ bone marrow to create global knock-out controls or (2) wild-type bone marrow (to create tissue only CD73 deficient mice); wild-type mice reconstituted with (3) wild-type bone marrow (to create wild type controls) or (4) $CD73^{-/-}$ bone marrow (to create mice which lacked CD73 only in their leukocyte). These mice will be denoted using the following abbreviation scheme: Bone Marrow Donor-→Bone Marrow Recipient. Chimeras will be referred to as KO→KO; WT→KO; WT→WT; and KO→WT.

Real-Time Reverse Transcriptase

Real-Time Reverse Transcriptase-Polymerase Chain Reaction (RT-PCR) Assay

Total RNA in brain tissues at 48 hrs after Photothrombotic MCA occlusion was extracted via the RNAzol B method (Tel-Test, Friendswood, Tex., USA). Total RNA was reverse-transcribed into cDNA by using random primers (Life Technologies, Rockville, Md., USA). To detect cerebral levels of MCP-1, interleukin (IL-6), KC, tumor necrosis factor (TNF)-, interleukin (IL)-1β, and VCAM-1 mRNA, real-time RT-PCR was performed by means of an ABI PRISM 7700 sequence detection system with TaqMan Universal PCR Master Mix and Assays-on-Demand gene expression probes (Applied Biosystems, Foster City, Calif., USA). TaqMan Rodent 18S Ribosomal RNA Control Regents VIC (Applied Biosystems) was used as an endogenous control gene. A standard curve for the serial dilution of murine brain cDNA was generated. The amplification cycle consisted of 2 min at 50° C., 10 min at 95° C., 15 s at 95° C. and 1 min at 60° C. Relative quantitative values of targets were normalized according to the endogenous 18S ribosomal RNA gene control.

Statistical Analyses

Values are reported as mean±SEM, with the number of experiments performed provided in the figure legends. The significance of differences between groups with multiple comparisons was estimated by one-way analyses of variance (ANOVA) followed by Newman-Keuls test. Statistical significance was confirmed at $p<0.05$.

Results

Figure 15:
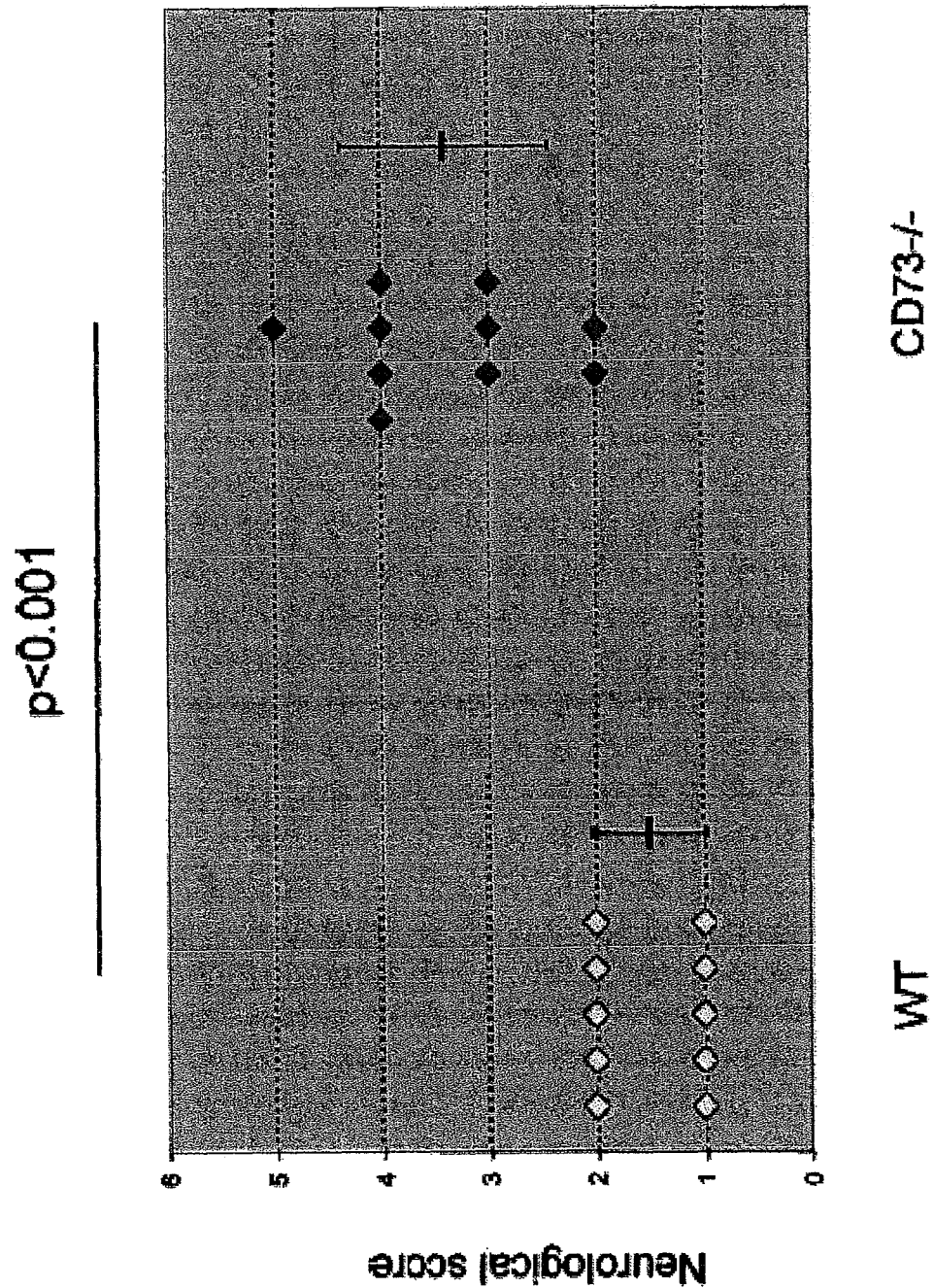
FIG. 15: Neurologic deficit scores shown for individual animals of the indicated genotype, after stroke, with mean±SEM indicated in column immediately to the right. All 6 animals from the (A) and (B) panels are included, as well as data from another 4 animals which did not undergo infarct volume analysis by MR [n=10 for each group]. *** denotes P<0.001.
Figure 16B:
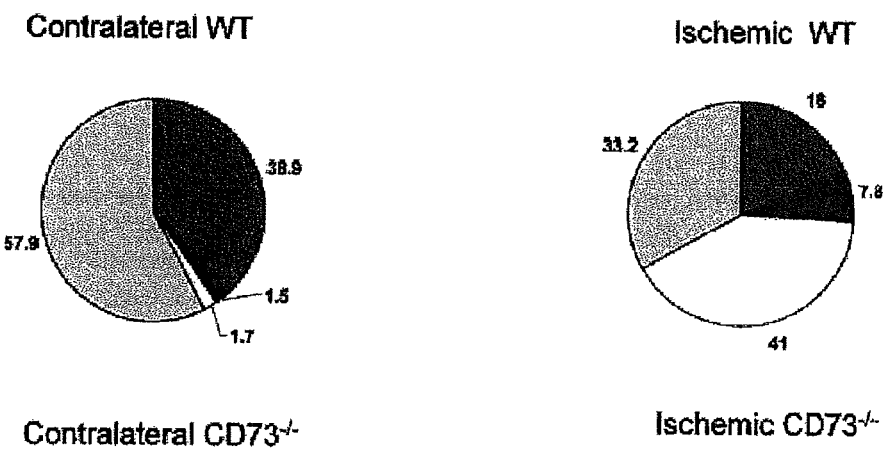

Effect of CD73 Gene Absence on Stroke Outcome:

Forty eight hours after induction of permanent MCA occlusion, cerebral infarct volumes were assessed in both CD73-deficient and wild-type mice using T2 weighted cortical MRIs. Total infarct volumes were increased by 49% in $CD73^{-/-}$ mice compared with their WT liftermates (68±2.6 mm$^3$, compared to 34.8±2.6 mm$^3$, respectively, p<0.001). The larger infarct volumes in $CD73^{-/-}$ mice corresponded well with the functional outcome after MCA occlusion, as the $CD73^{-/-}$ mice had greater neurological deficit as well in comparison with WT mice (FIG. 15). As an additional functional measure of outcome, especially when considering the known role for CD73 in maintaining epithelial and endothelial barrier properties (Thompson L F., at al., 2004), a comparative analysis of cerebral edema was performed between groups, measured forty eight hours after induction of brain ischemia. In comparison with WT controls, brain water content was significantly increased (by ≈30%) in the infarcted hemisphere of $CD73^{-/-}$ mice (4.53±0.12 mL/g dry wt tissue vs 6.62±0.83 ml/g dry wt tissue, WT vs $CD73^{-/-}$ mice, respectively (n=5; p<0.001). Experiments were next performed to assess whether CD73 modulates leukocyte trafficking into ischemic cerebral tissue. Analysis of brain tissue was conducted using multiparameter flow cytometry 48 hours after induction of brain ischemia to quantify leukocyte populations in ischemic hemispheres. Ischemic hemispheres of CD73-deficient animals had a more than 30% increase in the total numbers of infiltrating nucleated cells when compared to wild type ischemic hemispheres (FIG. 16a). Since the non-ischemic hemispheres showed no significant differences in terms of infiltrating cell numbers between the two genotypes, we concluded that CD73 does not affect basal levels of cerebral inflammation (data not shown). To identify mononuclear fraction more precisely, we plotted CD45-positive cells which expressed the F4/80 mononuclear cell surface marker, which enable us to identify blood-derived macrophage population cells as $CD45^{hi}F4/80^{hi}$ expressors. F4/80 surface marker was used since it is more specific for macrophages than CD11 b, in that CD11b is also found on some B cells (Mack C L., et al. 2003). The second cell population examined was $CD45^{low}F4/80^{low}$ cells, which expressed 10 to 15 times less CD45 antigen then macrophages and hence were considered to be resident microglial cells. In order to examine the activation/phagocytic state of mononuclear cells within inflamed brain, as a third step we added two additional antibodies against B7-1 (CD80) and B7-2 (CD86) antigens. Analysis of cells infiltrating the ischemic brain showed a shift toward the mononuclear cellular fraction in $CD73^{-/-}$ mice compared with wild-type controls (FIG. 16a,b,c). In the ischemic hemispheres of $CD73^{-/-}$ animals, 13.8±0.3% of cells are macrophages, versus 7.8±0.5% in wild-type mouse ischemic hemispheres (FIG. 16b,c), reflecting a relative enrichment of the infiltrating macrophage infiltration, as well as a great increase in their total numbers (5.0×10$^5$±0.4× 10$^5$ in wild-type mice in comparison with 11.04±0.25×10$^5$ in $CD73^{-/-}$ (FIG. 16a).

Knowing this, we further hypothesized that infiltrating macrophages exposed to the more inflammatory environment of the central nervous system in the ischemic CD73−/− mice could potentially become more activated in comparison with macrophages isolated from comparable ischemic hemispheres of wild-type controls. Our data have shown that forty-eight hours after induction of brain ischemia, microglia isolated from wild-type as well as $CD73^{-/-}$ ischemic hemispheres express low, but measurable levels of B7-1 or B7-2 markers (data not shown). Moreover, $CD45^{hi}F4/80^{hi}$ infiltrating macrophages isolated from ischemic hemispheres of $CD73^{-/-}$ mice express higher level of both B7-1 and B7-2 markers as shown by the increase in fluorescent intensity in comparison with macrophages isolated from wild type ischemic hemisphere (WT mice CD80 molecule MFI 39.2±1.1 vs CD80 molecule in CD73 null mice MFI 98.7±1.9 and CD86 molecule in WT animals MFI 47.9±1.7 vs CD73 null mice MFI 52.6±2.5) Although the relative ratio of microglia and neutrophils did not change between wild type and $CD73^{-/-}$ ischemic hemispheres, absolute cell number of both populations were increased approximately 2-fold in the ischemic brain of CD73-deficient mice versus control animals (microglia 11.7×10$^5$±1.5×10$^5$ versus 5.8× 10$^5$±0.4×10$^5$; neutrophils 37.4×10$^5$±1.2×10$^5$ versus 23.4× 10$^5$ 1.1×10$^5$).

To confirm the pro-inflammatory phenotype of ischemic brains of $CD73^{-/-}$ mice, 48 hrs after induction of brain ischemia, expression of pro-inflammatory cytokines and adhesion molecules was analyzed by reverse transcription (RT)-PCR in brains from wild-type or CD73−/− null mice.

Figure 17A:
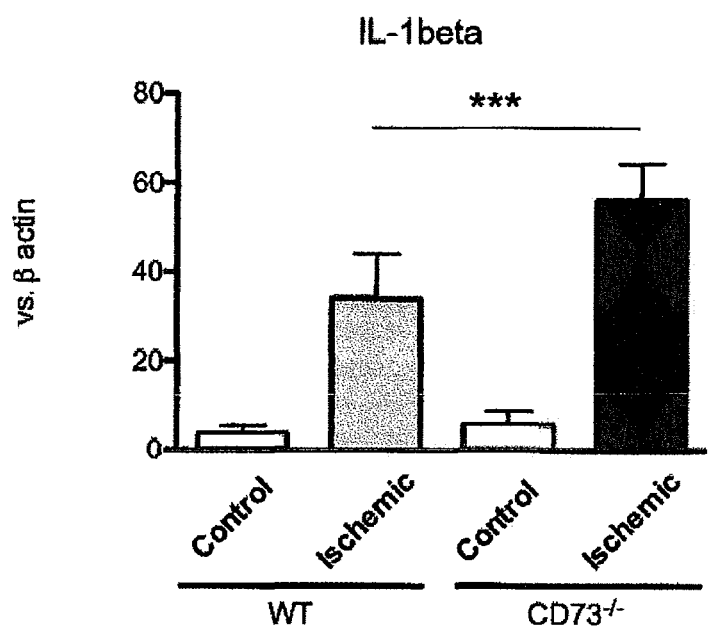
FIGS. 17A, 17B, 17C, 17D, 17E, and 17F: Role of CD73 on cytokine and adhesion molecule expression. mRNA levels were estimate using semiquantitative (RT)-PCR and normalized against β-actin mRNA. Expression of IL-1β mRNA (A); IL-6 mRNA (B); TNF-α mRNA (C); KC mRNA (D); VCAM-1 mRNA (E) and IL-10 mRNA (F) in contralateral and ischemic hemispheres of WT and CD73-/- mice are shown; (n=4 in each group; ***p<0.001).
Figure 17B:
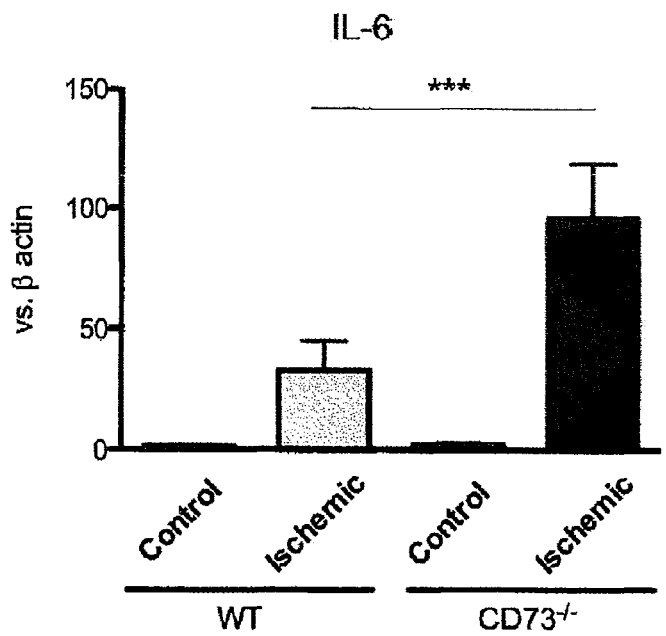
Figure 17C:
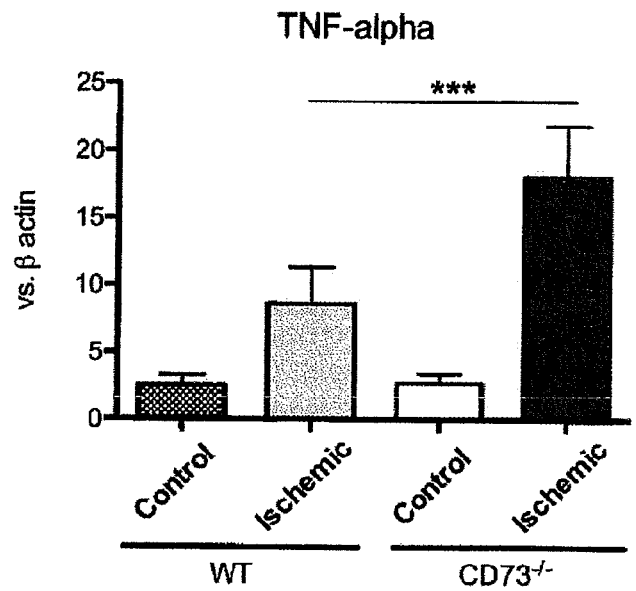
Figure 17D:
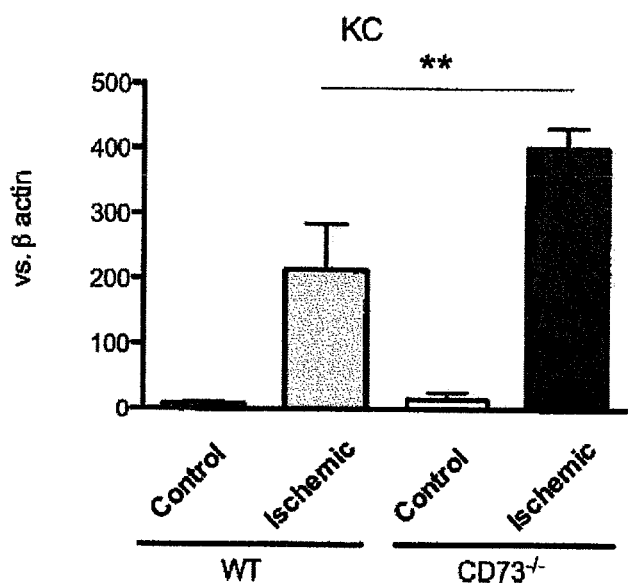
Figure 17E:
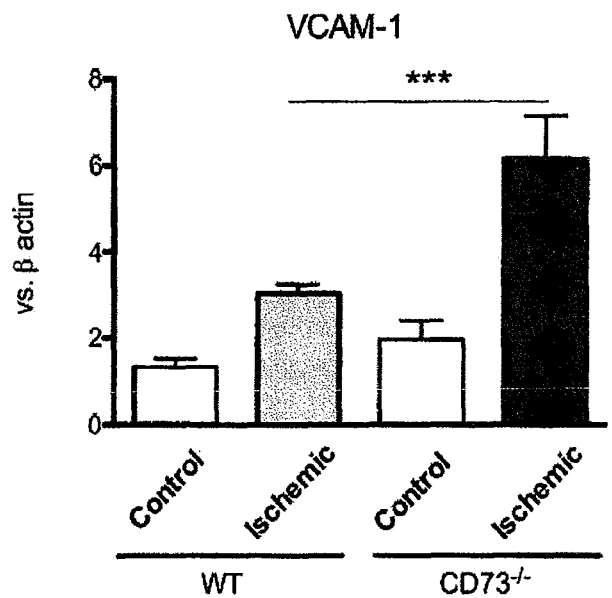
Figure 17F:
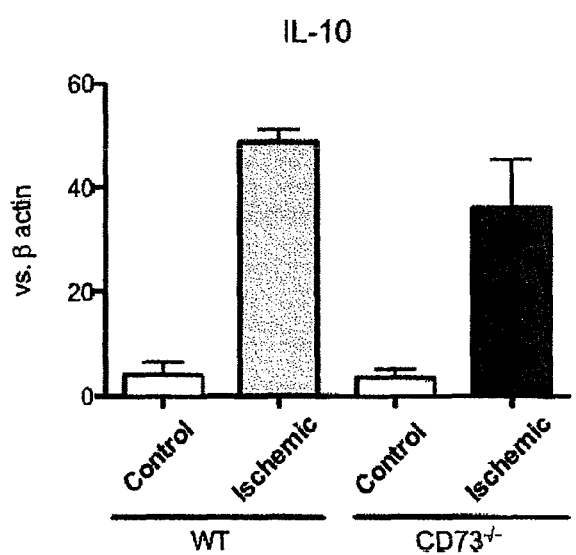

In addition to examining absolute levels of recruited effector leukocyte populations, experiments were performed to determine local production of inflammatory cytokines and adhesion molecules which could drive leukosequestration into the ischemic zone. As shown in a FIG. 17 (a,b,c,d), levels of mRNA mRNA in the ischemic hemispheres of $CD73^{-/-}$ animals for the cytokines IL-1β, IL-6, TNF-α, and KC was significantly increased compared with levels seen in WT mice. Although levels of VCAM-1 mRNA were slightly increased in the nonischemic hemispheres of CD73 mice, VCAM-1 mRNA levels were sharply up regulated in the ipsilateral (ischemic) hemispheres of $CD73^{-/-}$ mice following middle cerebral artery occlusion (FIG. 17e). These experiments went further to examine the induction of what is thought to be a countervailing anti-inflammatory cytokine, IL-10, which is known to suppress TNFalpha, IL-1, and IL-12 thereby contributing to both the limitation and resolution of inflammation. (8) Though not statistically significantly different, there was a trend towards diminished IL-10 mRNA in the ischemic brain of $CD73^{-/-}$ mice. In this manner, with upregulation of proinflammatory and down-regulation of anti-inflammatory cytokine portfolios, inflammation and leukocyte recruitment are promulgated in the ischemic territory (FIG. 17).

Figure 18A:
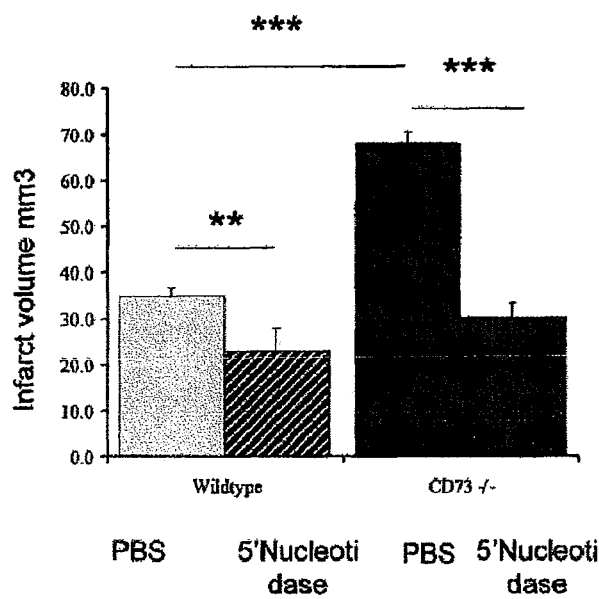
FIGS. 18A, 18B, 18C, 18D, 18E, and 18F: In order to assess the therapeutic potential of soluble 5' nucleotidase (CD73 analog) in preventing cerebral infarction, the experiments performed in a different cohort of mice. Forty-eight hrs following ischemia quantification of average cerebral infarct volume in ischemic WT and CD73 null mice treated with soluble 5' nucleotidase or vehicle was calculated (A) n=6 P<0.01; *P<0.001, along with functional outcome as determined by neurological deficit using a 5-tired grading system for each individual animal as shown in (B). The same mice were then subjected to flow cytometric analysis to determine the relative ratio (C) and absolute number of macrophages (D); n=6 *P<0.05; P<0.01; *P<0.001. Mean fluorescent intensity of macrophages expressing CD80 (E) and CD86 (F) molecules isolated from contralateral and ischemic hemispheres of WT and CD73 null mice treated with soluble 5'nucleotidase or vehicle; n=4; P<0.01; *P<0.001.
Figure 18B:
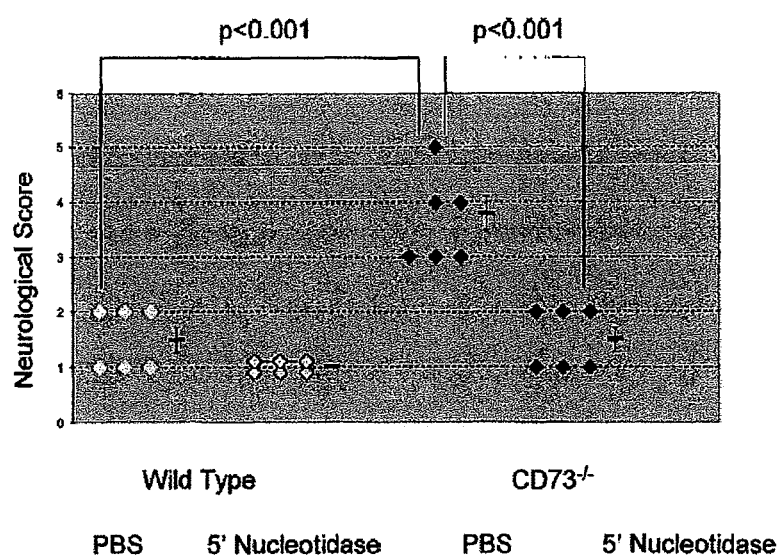

Rescue of CD73 Genotype Null Mice from Stroke Sequelae with Soluble 5'-Nucleotidase In order to fulfill Koch's postulates regarding a causal role for a pathway in disease, we not only performed experiments in which the pathway was deleted, but also experiments in which the deleted pathway was reconstituted. To prove the assertion that CD73 plays an important role in regulation of leukocyte trafficking in brain ischemia, CD73−/− and wild-type mice were each reconstituted with 7 U of soluble 5'-nucleotidase (5'-NT) purified from *Crotalus Atrox* venom, given 30 minutes before induction of brain ischemia. As in the earlier experiments, evaluation of infarct volumes (MRI's) along with neurological scores were both performed by blinded operators. The mice were then euthanized and ischemic and non-ischemic hemispheres were separated for flow cytometric analyses of infiltrating leukocyte populations. As shown in FIGS. 18a and 18b, 5'-nucleotidase treatment of CD73$^{-/-}$ mice was associated with the complete reconstitution of a wild type phenotype; cerebral infarct volumes were (69.7±5.8 mm$^3$ in saline-treated CD73$^{-/-}$ mice, versus 30.4±6.1 mm$^3$ CD73$^{-/-}$ treated with 5'-NT. For comparison, 5'NT was also able to reduce infarct volumes in WT animals; wild-type mice treated with saline demonstrated infarct volumes of 34.8±3.5 mm$^3$, whereas 5'-nucleotidase treatment of wild-type animals yielded a reduction in infarct size to 22.7±6.6 mm$^3$ (FIG. 18a). The reduction of infarct volumes in CD73$^{-/-}$ mice treated with 5'-NT corresponded well with improved functional outcomes after MCA occlusions quantified by neurological score (FIG. 18b).

Figure 16C:
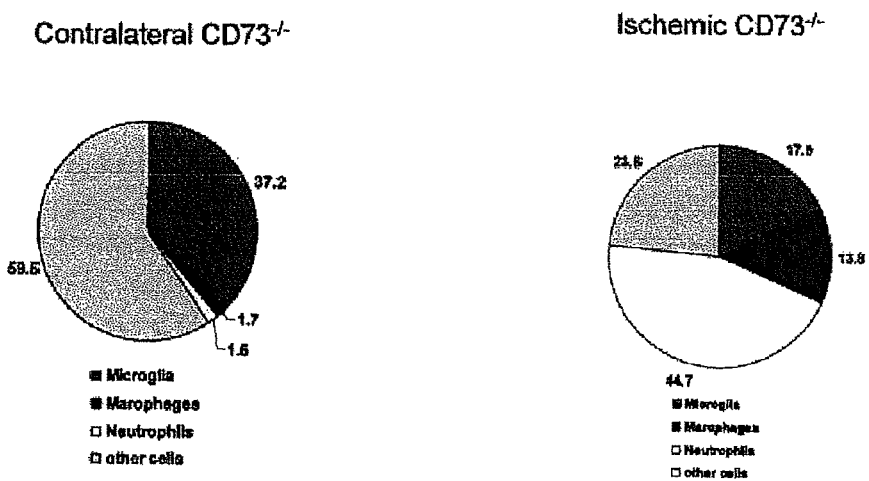
Figure 18C:
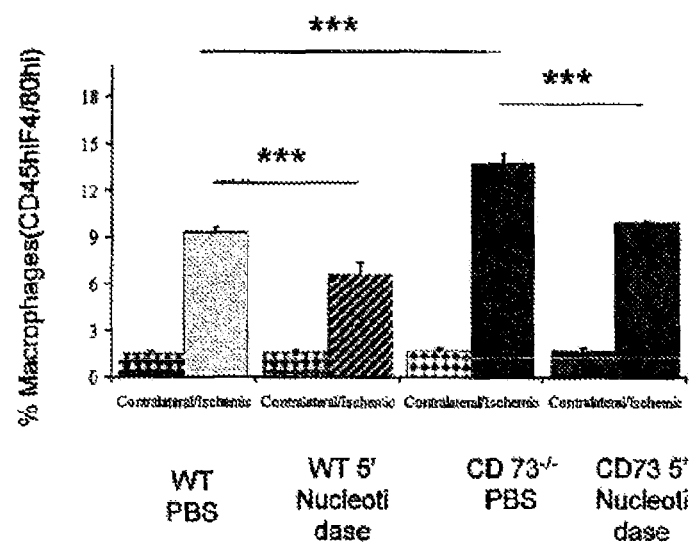

Leukocyte populations (neutrophils, microglia, mononuclear fraction) were identified using the same combinations of antibodies as before. We had previously observed (FIG. 16) that CD73-deficiency affects mostly the mononuclear fraction of infiltrating cells (CD45$^{hi}$F4/80$^{hi}$ macrophages) forty-eight hours after induction of brain ischemia. In this next set of experiments, 5'nucleotidase (5'NT) was administered immediately prior to the ischemic episode, 5'NT not only suppresses macrophage recruitment in ischemic wild-type mice (FIG. 18C), but it does so even more so in ischemic mice lacking native CD73; 5'NT reduces total numbers of infiltrating macrophages by 48% in WT animals and by 57% in. CD73$^{-/-}$ mice. As a percentage of total infiltrating leukocytes, 5'NT caused the macrophage population of ischemic CD73$^{-/-}$ mice to decrease to the same level as that seen in vehicle-treated wild-type controls (9.94%±0.5% CD73$^{-/-}$ treated with 5'-NT versus 9.33±0.3% in saline treated wild-type mice).

Figure 18D:
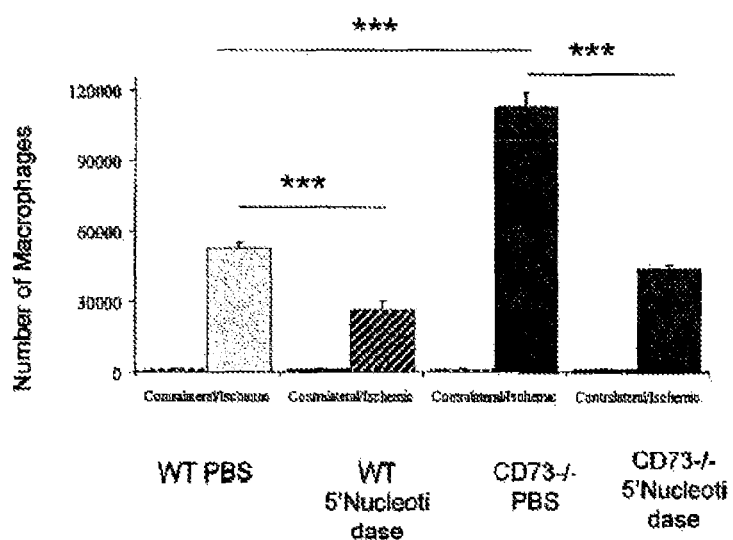
Figure 18E:
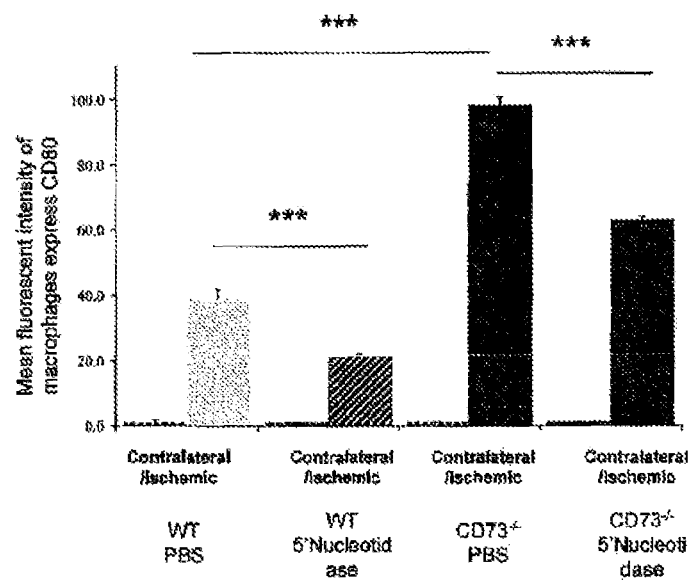
Figure 18F:
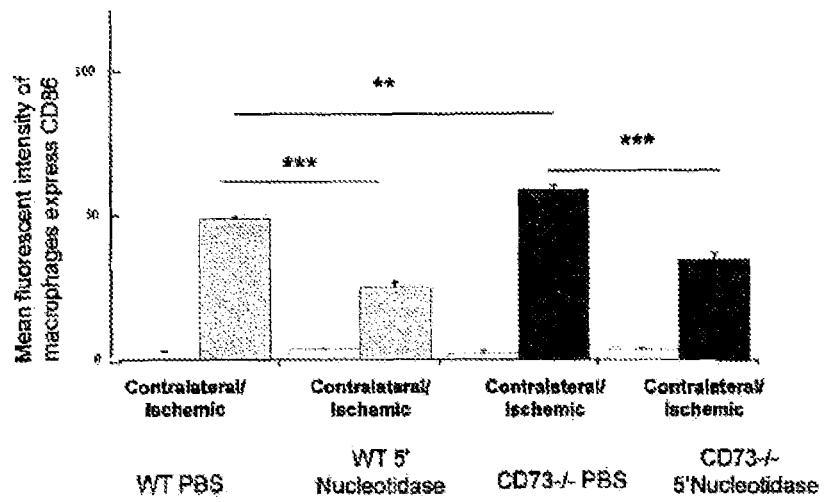

One other important facet of recruited leukocytes is related to their activation state, which can affect their effector functions. Treatment with soluble 5'-nucleotidase in both CD73$^{-/-}$ and wild-type mice not only resulted in a markedly reduced absolute number of infiltrating macrophages, but those infiltrating macrophages displayed a less activated phenotype at forty-eight hours after induction of brain ischemia (FIG. 18D,E). These data were obtained by measuring as expression of B7-1 (CD80) and B7-2 (CD86) antigens, costimulatory molecules nominally expressed at baseline but induced under activating conditions (especially for B7-1). For these data, B7-1 positive infiltrating macrophages (CD45hiF4/80hi CD80$^+$) isolated from ischemic hemispheres of CD73$^{-/-}$ mice treated with 5'-NT were shown to express significantly lower levels, of B7-1 antigen (34%) compared with macrophages isolated from ischemic hemispheres of saline-treated CD73$^{-/-}$ mice (FIG. 18 E,F). Note that CD73-deficient macrophages treated with saline demonstrated far greater activation then wild-type macrophages (FIG. 18 D,E,F). Treatment of wild-type mice with soluble 5'-NT resulted in an additional 44% reduction of B7-1 expression by macrophages isolated from their ischemic hemispheres in comparison with B7-1 expression by macrophages isolated from saline treated wild-type mice. By contrast, though the expression of B7-2 antigen on CD73-deficient macrophages did not increase as profoundly following ischemia as did B7-1 antigen, it did increase somewhat.

Absolute number of populations of both microglia and neutrophils were markedly reduced after treatment with soluble 5'-nucleotidase, whether this was administered to WT mice or CD73 knockout mice. When wild type mice were examined in the setting of stroke, addition of 5'NT caused a 28% reduction in microglial numbers (6.95×10$^5$±0.4×10$^5$ versus 9.4×10$^5$±0.33×10$^5$ for 5'NT-treated vs saline treated mice, P<0.05). When CD73−/− were similarly treated with 5'NT, there was an XX % reduction in microglia detected in the ischemic hemisphere (8.1×10$^5$±0.25×10$^5$ vs 14.3×10$^5$±0.7×10$^5$, P<0.001). Note that overall, lack of CD73 was associated with the largest numbers of microglia of any group, and that reconstitution of these mice with 5'NT restored these numbers to levels seen in WT mice. In other words, 5'NT "rescued" the phenotype of the CD73 gene null animals. In additional data which is not shown, the relative ratios of resident microglia and infiltrating neutrophils did not change among the groups, only the absolute numbers of cells changed (as shown).

Similar data were observed when neutrophil infiltration in the ischemic brain was examined. Treatment of wild-type animals with soluble 5'-nucleotidase resulted in 27% reduction of neutrophil infiltration when compared to wild-type saline-treated mice (17.1×10$^5$±1.1×10$^5$ neutrophils per ischemic hemisphere for 5'-NT treated wild-type mice, vs. 21.3×10$^5$±1.6×10$^5$ for wild-type saline-treated controls, P<0.01). An even greater absolute reduction in infiltrating neutrophils was observed in CD73$^{-/-}$ mice treated with 5'-NT (19×10$^5$±2.4×10$^5$ for 5'NT-treated CD73−/− mice, vs. versus 34×10$^5$±1.3×10$^5$ for CD73$^{-/-}$ saline-treated mice, P<0.001). Here again, 5'NT reconstituted the CD73 gene null mice to a WT-level of neutrophil-infiltration. These data using genetic and pharmacological approaches show for the first time that CD73 is a critical modulator of leukocyte infiltration after cerebral ischemia.

Stroke Sequelae in CD73 Chimeric Mice

In an attempt to discern the contribution of CD73 on resident vascular cells from that of CD73 on circulating leukocytes to the observed increase in leukocyte infiltration in CD73 deficient animals, a series of CD73 chimeric mice were generated and subjected to stroke. Four groups of chimeras were made by myeloablation and bone marrow reconstitution according to the following schema (Donor-→Recipient); WT marrow→WT recipient; CD73$^{-/-}$ marrow to WT recipient; WT marrow into CD73$^{-/-}$ recipient; and CD73$^{-/-}$ marrow into CD73$^{-/-}$ recipient. The first and last chimeras (KO→KO and WT→WT served as transplantation controls. KO→WT chimeras served as an experimental condition in which endothelium and other resident cells express CD73, however, circulating cells (leukocytes) do not. WT→KO chimeras served as an experimental condition in which CD73 is expressed on circulating leukocytes, however, it is absent from resident vascular cells. All experiments were performed eight to ten weeks after reconstitution to allow for full bone marrow reconstitution.

Figure 19A:
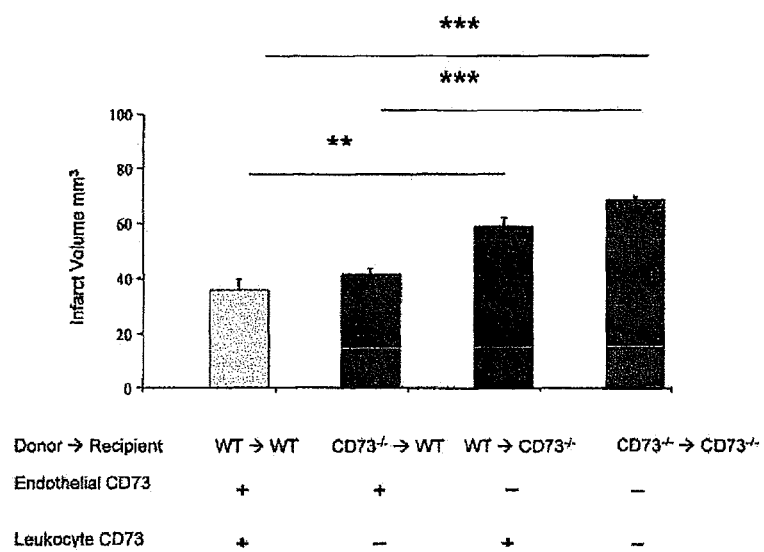
FIG. 19A-19B: Selective inactivation of CD73 molecule on tissue only attenuates brain ischemia. (A) Quantitative analyses of infarct volumes in marrow-reconstituted mice (n=4 per each group of mice; p<0.01; *p<0.001); (B) Locomotor activity determined by neurological deficit score was shown for individual animals across the genotype 48 hrs after induction of brain injury. (n=4 per each group of mice; p<0.01; *p<0.001).
Figure 19B:
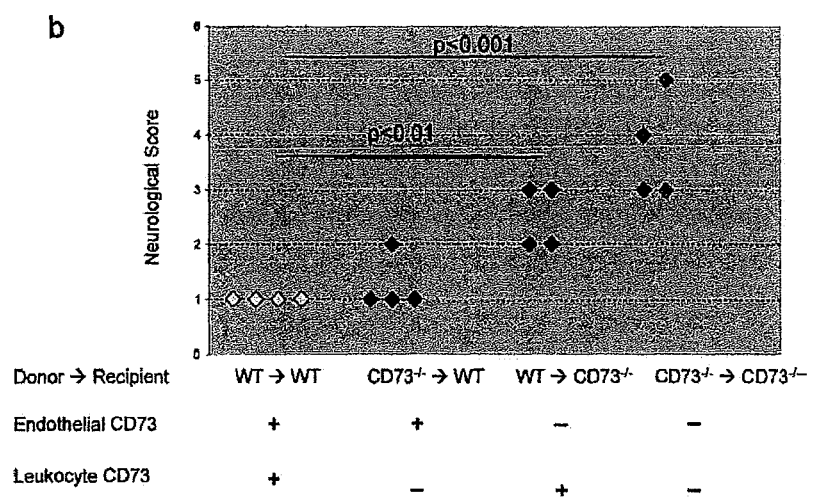

Forty eight hours after photothrombotic occlusion of the MCA, as in our earlier experiments, cerebral MRI scans were obtained to quantify infarction, neurological deficit scored by an operator blinded to experimental conditions, and leukocyte trafficking assessed by flow cytometry. Cerebral infarct volumes in the KO→KO group of mice was markedly larger (48%) then those in the WT→WT group (68.8±1.2 mm$^3$ vs 35.8±3.2 mm$^3$ respectively, P<0.001 (FIG. 19a). We next examined the effect of selective CD73 rescue by myeloablating naïve mice and reconstituting them with marrow cells possessing or lacking the CD73 gene, after which MCAO was performed. Infarct volumetric analysis demonstrated that expression of CD73 on vascular endothelium only (ie, KO marrow→WT recipient) provided some protection to mice from stroke when compared to mice with global deficiency of CD73 (the KO→KO group). Quantitatively, this protection was measurable as a 40% reduction in infarct volumes (41.6±1.7 mm$^3$ vs 68.8±1.2 mm$^3$ in KO→WT vs KO→KO groups respectively, P<0.001). These data show that there is a considerable contribution of tissue-resident CD73 in cerebroprotection after ischemic brain injury. We further examined the effect of selective expression of CD73 on bone-marrow derived cells, using a strategy of WT marrow implanted into CD73$^{-/-}$ recipients (WT→KO). This expression of CD73 on bone marrow cells only provided limited protection from cerebral ischemia (58.9±2.8 mm$^3$), which represent only 14% decrease in infarct volume in comparison with global lack of the CD73 molecule (KO→KO; P=NS), but nevertheless significantly larger infarct volumes (39%) in comparison with WT→WT controls (p<0.01). Consonant with these data, locomotor activity in the KO→WT group was substantially better than that in the KO→KO group, but there was no difference in basal locomotor activity between WT→WT and KO→WT mice (FIG. 19b).

These important anatomic and functional differences reflect a degree of protection by CD73, whether expressed globally or on selective cell populations. We next evaluated the effect of site-selective CD73 expression on the trafficking of leukocytes to the ischemic brain. Total numbers of nucleated cells infiltrating ischemic hemispheres paralleled infarct size as well as neurological deficit scores in each of the four groups of myeloablated and marrow-reconstituted mice under study (data not shown). By using a dual staining technique with anti-CD45 and anti-F4/80 antibodies, an infiltrating mononuclear fraction could be easily identified, and distinguished from the resident macroglial population. It is known that Levels of CD45 and F4/80 expression distinguish between macroglial (CD45$^{lo}$F4/80$^{lo}$) and CNS-associated macrophage populations (CD45$^{hi}$F4/80$^{hi}$). As in our previous experiments, the relative percentage of CD45$^{lo}$F4/80$^{lo}$ cells (microglia) among all leukocytes and also the relative percentage of CD45$^{hi}$LY6-G$^{hi}$ cells (neutrophils) did not change across genotypes. However, the total numbers of infiltrating cells of either population was significantly higher in KO→KO mice when compared to control (WT→WT) mice, or chimeric animals that have tissue-resident CD73 (KO→WT. Similarly, the presence of CD73 anywhere (on circulating or resident cells) reduced the accumulation of neutrophils in the ischemic brain.

After the induction of unilateral brain ischemia, the total number of infiltrating cells in the contralateral (nonischemic) hemisphere did not vary with respect to CD73 genotype or chimerism (data not shown). In myeloablated and reconstituted mice completely devoid of CD73, there was more than a 50% increase in the relative ratio of CD45$^{hi}$F4/80$^{hi}$ infiltrating macrophages compared to myeloablated and reconstituted control mice (WT→WT). In chimeric animals in which CD73 was present in brain resident tissue, (KO→WT) macrophage infiltration was similar to control chimeras (WT→WT). In contrast, WT→KO mice (where CD73 was present on leukocytes but not resident cells), macrophage infiltration was increased significantly (by 37%) in comparison with WT→WT strokes. Similarly, the total number of infiltrating macrophages was significantly increased (up to 2.5 fold) in KO→KO and WT→KO mice. When CD73 present solely on brain tissue but absent from leukocytes, there is little effect on leukocyte trafficking compared with WT→WT chimeras. These data together indicate that CD73 has an important native role which suppresses leukocyte accumulation in an ischemic zone especially when that CD73 is expressed on brain resident tissue.

In terms of potentially understanding a contribution of recruited leukocytes to ischemia and reperfusion injury, it is not only important to quantify numbers of accumulated leukocytes, as our previous experiments have done, but also to assess their activation state. In order to do so, this next set of experiments examined the expression of costimulatory molecules which are upregulated during immune activation following injury. Macrophages isolated from completely CD73-deficient chimeric mice (KO→KO) express ≈60% more CD80 and ≈26% more CD86 on their surface when compared with WT→WT controls. The presence of CD73 on brain resident tissue alone (KO→WT) greatly diminished the expression of both CD80 and CD86 molecules when compared with chimeras with global deficiency of CD73; (CD80 molecule MFI 50±12 in KO→WT mice compared to 113±17 MFI in KO→KO mice; CD86 molecule MFI 48±4 in KO→WT versus MFI 65±5 in KO→KO mice. On the other hand, macrophages isolated from ischemic hemispheres of mice deficient in tissue CD73 only (WT→KO) express significantly higher levels of CD80 when compared with macrophages isolated from control chimeric mice (WT→WT; MFI 85.7±7.6 versus 43±3.7. For CD86, there were no significant differences though trends in the same direction as for CD80.

Summary/Cerebral Ischemia

Catabolism of extracellular nucleotides by an enzyme, ENTDPase1 (CD39) protruding from the endothelial surface into the flowing blood stream has been implicated in limiting thrombosis in ischemic cerebral microvessels. The terminal product of the sequential phosphoydrolytic action of CD39 on ATP and ADP is AMP, which is cleaved by ecto-5' nucleotidase (CD73) to generate the purine nucleoside adenosine. The role of this second and terminal phosphoydrolysis step in the setting of an ischemic cerebrovascular bed is not known. Mice deficient for CD73 exhibited significantly larger (49%) cerebral infarct volumes as measured by magnetic resonance imaging when subjected to photo-thrombotic occlusion of the middle cerebral artery, compared with wild type mice bearing CD73 (34.8±1.9 mm$^2$, vs 68±2.6 mm$^3$, p<0.001). Mice lacking CD73 exhibited increased local accumulation of multiple leukocyte subsets (neutrophils, macrophages, and microglia) by flow cytometric analysis of tissue homogenates, with the most marked increase (as both percentage and in total) being seen in CD45$^{hi}$F4/80$^{hi}$. +ve cells of the macrophage lineage. In addition, these cells exhibited increased levels of activation costimulatory markers (CD86, CD80) compared with WT mice. CD80 molecule expressed by macrophages isolated from CD73 null mice MFI 98.7±1.9 vs CD80 expressed by macrophages isolated from ischemic hemispheres of WT animals MFI 39.2±1.1, p<0.001; and CD86 molecule in CD73 null mice MFI 52.6±2.5 vs CD86 molecule in WT mice MFI 47.9±1.7, p<0.05). The wild-type, neuroprotected phenotype was restored to the CD73 gene null mice by provision of soluble 5' nucleotidase. As CD73 is borne on both circulating leukocytes as well as cerebrovascular endothelium, marrow obliteration by radiation was followed by adoptive transfer of WT or CD73 marrow, and strokes were created following engraftment. Engrafted mice lacking endothelial CD73 exhibited larger cerebral infarcts than engrafted mice whose leukocytes lacked CD73, suggesting that ischemic cerebral protection is conferred by the CD73 expressed on vascular endothelium. Flow cytometric analyses demonstrated a significant increase in the infiltrating $CD45^{hi}F4/80^{hi}$ macrophage populations in ischemic hemispheres of mice with CD73 tissue-deficiency only, compared to mice with endothelial CD73 only (28% increase) or CD73 in all tissues (37% increase). These same macrophage populations, when observed in chimeras without CD73 demonstrated evidence of greater activation when compare to control chimeras (60% greater CD80 mean fluorescence intensity (MFI) and 26% greater CD86 MFI (Table 1). Presence of CD73 in the tissue alone greatly diminished the expression of both CD80 and CD86 when compare with completely CD73 deficient chimeras. Taken together, these experiments provide, for the first time, evidence of a role for tissue-derived CD73 in cerebroprotection, and its potential role in modulation of inflammation and brain immune system function.

Example 4

Effect of Ectonucleotidases on Atherosclerosis

Mice which were bred on a hyperlipidemic (apolipoprotein E deficient) background exhibited increased atherosclerosis early during the course of lesion development when ectonucleotidases were deficient. For instance, mice null for the CD73 gene have increased atherosclerosis early during the course of lesion development. This indicates that CD73 protects against atherosclerosis at early stages. Similar arguments can be made for other ectonucleotidases. These lead us to propose that increasing ectonucleotidase levels, by administering agents which increase endogenous levels of ectonucleotidases (including cyclic AMP or other second messenger stimulating analogues), a protein, cells which overexpress nucleotidases, or vectors which cause cells to overexpress nucelotidases, can protect against atherosclerosis and protect against ischemic disorders.

Example 5

Increasing Endogenous Nucleotidase Levels by Second Messenger Pathway Stimulation It was found that treating cells in culture with cAMP analogues causes a marked upregulation of endogenous ectonucleotidase CD39. This suggests that this strategy, as well as other related strategies such as use of NO donors, cGMP analogues, or phosphodiesterase inhibitors, can also increase endogenous nucleotidase levels and hence confer vascular protection.

Example 6

Illustrative CD73 Polypeptides and Nucleic Acids

Soluble CD73 is readily obtainable from commercial sources; for example, from Sigma Aldrich (catalogue number N8661; source *Crotalus* Atrox).

Illustrative CD73 polypeptides suitable for use in the methods of the invention include those set forth in SEQ ID NO:'s 1, and 3 (encoded by the nucleotide sequences set forth in SEQ ID NO's: 2 and 4 respectively) set forth below and in the Sequence Listing submitted herewith.

```
Homo sapiens 5'-nucleotidase, ecto (CD73) (NT5E)
Polypeptide.
                                                            SEQ ID NO: 1
MCPRAARAPATLLLALGAVLWPAAGAWELTILHTNDVHSRLEQT

SEDSSKCVNASRCMGGVARLFTKVQQIRRAEPNVLLLDAGDQYQGTIWFTVYKGAEVA

HFMNALRYDAMALGNHEEDNGVEGLIEPLLKEAKFPILSANIKAKGPLASQISGLYLP

YKVLPVGDEVVGIVGYISKETPFLSNPGINLVFEDEITALQPEVDKLKTLNVNKIIAL

GHSGFEMDKLIAQKVRGVDVVVGGHSNIFLYTGNPPSKEVPAGKYPFIVTSDDGRKVP

VVQAYAFGKYLGYLKIEFDERGNVISSHGNPILLNSSIPEDPSIKADINKWRIKLDNY

STQELGKTIVYLDGSSQSCRFRECNMGNLICDAMINNNLRHTDEMFWNHVSMCILNGG

GIRSPIDERNNGTITWENLAAVLPFGGTFDLVQLKGSTLKKAFEHSVHRYGQSTGEFL

QVGGIHVVYDLSRKPGDRVVKLDVLCIKCRVPSYDPLKMDEVYKVILPNFLANGGDGF

QMIKDELLRHDSGDQDINVVSTYISKMKVIYPAVEGRIKESTGSHCHGSFSLIFLSLW

AVIFVLYQ //

SEQ ID NO: 2; Homo sapiens; Nucleotide encoding CD73 polypeptide
shown in SEQ ID NO: 1
Exons 896-4057;
    1    actcctcctc tctgccdctc agctcgctca tctttcttcc cgccccctct cttttccttc 61    tttggttctt tgaagtgatg agctagcgca accacaaacc atacattcct tttgtagaaa 121    aacccgtqcc tcgaatgagg cgagactcag agaggaccca ggcgcggggc ggacccctcc 181    aattccttcc tcgcgccccc gaaagagcgg cgcaccagca gccgaactgc cggcgcccag
```

-continued

```
 241  gctccctggt ccggccggga tgcggccggt acccgctccc cgccgggaac aacctctcca
 301  ctcttcctgc agggagctgg tgccagccga cagccgcgcc agggccgctc cgggtaccag
 361  ggtcggatcg ggtgacgtcg cgaacttgcg cctggccgcc aagccggcct ccaggctgaa
 421  gaaggacccg ccccggcctt gacccgggcc ccgcccctcc agcggggca ccgagccccg
 481  gccctagctg ctcgcccta ctcgccggca ctcgcccggc tcgcccgctt tcgcacccag
 541  ttcacgcgcc acagctatgt gtccccgagc cgcgcgggcg cccgcgacgc tactcctcgc
 601  cctgggcgcg gtgctgtggc ctgcggctgg cgcctgggag cttacgattt tgcacaccaa
 661  cgacgtgcac agccggctgg agcagaccag cgaggactcc agcaagtgcg tcaacgccag
 721  ccgctgcatg ggtggcgtgg ctcggctctt caccaaggtt cagcagatcc gccgcgccga
 781  acccaacgtg ctgctgctgg acgccggcga ccagtaccag ggcactatct ggttcaccgt
 841  gtacaagggc gccgaggtgg cgcacttcat gaacgccctg cgctacgatg ccatggcact
 901  gggaaatcat gaatttgata tggtgtgga aggactgatc gagccactcc tcaaagaggd
 961  caaatttcca attctgagtg caaacattaa agcaaggggg ccactagcat ctcaaatatc
1021  aggactttat ttgccatata aagttcttcc tgttggtgat gaagttgtgg gaatcgttgg
1081  atacacttcc aaagaaaccc cttttctctc aaatccaggg acaaatttag tgtttgaaga
1141  tgaaatcact gcattacaac ctgaagtaga taagttaaaa actctaaatg tgaacaaaat
1201  tattgcactg ggacattcgg gttttgaaat ggataaactc atcgctcaga aagtgagggg
1261  tgtggacgtc gtggtgggag gacactccaa cacatttctt tacacaggca atccaccttc
1321  caaagaggtg cctgctggga agtacccatt catagtcact tctgatgatg ggcggaaggt
1381  tcctgtagtc caggcctatg cttttggcaa atacctaggc tatctgaaga tcgagtttga
1441  tgaaagagga aacgtcatct cttcccatgg aaatcccatt cttctaaaca gcagcattcc
1501  tgaagatcca agcataaaag cagacattaa caaatggagg ataaaattgg ataattattc
1561  tacccaggaa ttagggaaaa caattgtcta tctggatggc tcctctcaat catgccgctt
1621  tagagaatgc aacatgggca acctgatttg tgatgcaatg attaacaaca acctgagaca
1681  cacggatgaa atgttctgga ccacgtatc catgtgcatt ttaaatggag gtggtatccg
1741  gtcgcccatt gatgaacgca caatggcac aattacctgg gagaacctgg ctgctgtatt
1801  gcccttggga ggcacatttg acctagtcca gttaaaaggt tccaccctga agaaggcctt
1861  tgagcatagc gtgcaccgct acggccagtc cactggagag ttcctgcagg tgggcggaat
1921  ccatgtggtg tatgatcttt cccgaaaacc tggagacaga gtagtcaaat tagatgttct
1981  ttgcaccaag tgtcgagtgc ccagttatga ccctctcaaa atggacgagg tatataaggt
2041  gatcctccca aacttcctgg ccaatggtgg agatgggttc cagatgataa aagatgaatt
2101  attaagacat gactctggtg accaagatat caacgtggtt tctacatata tctccaaaat
2161  gaaagtaatt tatccagcag ttgaaggtcg gatcaagttt ccacaggaa gtcactgcca
2221  tggaagcttt tctttaatat ttctttcact ttgggcagtg atctttgttt tataccaata
2281  gccaaaaatt ctccttgcct ttaatgtgtg aaactgcatt ttttcaagtg agattcaaat
2341  ctgccttta ggacctggct ttgtgacagc aaaaaccatc tttacaggct cctagaagct
2401  gaaggttaga gcattataaa atgaagagac agacatgatt actcagggtc agcaacctag
2461  tgagttagaa aaaaaattaa catagggccc tataaggaga aagccaacta tgttaagttt
2521  acgtgtccaa attttaatga aattttacta acaatttaa accatatttt tcttcttcat
2581  atccatttct aatccatcaa acagcttatg tttacataaa attttatcat tcacaaggaa
```

```
2641  gttttaagca cactgtctca tttgatatcc acaacttatt tttggtagga aagagagatg
2701  tttttcccac ctgtcagatg aaaaaactga agctcaaaaa gggttgactt gaccatacag
2761  ctaatgctga cagatccaag acctagacct aggtcttttg aactcaagtc cagcattctc
2821  aactatatca agttactgtt cagaatactt aatatctcct ctcttcataa ttatcaatag
2881  ccccaagctc atggatgaca aatctctgct ttatttcttg tctctatttt ttcactttat
2941  agctcctgtt ataatagcaa gtttaatggt ataaacacag gataccatcc tctcttgcaa
3001  cacccatgtg cctttgatga gtcaggtagc aagctgtagt agataatgag aaaggccaga
3061  ggctgcaaaa gacagtcaaa ggacacgaga gaaaggaagg ggaagaacag gactccagga
3121  ctgttttata ttatagaaaa gcaagagcta aagagcattt acacatgtta aacagatact
3181  tgttaagcat agtgcctgac acacggcatt agctgttatt ttatgagatt ccatcagctc
3241  tgcctctgtc ctctttcttc taacatgaag gtatcatgag aagagaacct tctaacataa
3301  gctgtaattc taaacctgca cttgtccctc tccagcaaga ggctagcact gaattcattc
3361  tactcatact acacacccag ttatggaatg tccagagttc tcgaagaaaa taaatgactt
3421  taggaagagg tatacatttt ttaagtcgct ctgcctccaa atctgaacag tcactgtaaa
3481  tcattcttaa gcccagatat gagaacttct gctggaaagt gggaccctct gagtgggtgg
3601  agtggaacca catgagcctg ctcagctctg cataagtaat tcaagaaatg ggaggattca
3661  ccttaaaaac agtgtgcaaa tggcagctag aggttttgat aggaagtatg tttgtttctt
3721  agtgtttaca aatattaagt actcttgata caaaatatac ttttaaactt cataaccttt
3781  ttataaaagt tgttgcagca aataatagc ctcggttcta tgcatatatg gattagctat
3841  aaaaaatgtc aataagattg tacaaggaaa attagagaaa gtcacattta gggtttattt
3901  tttacacttg gccagtaaaa tagggtaaat cctattagaa tttttttaaag aactttttttt
3961  aagtttccta aatctgtgtg tgtattgtga agtggtataa gaaatgadtt tgaaccactt
4021  tgcaattgta gattcccaac aataaaattg aagataaaaa aaaaaaaaaa aaaaaaaaaa
4081  aaaaaaa
```

*Danio rerio* 5'-nucleotidase, ecto (CD73) (NT5E) Polypeptide.
/organism = "*Danio rerio*"
SEQ ID NO: 3

MMMMNVLSALLIWIHCQLCWSADEQLTLLHTNDVHARVEETNK

DSGKCSKPPCFAGVSRRSTKIKEIRSKEKNVLLLDAGDQFQGTVWFNYYKGAEAAYFM

NQLKYDAMALGNHEFDNGVDGLLKPFLQEVNCTVLSANIKADETLAPRISGYYFPYKI

FTLGSEKVGVVGYTSAETPALSLPGPHLKFEDEITALQPQVDKLLTLGVNKIIALGHS

GFLMDQMIAKKVQGVDVVIGGHTNTFLYTGDPPSTEVPAGPYPLMVKSDDGRQVPVVQ

AYAFGKYLGFLKVTFDANGNVLESTGNPILLNSSVEPDPDIQAKVDSWRMNLANYSSQ

QVGQTLVFLNGTFEECRFRECNLGNLICDAMVHHNIKYADELQWNHVSSCILNGGGIR

GPIDERNRNGSITMEDLIAVLPFOGTEDLVQLNGSTLLEAFEHSVRRHOGNTGEFLQV

SGFQVVYDLSKAPGSRVKSVKVLCTQCRVPHYEPLVPNKVYKVVLPSYLVDGGDGFTM

IKEKKLKHDSGDLDISVVAGYISERKRVHRAVEGREQFSSSCAGLRGYISTVLLLWAV

WLMLV //

SEQ ID NO: 4; *Danio rerio*; Nucleotide encoding CD73 polypeptide shown
in SEQ ID NO: 3

```
  1  attttacagt aggaggatga tgatgatgat gaatgtcctc tccgcgttgc tgctgctctt
 61  cattcactgt cagctgtgct ggtctgcgga cttccagctc acttttgctgc acaccaatga
121  cgtgcacgcg cgagtggagg agaccaacaa ggactcgggc aaatgcagca gccgccgtgt
```

-continued

```
 181   tttcgccgga gtgtcgcgga gatccaccaa aatcaaagaa atccgcagca aggagaaaaa
 241   cgtgctgctg ctggacgcag gagaccagtt ccagggcacc gtctggttta actattacaa
 301   gggcgctgag gcggcgtatt tcatgaacca gctcaaatac gacgcgatgg ctttaggaaa
 361   ccatgagttt gacaacggcg tggacggcct gctgaaacct ttccttcagg aggtgaactg
 421   cactgttctc agcgccaaca tcaaagctga tgagacactt gctcctcgga tcagcggata
 481   ctatttccca tataaaatct tcacgttggg ctcagagaaa gtgggtgttg tcggctacac
 541   atcggcggag acgcctgctt tgtctctacc aggcccacat ctgaagtttg aggatgaaat
 601   cacggctcta cagcctcaag tggataaact cttgactttg ggtgttaata agatcatcgc
 661   tctgggacat tctggcttcc taatggatca aatgatcgcg aagaaggttc agggagtgga
 721   cgttgtgatt ggaggacaca ccaatacatt cttgtacacg ggagatccac cgtccacaga
 781   agttcccgca gggccgtatc cactcatggt caagtcagac gacggccggc aggtgcctgt
 841   ggtccaggct tatgcctttg gaaaatatct gggattcctg aaagtgactt ttgatgcaaa
 901   cggaaatgtg ctggagtcga caggaaaccc cattcttctg aatagttcag tagaacccga
 961   tcccgacatc caggctaaag tggacagctg gaggatgaat ctggccaact actcctctca
1021   gcaagtggga cagactctag tcttcctcaa cggcaccttc gaggagtgtc gctttcgtga
1081   atgcaatttg gggaatttaa tctgtgatgc catggtccat cataatatta aatacgccga
1141   cgagctccag tggaaccatg tcagctcttg tattctaaac ggtggaggca ttcgaggacc
1201   tattgatgag cgaaacagaa acggttccat cacaatggag gacctgatcg ccgtgctgcc
1261   gtttggagga acattcgacc tggtccagct gaacggatcg actctattag aagcttttga
1321   gcactcagtt cgccgacacg gaggaaacac tggagaattc ctacaggtgt caggttttca
1381   ggtggtgtat gatttatcga aagcgcctgg tagccgtgtt aaaagtgtga aagtgctctg
1441   cacccagtgt Cgagtgcctc Attatgaacc gctggtcccc aacaaggtgt ataaagtagt
1501   gctgccgtct tacctagtgg acgaggaga cggattcacc atgatcaaag agaagaaact
1561   caaacacgac agcggtgatc tggatatatc ggttgttgct ggctacatct ccgagaggaa
1621   gagagttcat ccggctgtgg agggacgctt ccagttcagc agctcctgtg ctggtcttcg
1681   gggatacacg tccaccgttc tgctgctgtg ggccgtctgg ctcatgcttg tttagccagt
1741   aaacatcatt ctaatgcact ttgtacaaca tctagccctt ttatgtgtga ctgtacagtc
1801   agatgaggaa aaagaaacc tctagcccaa agatgagttg tcttcatagg agtcgactga
1861   taattaacac tgtgatgtag aacagatgac ctaaaatccc tcttcttgta aaacaagatc
1921   ttatcataag agaaacacag ggacagtgtc attataccct tgtatacatg taacactcca
1981   tctttgtgcg gggagctatt tCatgaggaa taatccagga atctgagtta taaaacatta
2041   gaaacattcc tacaagtgag cgtctgcctc aataaatgtg tatttatttt gttaatgata
2101   aaaaaaaaaa aaaaaa
```

---

The invention claimed is:

1. A method of treating cerebrovascular ischemia in a subject, the method comprising administering to a subject with cerebrovascular ischemia a composition comprising an effective amount of one or more agents which dissipate nucleotide monophosphate; wherein in said composition one agent which dissipates nucleotide is a soluble ecto-5'-nucleotidase (CD73) of SEQ ID NO: 1 or SEQ ID NO: 3.

2. A method of treating cerebrovascular ischemia in a subject by inhibiting leukocyte infiltration into a site of the cerebrovascular ischemia in the subject, which comprises administering to the subject a composition comprising an effective amount of soluble ecto-5'-nucleotidase (CD73) of SEQ ID NO: 1 or SEQ ID NO: 3.

3. The method according to claim 2 wherein said leukocyte is a macrophage.

4. The method according to claim 1, wherein the composition further comprises at least one A2a adenosine receptor agonist.

5. The method according to claim 1, wherein the composition further comprises at least one A2B adenosine receptor agonist.

6. The method according to claim 1, wherein the composition further comprises and at least one A2A receptor agonist; and wherein said composition is a pharmaceutical composition further comprising a pharmaceutically acceptable carrier.

7. The method according to claim 1, wherein the composition further comprises at least one agent selected from an A2BAR receptor agonist;

and wherein said composition is a pharmaceutical composition further comprising a pharmaceutically acceptable carrier.

* * * * *

UNITED STATES PATENT AND TRADEMARK OFFICE
CERTIFICATE OF CORRECTION

Page 1 of 1

PATENT NO. : 10,874,719 B2
APPLICATION NO. : 14/594687
DATED : December 29, 2020
INVENTOR(S) : David J. Pinsky et al.

It is certified that error appears in the above-identified patent and that said Letters Patent is hereby corrected as shown below:

On the Title Page

At item (57), Line 10, "amount a" should be -- amount of a --.

At item (57), Line 12, "a fragment" should be -- a fragment, --.

In the Claims

At Column 60, Line 48, In Claim 4, "A2a" should be -- A2A --.

At Column 60, Line 54, In Claim 6, "and at" should be -- at --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 4

<210> SEQ ID NO 1
<211> LENGTH: 574
<212> TYPE: PRT
<213> ORGANISM: Homo Sapiens

<400> SEQUENCE: 1

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
    195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
    275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
```

```
                420             425             430
Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
            450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
            530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570

<210> SEQ ID NO 2
<211> LENGTH: 4027
<212> TYPE: DNA
<213> ORGANISM: Homo Sapiens

<400> SEQUENCE: 2
actcctcctc tctgcccctc agctcgctca tctttcttcc cgccccctct cttttccttc      60
tttggttctt tgaagtgatg agctagcgca accacaaacc atacattcct tttgtagaaa     120
aacccgtgcc tcgaatgagg cgagactcag agaggaccca ggcgcggggc ggacccctcc     180
aattccttcc tcgcgccccc gaaagagcgg cgcaccagca gccgaactgc ggcgcccag      240 gctccctggt ccggccggga tgcggccggt acccgctccc cgccgggaac aacctctcca     300
ctcttcctgc agggagctgg tgccagccga cagccgcgcc agggccgctc cgggtaccag     360
ggtcggatcg ggtgacgtcg cgaacttgcg cctggccgcc aagccggcct ccaggctgaa     420
gaaggacccg ccccggcctt gacccggggcc ccgcccctcc agcggggca ccgagccccg     480 gccctagctg ctcgccccta ctcgccggca ctcgcccggc tcgcccgctt cgcacccag     540 ttcacgcgcc acagctatgt gtccccgagc cgcgcgggcg cccgcgacgc tactcctcgc     600
cctgggcgcg gtgctgtggc ctgcggctgg cgcctgggag cttacgattt tgcacaccaa     660
cgacgtgcac agccggctgg agcagaccag cgaggactcc agcaagtgcg tcaacgccag     720
ccgctgcatg gtggcgtgg ctcggctctt caccaaggtt cagcagatcc gccgcgccga     780
acccaacgtg ctgctgctgg acgccggcga ccagtaccag ggcactatct ggttcaccgt     840
gtacaagggc gccgaggtgg cgcacttcat gaacgccctg cgctacgatg ccatggcact     900
gggaaatcat gaatttgata atggtgtgga aggactgatc gagccactcc tcaaagaggc     960
caaatttcca attctgagtg caaacattaa agcaaagggg ccactagcat ctcaaatatc    1020 aggacttat ttgccatata aagttcttcc tgttggtgat gaagttgtgg gaatcgttgg    1080
atacacttcc aaagaaaccc ctttctctc aaatccaggg acaaatttag tgtttgaaga    1140
tgaaatcact gcattacaac ctgaagtaga taagttaaaa actctaaatg tgaacaaaat    1200
tattgcactg ggacattcgg gttttgaaat ggataaactc atcgctcaga aagtgagggg    1260
```

```
tgtggacgtc gtggtgggag gacactccaa cacatttctt tacacaggca atccaccttc    1320
caaagaggtg cctgctggga agtacccatt catagtcact tctgatgatg ggcggaaggt    1380
tcctgtagtc caggcctatg cttttggcaa atacctaggc tatctgaaga tcgagtttga    1440
tgaaagagga aacgtcatct cttcccatgg aaatcccatt cttctaaaca gcagcattcc    1500
tgaagatcca agcataaaag cagacattaa caaatggagg ataaaattgg ataattattc    1560
tacccaggaa ttagggaaaa caattgtcta tctggatggc tcctctcaat catgccgctt    1620
tagagaatgc aacatgggca acctgatttg tgatgcaatg attaacaaca acctgagaca    1680
cacggatgaa atgttctgga accacgtatc catgtgcatt ttaaatggag gtggtatccg    1740
gtcgcccatt gatgaacgca acaatggcac aattacctgg gagaacctgg ctgctgtatt    1800
gccctttgga ggcacatttg acctagtcca gttaaaaggt tccaccctga agaaggcctt    1860
tgagcatagc gtgcaccgct acggccagtc cactggagag ttcctgcagg tgggcggaat    1920
ccatgtggtg tatgatcttt cccgaaaacc tggagacaga gtagtcaaat tagatgttct    1980
ttgcaccaag tgtcgagtgc ccagttatga ccctctcaaa atggacgagg tatataaggt    2040
gatcctccca aacttcctgg ccaatggtgg agatgggttc cagatgataa aagatgaatt    2100
attaagacat gactctggtg accaagatat caacgtggtg tctacatata tctccaaaat    2160
gaaagtaatt tatccagcag ttgaaggtcg gatcaagttt tccacaggaa gtcactgcca    2220
tggaagcttt tctttaatat ttcttcactt tgggcagtg atctttgttt tataccaata    2280
gccaaaaatt ctccttgcct ttaatgtgtg aaactgcatt ttttcaagtg agattcaaat    2340 ctgccttta ggacctggct tgtgacagc aaaaaccatc tttacaggct cctagaagct    2400
gaaggttaga gcattataaa atgaagagac agacatgatt actcagggtc agcaacctag    2460
tgagttagaa aaaaaattaa catagggccc tataaggaga agccaacta tgttaagttt    2520 acgtgtccaa attttaatga aattttacta acaattttaa accatatttt tcttcttcat    2580
atccatttct aatccatcaa acagcttatg tttacataaa attttatcat tcacaaggaa    2640
gttttaagca cactgtctca tttgatatcc acaacttatt tttggtagga agagagatg    2700 ttttttcccac ctgtcagatg aaaaaactga agctcaaaaa gggttgactt gaccatacag    2760
ctaatgctga cagatccaag acctagacct aggtcttttg aactcaagtc cagcattctc    2820
aactatatca agttactgtt cagaatactt aatatctcct ctcttcataa ttatcaatag    2880
ccccaagctc atggatgaca aatctctgct ttatttcttg tctctatttt ttcactttat    2940
agctcctgtt ataatagcaa gtttaatggt ataaacacag ataccatcc tctcttgcaa    3000 cacccatgtg cctttgatga gtcaggtagc aagctgtagt agataatgag aaaggccaga    3060
ggctgcaaaa gacagtcaaa ggacacgaga gaaggaagg ggaagaacag gactccagga    3120
ctgttttata ttatagaaaa gcaagagcta aagagcattt acacatgtta aacagatact    3180
tgttaagcat agtgcctgac acacggcatt agctgttatt ttatgagatt ccatcagctc    3240
tgcctctgtc ctctttcttc taacatgaag gtatcatgag aagagaacct tctaacataa    3300
gctgtaattc taaacctgca cttgtccctc tccagcaaga ggctagcact gaattcattc    3360
tactcatact acacacccag ttatggaatg tccagagttc tcgaagaaaa taaatgactt    3420
taggaagagg tatacatttt ttaagtcgct ctgcctccaa atctgaacag tcactgtaaa    3480
tcattcttaa gcccagatat gagaacttct gctggaaagt gggaccctct gagtgggtgg    3540
agtggaacca catgagcctg ctcagctctg cataagtaat tcaagaaatg ggaggcttca    3600
ccttaaaaac agtgtgcaaa tggcagctag aggttttgat aggaagtatg tttgtttctt    3660
```

```
agtgtttaca aatattaagt actcttgata caaaatatac tttaaactt cataacctt    3720 ttataaaagt tgttgcagca aaataatagc ctcggttcta tgcatatatg gattagctat    3780
aaaaaatgtc aataagattg tacaaggaaa attagagaaa gtcacattta gggtttattt    3840
tttacacttg gccagtaaaa tagggtaaat cctattagaa tttttttaaag aacttttttt    3900 aagtttccta atctgtgtg tgtattgtga agtggtataa gaaatgactt tgaaccactt    3960
tgcaattgta gattcccaac aataaaattg aagataaaaa aaaaaaaaaa aaaaaaaaaa    4020
aaaaaaa                                                              4027
```

<210> SEQ ID NO 3
<211> LENGTH: 571
<212> TYPE: PRT
<213> ORGANISM: Danio rerio

<400> SEQUENCE: 3

```
Met Met Met Met Asn Val Leu Ser Ala Leu Leu Leu Phe Ile His
1               5                   10                  15

Cys Gln Leu Cys Trp Ser Ala Asp Phe Gln Leu Thr Leu Leu His Thr
            20                  25                  30

Asn Asp Val His Ala Arg Val Glu Glu Thr Asn Lys Asp Ser Gly Lys
        35                  40                  45

Cys Ser Lys Pro Pro Cys Phe Ala Gly Val Ser Arg Arg Ser Thr Lys
    50                  55                  60

Ile Lys Glu Ile Arg Ser Lys Glu Lys Asn Val Leu Leu Leu Asp Ala
65                  70                  75                  80

Gly Asp Gln Phe Gln Gly Thr Val Trp Phe Asn Tyr Tyr Lys Gly Ala
                85                  90                  95

Glu Ala Ala Tyr Phe Met Asn Gln Leu Lys Tyr Asp Ala Met Ala Leu
            100                 105                 110

Gly Asn His Glu Phe Asp Asn Gly Val Asp Gly Leu Leu Lys Pro Phe
        115                 120                 125

Leu Gln Glu Val Asn Cys Thr Val Leu Ser Ala Asn Ile Lys Ala Asp
    130                 135                 140

Glu Thr Leu Ala Pro Arg Ile Ser Gly Tyr Tyr Phe Pro Tyr Lys Ile
145                 150                 155                 160

Phe Thr Leu Gly Ser Glu Lys Val Gly Val Gly Tyr Thr Ser Ala
                165                 170                 175

Glu Thr Pro Ala Leu Ser Leu Pro Gly Pro His Leu Lys Phe Glu Asp
            180                 185                 190

Glu Ile Thr Ala Leu Gln Pro Gln Val Asp Lys Leu Leu Thr Leu Gly
        195                 200                 205

Val Asn Lys Ile Ile Ala Leu Gly His Ser Gly Phe Leu Met Asp Gln
    210                 215                 220

Met Ile Ala Lys Lys Val Gln Gly Val Asp Val Ile Gly His
225                 230                 235                 240

Thr Asn Thr Phe Leu Tyr Thr Gly Asp Pro Ser Thr Glu Val Pro
                245                 250                 255

Ala Gly Pro Tyr Pro Leu Met Val Lys Ser Asp Asp Gly Arg Gln Val
            260                 265                 270

Pro Val Val Gln Ala Tyr Ala Phe Gly Lys Tyr Leu Gly Phe Leu Lys
        275                 280                 285

Val Thr Phe Asp Ala Asn Gly Asn Val Leu Glu Ser Thr Gly Asn Pro
    290                 295                 300
```

Ile Leu Leu Asn Ser Ser Val Glu Pro Asp Pro Asp Ile Gln Ala Lys
305                 310                 315                 320

Val Asp Ser Trp Arg Met Asn Leu Ala Asn Tyr Ser Ser Gln Gln Val
            325                 330                 335

Gly Gln Thr Leu Val Phe Leu Asn Gly Thr Phe Glu Glu Cys Arg Phe
            340                 345                 350

Arg Glu Cys Asn Leu Gly Asn Leu Ile Cys Asp Ala Met Val His His
            355                 360                 365

Asn Ile Lys Tyr Ala Asp Glu Leu Gln Trp Asn His Val Ser Ser Cys
        370                 375                 380

Ile Leu Asn Gly Gly Ile Arg Gly Pro Ile Asp Glu Arg Asn Arg
385                 390                 395                 400

Asn Gly Ser Ile Thr Met Glu Asp Leu Ile Ala Val Leu Pro Phe Gly
            405                 410                 415

Gly Thr Phe Asp Leu Val Gln Leu Asn Gly Ser Thr Leu Leu Glu Ala
            420                 425                 430

Phe Glu His Ser Val Arg Arg His Gly Gly Asn Thr Gly Glu Phe Leu
        435                 440                 445

Gln Val Ser Gly Phe Gln Val Val Tyr Asp Leu Ser Lys Ala Pro Gly
    450                 455                 460

Ser Arg Val Lys Ser Val Lys Val Leu Cys Thr Gln Cys Arg Val Pro
465                 470                 475                 480

His Tyr Glu Pro Leu Val Pro Asn Lys Val Tyr Lys Val Val Leu Pro
            485                 490                 495

Ser Tyr Leu Val Asp Gly Gly Asp Gly Phe Thr Met Ile Lys Glu Lys
            500                 505                 510

Lys Leu Lys His Asp Ser Gly Asp Leu Asp Ile Ser Val Val Ala Gly
        515                 520                 525

Tyr Ile Ser Glu Arg Lys Arg Val His Pro Ala Val Glu Gly Arg Phe
    530                 535                 540

Gln Phe Ser Ser Ser Cys Ala Gly Leu Arg Gly Tyr Thr Ser Thr Val
545                 550                 555                 560

Leu Leu Leu Trp Ala Val Trp Leu Met Leu Val
            565                 570

<210> SEQ ID NO 4
<211> LENGTH: 2116
<212> TYPE: DNA
<213> ORGANISM: Danio rerio

<400> SEQUENCE: 4
attttacagt aggaggatga tgatgatgat gaatgtcctc tccgcgttgc tgctgctctt    60
cattcactgt cagctgtgct ggtctgcgga cttccagctc actttgctgc acaccaatga   120
cgtgcacgcg cgagtggagg agaccaacaa ggactcgggc aaatgcagca agccgccgtg   180
tttcgccgga gtgtcgcgga gatccaccaa aatcaaagaa tccgcagca aggagaaaaa    240 cgtgctgctg ctggacgcag agaccagtt ccagggcacc gtctggttta actattacaa    300
gggcgctgag gcggcgtatt tcatgaacca gctcaaatac gacgcgatgg ctttaggaaa   360
ccatgagttt gacaacggcg tggacggcct gctgaaacct ttccttcagg aggtgaactg   420
cactgttctc agcgccaaca tcaaagctga tgagacactt gctcctcgga tcagcggata   480
ctatttccca tataaaatct tcacgttggg ctcagagaaa gtgggtgttg tcggctacac   540
atcggcggag acgcctgctt tgtctctacc aggcccacat ctgaagtttg aggatgaaat   600

```
cacggctcta cagcctcaag tggataaact cttgactttg ggtgttaata agatcatcgc    660
tctgggacat tctggcttcc taatggatca aatgatcgcg aagaaggttc agggagtgga    720
cgttgtgatt ggaggacaca ccaatacatt cttgtacacg ggagatccac cgtccacaga    780
agttcccgca gggccgtatc cactcatggt caagtcagac gacggccggc aggtgcctgt    840
ggtccaggct tatgcctttg gaaaatatct gggattcctg aaagtgactt ttgatgcaaa    900
cggaaatgtg ctggagtcga caggaaaccc cattcttctg aatagttcag tagaacccga    960
tcccgacatc caggctaaag tggacagctg gaggatgaat ctggccaact actcctctca   1020
gcaagtggga cagactctag tcttcctcaa cggcaccttc gaggagtgtc gctttcgtga   1080
atgcaatttg gggaatttaa tctgtgatgc catggtccat cataatatta aatacgccga   1140
cgagctccag tggaaccatg tcagctcttg tattctaaac ggtggaggca ttcgaggacc   1200
tattgatgag cgaaacagaa acggttccat cacaatggag gacctgatcg ccgtgctgcc   1260
gtttggagga acattcgacc tggtccagct gaacggatcg actctattag aagcttttga   1320
gcactcagtt cgccgacacg gaggaaacac tggagaattc ctacaggtgt caggttttca   1380
ggtggtgtat gatttatcga aagcgcctgg tagccgtgtt aaaagtgtga agtgctctg    1440 cacccagtgt cgagtgcctc attatgaacc gctggtcccc aacaaggtgt ataaagtagt   1500
gctgccgtct tacctagtgg acggaggaga cggattcacc atgatcaaag agaagaaact   1560
caaacacgac agcggtgatc tggatatatc ggttgttgct ggctacatct ccgagaggaa   1620
gagagttcat ccggctgtgg agggacgctt ccagttcagc agctcctgtg ctggtcttcg   1680
gggatacacg tccaccgttc tgctgctgtg ggccgtctgg ctcatgcttg tttagccagt   1740
aaacatcatt ctaatgcact ttgtacaaca tctagcccct ttatgtgtga ctgtacagtc   1800
agatgaggaa aaaagaaacc tctagcccaa agatgagttg tcttcatagg agtcgactga   1860
taattaacac tgtgatgtag aacagatgac ctaaaatccc tcttcttgta aaacaagatc   1920
ttatcataag agaaacacag ggacagtgtc attataccte tgtatacatg taacactcca   1980
tctttgtgcg gggagctatt tcatgaggaa taatccagga atctgagtta taaaacatta   2040
gaaacattcc tacaagtgag cgtctgcctc aataaatgtg tatttatttt gttaatgata   2100
aaaaaaaaaa aaaaaa                                                  2116
```